United States Patent
Kottwitz et al.

(10) Patent No.: US 7,320,887 B2
(45) Date of Patent: Jan. 22, 2008

(54) ALKALINE PROTEASE VARIANTS

(75) Inventors: Beatrix Kottwitz, Erkrath (DE); Karl-Heinz Maurer, Erkrath (DE); Roland Breves, Mettmann (DE)

(73) Assignee: Henkel Kommanditgesellschaft auf Aktien, Duesseldorf (DE)

(*) Notice: Subject to any disclaimer, the term of this patent is extended or adjusted under 35 U.S.C. 154(b) by 329 days.

(21) Appl. No.: 10/836,959

(22) Filed: Apr. 30, 2004

(65) Prior Publication Data

US 2005/0003985 A1 Jan. 6, 2005

Related U.S. Application Data

(63) Continuation of application No. PCT/EP02/11725, filed on Oct. 19, 2002.

(30) Foreign Application Priority Data

Oct. 31, 2001 (DE) .............................. 101 53 792

(51) Int. Cl.
  *C12N 9/54* (2006.01)
  *C12N 15/57* (2006.01)
  *C12N 15/74* (2006.01)
  *C11D 3/386* (2006.01)
(52) U.S. Cl. .................. 435/221; 435/69.1; 435/252.3; 435/320.1; 510/300
(58) Field of Classification Search .................... None
  See application file for complete search history.

(56) References Cited

U.S. PATENT DOCUMENTS

| | | |
|---|---|---|
| 3,623,957 A | 11/1971 | Feldman |
| 3,893,929 A | 7/1975 | Basadur |
| 4,116,885 A | 9/1978 | Derstadt et al. |
| 4,264,738 A | 4/1981 | Stepanov et al. |
| 4,760,025 A | 7/1988 | Estell et al. |
| 4,820,439 A | 4/1989 | Rieck |
| 5,230,891 A | 7/1993 | Nakayama et al. |
| 5,340,735 A | 8/1994 | Christianson et al. |
| 5,344,770 A | 9/1994 | Hitomi et al. |
| 5,352,604 A | 10/1994 | Wilson et al. |
| 5,441,882 A | 8/1995 | Estell et al. |
| 5,453,372 A | 9/1995 | Vetter et al. |
| 5,543,302 A | 8/1996 | Boguslawski et al. |
| 5,550,364 A | 8/1996 | Rudeen |
| 5,614,161 A | 3/1997 | Wilkens et al. |
| 5,665,587 A | 9/1997 | Aaslyng et al. |
| 5,677,141 A | 10/1997 | Isogai et al. .................. 435/47 |
| 5,677,272 A | 10/1997 | Ghosh et al. |
| 5,691,295 A | 11/1997 | Maurer et al. |
| 5,700,676 A | 12/1997 | Bott et al. |
| 5,705,169 A | 1/1998 | Stein et al. |
| 5,730,960 A | 3/1998 | Stein et al. |
| 5,739,091 A | 4/1998 | Kiesser et al. |
| 5,783,545 A | 7/1998 | Paatz et al. |
| 5,801,038 A | 9/1998 | Bott et al. |
| 5,801,039 A | 9/1998 | Maurer et al. |
| 5,855,625 A | 1/1999 | Maurer et al. |
| 5,858,757 A | 1/1999 | Von Der Osten et al. |
| 5,945,091 A | 8/1999 | Habeck et al. |
| 5,962,613 A | 10/1999 | Schade et al. |
| 5,972,873 A | 10/1999 | Nielsen et al. |
| 5,985,639 A | 11/1999 | Christianson et al. |
| 6,017,871 A | 1/2000 | Baeck et al. |
| 6,066,611 A | 5/2000 | Ghosh et al. |
| 6,075,001 A | 6/2000 | Wilde |
| 6,083,898 A | 7/2000 | Meixner et al. |
| 6,087,315 A | 7/2000 | Rasmussen et al. |
| 6,110,884 A | 8/2000 | Rasmussen et al. |
| 6,136,553 A | 10/2000 | Christianson et al. |
| 6,187,055 B1 | 2/2001 | Kottwitz et al. |
| 6,193,960 B1 | 2/2001 | Metzger et al. |
| 6,197,589 B1 | 3/2001 | Maurer et al. |
| 6,228,827 B1 | 5/2001 | Penninger et al. |
| 6,379,394 B1 | 4/2002 | Chilou et al. |
| 6,417,152 B1 | 7/2002 | Kottwitz et al. |
| 6,509,021 B1 | 1/2003 | Weiss et al. |
| 6,599,730 B1* | 7/2003 | Brode et al. ................. 435/221 |

(Continued)

FOREIGN PATENT DOCUMENTS

| | | |
|---|---|---|
| CA | 958 618 | 12/1974 |
| CA | 2048064 | 2/1992 |
| CA | 2049097 | 2/1992 |
| CA | 2 306 376 | 10/2000 |
| DE | 1 940 488 | 2/1971 |
| DE | 16 17 141 | 4/1972 |
| DE | 2 121 397 | 11/1972 |
| DE | 2 253 063 | 5/1973 |
| DE | 2 200 911 | 10/1973 |

(Continued)

OTHER PUBLICATIONS

PIR Database Accession No. 36734, 2000, Sloma et al., bacillopeptidase F precursor (three sheets printed).*

(Continued)

*Primary Examiner*—Nashaat T Nashed
*Assistant Examiner*—William W. Moore
(74) *Attorney, Agent, or Firm*—Woodcock Washburn LLP

(57) ABSTRACT

The invention relates to novel alkaline protease variants. These variants have, when enumerating the alkaline protease from *Bacillus lentus*, variations in amino acid position 61, positions 199 and/or 211 and, optionally, at least one modification that contributes to the stabilization of the molecule, said modification preferably being point mutations in positions 3 and/or 4. Particularly preferred are variants S3T/V41/G61A/V199] and S3T/V41/G61A/V1991/L211D of *B. lentus* alkaline protease. The invention also relates to the possible use of these enzymes in diverse technical processes and, in particular, to detergents and cleansers containing these novel alkaline protease variants.

19 Claims, 3 Drawing Sheets

U.S. PATENT DOCUMENTS

| | | |
|---|---|---|
| 6,703,357 B1 | 3/2004 | Maurer et al. |
| 6,893,855 B2 * | 5/2005 | Nørregaard-Madsen et al. .................. 435/220 |
| 2005/0181446 A1 * | 8/2005 | Roggen et al. ............ 435/7.1 |

FOREIGN PATENT DOCUMENTS

| | | |
|---|---|---|
| DE | 28 57 292 A1 | 2/1980 |
| DE | 33 24 258 A1 | 1/1984 |
| DE | 40 131 42 A1 | 10/1991 |
| DE | 44 43 177 A1 | 6/1996 |
| DE | 196 01 063 A1 | 9/1996 |
| DE | 196 16 693 A1 | 11/1997 |
| DE | 196 16 767 A1 | 11/1997 |
| DE | 196 16 769 A1 | 11/1997 |
| DE | 196 16 770 A1 | 11/1997 |
| DE | 196 50 537 A1 | 6/1998 |
| DE | 197 09 284 A1 | 9/1998 |
| DE | 197 12 033 A1 | 9/1998 |
| DE | 199 18 267 A1 | 10/2000 |
| EP | 0 006 638 A2 | 1/1980 |
| EP | 0 028 865 B2 | 3/1984 |
| EP | 0 080 748 B1 | 7/1985 |
| EP | 0 080 223 B1 | 7/1986 |
| EP | 0 199 404 A2 | 10/1986 |
| EP | 0 066 944 B1 | 11/1986 |
| EP | 0 126 505 B1 | 1/1987 |
| EP | 0 251 446 A2 | 1/1988 |
| EP | 0 272 033 A2 | 6/1988 |
| EP | 0 164 514 B1 | 6/1989 |
| EP | 0 328 229 A1 | 8/1989 |
| EP | 0 380 362 A1 | 8/1990 |
| EP | 0 253 567 B1 | 12/1990 |
| EP | 0 241 985 B1 | 1/1991 |
| EP | 0 405 901 A1 | 1/1991 |
| EP | 0 472 042 A1 | 2/1992 |
| EP | 0 185 427 B1 | 3/1992 |
| EP | 0 274 907 B1 | 8/1992 |
| EP | 0 516 200 A1 | 12/1992 |
| EP | 0 525 610 A2 | 2/1993 |
| EP | 0 378 262 B1 | 12/1993 |
| EP | 0 241 984 B1 | 3/1994 |
| EP | 0 378 261 B1 | 7/1994 |
| EP | 0 357 280 B1 | 2/1996 |
| EP | 0 398 539 B1 | 8/1996 |
| EP | 0 755 999 A1 | 1/1997 |
| EP | 0 583 534 B1 | 3/1997 |
| EP | 0 780 466 A1 | 6/1997 |
| EP | 0 525 239 B1 | 7/1997 |
| EP | 0 656 058 B1 | 12/1997 |
| EP | 0 693 471 B1 | 1/1998 |
| EP | 0 694 521 B1 | 1/1998 |
| EP | 0 533 239 B1 | 4/1998 |
| EP | 0 583 339 B1 | 7/1998 |
| EP | 0 736 084 B1 | 9/1998 |
| EP | 0 581 751 B1 | 12/1998 |
| EP | 0 587 550 B1 | 12/1998 |
| EP | 0 702 712 B1 | 12/1998 |
| EP | 0 283 075 B1 | 5/1999 |
| EP | 0 493 398 B1 | 12/1999 |
| EP | 0 995 801 A1 | 4/2000 |
| EP | 0 130 756 B2 | 6/2000 |
| EP | 0 755 944 B1 | 10/2001 |
| EP | 0 818 450 B1 | 1/2003 |
| EP | 0 728 749 B1 | 4/2003 |
| GB | 1154730 | 6/1969 |
| GB | 1 243 784 A | 8/1971 |
| GB | 1 263 765 | 2/1972 |
| GB | 2 123 848 A | 2/1984 |
| WO | WO88/07581 A1 | 10/1988 |
| WO | WO88/08028 A1 | 10/1988 |
| WO | WO88/08033 A1 | 12/1988 |
| WO | WO89/06279 A1 | 7/1989 |
| WO | WO89/09819 A1 | 10/1989 |
| WO | WO89/09830 A1 | 10/1989 |
| WO | WO91/00334 A1 | 1/1991 |
| WO | WO91/00345 A1 | 1/1991 |
| WO | WO91/02792 A1 | 3/1991 |
| WO | WO91/06637 A1 | 5/1991 |
| WO | WO92/11348 A1 | 7/1992 |
| WO | WO92/19707 A1 | 11/1992 |
| WO | WO92/19729 A1 | 11/1992 |
| WO | WO92/21760 A1 | 12/1992 |
| WO | WO93/00418 A1 | 1/1993 |
| WO | WO93/07276 A1 | 4/1993 |
| WO | WO93/18140 A1 | 9/1993 |
| WO | WO94/02618 A1 | 2/1994 |
| WO | WO94/27970 A1 | 12/1994 |
| WO | WO94/28102 A1 | 12/1994 |
| WO | WO94/28103 A1 | 12/1994 |
| WO | WO95/00626 A1 | 1/1995 |
| WO | WO95/07688 A1 | 3/1995 |
| WO | WO95/07991 A2 | 3/1995 |
| WO | WO95/10591 A1 | 4/1995 |
| WO | WO95/12655 A1 | 5/1995 |
| WO | WO95/14075 A1 | 5/1995 |
| WO | WO95/14759 A1 | 6/1995 |
| WO | WO95/17498 A1 | 6/1995 |
| WO | WO95/23221 A1 | 8/1995 |
| WO | WO95/29979 A1 | 11/1995 |
| WO | WO95/30010 A1 | 11/1995 |
| WO | WO95/30011 A2 | 11/1995 |
| WO | WO95/32232 A1 | 11/1995 |
| WO | WO96/25489 A1 | 8/1996 |
| WO | WO96/28556 A2 | 9/1996 |
| WO | WO96/28557 A2 | 9/1996 |
| WO | WO96/28558 A1 | 9/1996 |
| WO | WO96/28566 A2 | 9/1996 |
| WO | WO96/31589 A1 | 10/1996 |
| WO | WO96/34935 A2 | 11/1996 |
| WO | WO97/00932 A1 | 1/1997 |
| WO | WO97/05227 A1 | 2/1997 |
| WO | WO97/07770 A1 | 3/1997 |
| WO | WO97/18287 A1 | 5/1997 |
| WO | WO97/24177 A1 | 7/1997 |
| WO | WO97/25399 A1 | 7/1997 |
| WO | WO97/31085 A1 | 8/1997 |
| WO | WO97/32958 A1 | 9/1997 |
| WO | WO97/43377 A1 | 11/1997 |
| WO | WO98/13459 A1 | 4/1998 |
| WO | WO98/13460 A1 | 4/1998 |
| WO | WO98/13462 A1 | 4/1998 |
| WO | WO98/17764 A1 | 4/1998 |
| WO | WO98/30669 A1 | 7/1998 |
| WO | 98/36085 A1 | 8/1998 |
| WO | WO98/45396 A1 | 10/1998 |
| WO | WO99/06515 A1 | 2/1999 |
| WO | WO99/06516 A1 | 2/1999 |
| WO | WO99/18219 A1 | 4/1999 |
| WO | WO99/20723 A2 | 4/1999 |
| WO | WO99/20726 A1 | 4/1999 |
| WO | WO99/20727 A1 | 4/1999 |
| WO | WO99/27082 A1 | 6/1999 |
| WO | WO99/43780 A1 | 9/1999 |
| WO | 0 828 762 B1 | 10/1999 |
| WO | WO99/57154 A1 | 11/1999 |
| WO | WO99/57157 A1 | 11/1999 |
| WO | WO99/63038 A1 | 12/1999 |
| WO | WO99/63041 A1 | 12/1999 |
| WO | WO 00/01826 A1 | 1/2000 |
| WO | WO 00/01831 A2 | 1/2000 |
| WO | WO 00/18865 A1 | 4/2000 |
| WO | WO 00/24924 A2 | 5/2000 |
| WO | WO 00/36069 A1 | 6/2000 |

| | | |
|---|---|---|
| WO | WO 00/37599 A1 | 6/2000 |
| WO | WO 00/37621 A1 | 6/2000 |
| WO | WO 00/37627 A1 | 6/2000 |
| WO | WO 00/39306 A2 | 7/2000 |
| WO | WO 00/42145 A1 | 7/2000 |
| WO | WO 00/57155 A1 | 9/2000 |
| WO | WO 00/71683 A1 | 11/2000 |
| WO | WO 00/71691 A1 | 11/2000 |
| WO | WO 01/38471 A1 | 5/2001 |
| WO | WO 01/81597 A1 | 11/2001 |

OTHER PUBLICATIONS

Sloma, A., et al., 1990, "Bacillopeptidase F of *Bacillus subtilis*: Purification of the protein and cloning of the gene", Journal of Bacteriology, vol. 172, pp. 1470-1477.*

Wu, X. C., et al., 1990, "Cloning, genetic organization, and characterization of a structural gene encoding bacillopeptidase F from *Bacillus subtilis*", The Journal of Biological Chemistry, vol. 265, pp. 6845-6850.*

Vasantha et al., J. Bacteriol., vol. 159, pp. 811-819 (1984).

Wells et al., Nucleic Acids Research, vol. 11, pp. 7911-7925 (1983).

Smith et al., J. Biol. Chem., vol. 243, pp. 2184-2191 (1968).

Jacobs et al., Nucl. Acids Res., vol. 13, pp. 8913-8926 (1985).

Nedkov et al., Biol. Chem Hoppe-Seyler, vol. 366, pp. 421-430 (1985).

Meloun et al., FEBS Letters, pp. 195-200 (Apr. 1985).

K. D. Jany et al., Biol. C hem. Hoppe-Seyler, vol. 366, pp. 485-492 (May 1985).

Zhao et al., Nat. Biotechnol. vol. 16, pp. 258-261 (Mar. 1998).

Shao et al., Nucleic Acids Res. vol. 26, No. 2, pp. 681-683 (1998).

Stemmer, DNA Shuffling, Nature, vol. 370, pp. 389-391 (Aug. 4, 1994).

Coco et al., Nat. Biotechnol. vol. 19, pp. 354-359 (2001).

Goddette et al., "The crystal structure of the *Bacillus lentus* alkaline protease, Subtilisin BL, at 1.4 resolution", J. Mol. Biol. vol. 228, pp. 580-595 (1992).

Lexikon der Biochemie, Spektrum Akademischer Verlag, Berlin, vol. 1, pp. 267-271 (1991).

Lexikon der Biochemie, Spektrum Akademischer Verlag, Berlin, vol. 1, pp. 227-229 (1999).

Fritsch et al., "Molecular Cloning:a laboratory Manual", Cold Spring Harbour Laboratory Press New York (1989).

vol P.N. Bryan, "Protein Engineering", Biochim, Biophys. Acta, vol. 1543, pp. 203-222 (2000).

Tenside, vol. 7, pp. 125-132 (1970) (English summary provided on p. 131).

K. H. Wallhauber, "Praxis der Sterilisation, Desinfektion-Konservierung: Keimidentifizierung-Betriebshygiene", 5th Edition, Stuttgart, New York:Thieme (1995).

Finkel, SOFW Journal, vol. 122, pp. 543-548 (1996) (English summary provided on p. 543).

R. Breier, Melliand Textilberichte, pp. 298 and 300-302 (2000).

Rompp, Lexikon Chemie, Version 2.0, Stuttgart/New York; George Thieme Verlag (1999).

T. Egelrud et al., Acta Derm. Venerol., vol. 71, pp. 471-474 (1991).

Kawamura et al., J. Bacteriol., vol. 160, pp. 442-444 (Oct. 1984).

Chang et al., "Protoplastenmethode", Molec. Gen. Genet., vol. 168, pp. 111-115 (1979).

PCT/EP02/11725 Search Report dated Apr. 28, 2003.

* cited by examiner

Figure 1/Part 1

```
                              1                                                                           70
S3T/V4I/G61A/V199I        (1) AQTIPWGISRVQAPAAHNRGLTGSGVKVAVLDTGIS-THPDLNIRGGASFVPGEPS-TQDGNAHGTHVAG
S3T/V4I/G61A/V199I/L211D  (1) AQTIPWGISRVQAPAAHNRGLTGSGVKVAVLDTGIS-THPDLNIRGGASFVPGEPS-TQDGNAHGTHVAG
Subtilisin 309            (1) AQSVPWGISRVQAPAAHNRGLTGSGVKVAVLDTGIS-THPDLNIRGGASFVPGEPS-TQDGNGHGTHVAG
Subtilisin PB92           (1) AQSVPWGISRVQAPAAHNRGLTGSGVKVAVLDTGIS-THPDLNIRGGASFVPGEPS-TQDGNGHGTHVAG
Subtilisin Carlsberg      (1) AQTVPYGIPLIKADKVQAQGFKGANVKVAVLDTGIQASHPDLNVVGGASFVAGEAY-NTDGNGHGTHVAG
Subtilisin BPN'           (1) AQSVPYGVSQIKAPALHSQGYTGSNVKVAVIDSGIDSSHPDLKVAGGASMVPSETNPFQDNNSHGTHVAG
Consensus                 (1) AQ  PWGISRVQAPAAHNRGLTGSGVKVAVLDTGIS THPDLNIRGGASFVPGEPS TQDGN HGTHVAG 71                                                                         140
S3T/V4I/G61A/V199I       (69) TIAALNNSIGVLGVAPSAELYAVKVLGADGRGAISSIAQGLEWAGNNGMHVANLSLGSPSPSATLEQAVN
S3T/V4I/G61A/V199I/L211D (69) TIAALNNSIGVLGVAPSAELYAVKVLGADGRGAISSIAQGLEWAGNNGMHVANLSLGSPSPSATLEQAVN
Subtilisin 309           (69) TIAALNNSIGVLGVAPSAELYAVKVLGASGSGVSSIAQGLEWAGNNGMHVANLSLGSPSPSATLEQAVN
Subtilisin PB92          (69) TIAALNNSIGVLGVAPNAELYAVKVLGASGSGVSSIAQGLEWAGNNGMHVANLSLGSPSPSATLEQAVN
Subtilisin Carlsberg     (70) TVAALDNTTGVLGVAPSVSLYAVKVLNSSGSGTYSGIVSGIEWATTNGMDVINMSLGGPSGSTAMKQAVD
Subtilisin BPN'          (71) TVAALNNSIGVLGVAPSASLYAVKVLGADGSGQYSWIINGIEWAIANNMDVINMSLGGPSGSAALKAAVD
Consensus                (71) TIAALNNSIGVLGVAPSAELYAVKVLGASGSGVSSIAQGLEWAGNNGMHVANLSLGSPSPSATLEQAVN 141                                                                        210
S3T/V4I/G61A/V199I      (139) SATSRGVLVVAASGNSG-----ASSISYPARYANAMAVGATDQNNNRASFSQYGAGLDIVAPGVNIQSTYP
S3T/V4I/G61A/V199I/L211D(139) SATSRGVLVVAASGNSG-----ASSISYPARYANAMAVGATDQNNNRASFSQYGAGLDIVAPGVNIQSTYP
Subtilisin 309          (139) SATSRGVLVVAASGNSG-----AGSISYPARYANAMAVGATDQNNNRASFSQYGAGLDIVAPGVNVQSTYP
Subtilisin PB92         (139) SATSRGVLVVAASGNSG-----AGSISYPARYANAMAVGATDQNNNRASFSQYGAGLDIVAPGVNVQSTYP
Subtilisin Carlsberg    (140) NAYARGVVVAAAGNSGSSGNTNTIGYPAKYDSVIAVGAVDSNSNRASFSSVGAELEVMAPGAGVYSTYP
Subtilisin BPN'         (141) KAVASGVVVVAAAGNEGTSGSSSTVGYPGKYPSVIAVGAVDSSNQRASFSSVGPELDVMAPGVSIQSTLP
Consensus               (141) SATSRGVLVVAASGNSG     A  SISYPARYANAMAVGATDQNNNRASFSQYGAGLDIVAPGVN QSTYP
```

Figure 1/Part 2

```
                              211                                                              275
S3T/V4I/G61A/V199I      (205) GSTYASLNGTSMATPHVAGAAAALVKQKNPSWSNVQIRNHLKNTATSLGSTNLYGSGLVNAEAATR
S3T/V4I/G61A/V199I/L211D (205) GSTYASDNGTSMATPHVAGAAAALVKQKNPSWSNVQIRNHLKNTATSLGSTNLYGSGLVNAEAATR
Subtilisin 309          (205) GSTYASLNGTSMATPHVAGAAAALVKQKNPSWSNVQIRNHLKNTATSLGSTNLYGSGLVNAEAATR
Subtilisin PB92         (205) GSTYASLNGTSMATPHVAGAAAALVKQKNPSWSNVQIRNHLKNTATSLGSTNLYGSGLVNAEAATR
Subtilisin Carlsberg    (210) TSTYATLNGTSMASPHVAGAAAALILSKHPNLSASQVRNRLSSTATYLGSSFYYGKGLINVEAAAQ
Subtilisin BPN'         (211) GNKYGAYNGTSMASPHVAGAAAALILSKHPNWTNTQVRSSLENTTTKLGDSFYYGKGLINVQAAAQ
Consensus               (211) GSTYAS NGTSMATPHVAGAAAALVKQKNPSWSNVQIRNHLKNTATSLGSTNLYGSGLVNAEAATR
```

ALKALINE PROTEASE VARIANTS

CROSS REFERENCE TO RELATED APPLICATIONS

This application is a continuation of PCT/EP02/11725, filed Oct. 19, 2002, which claims the benefit of DE 101 53 792.1, filed Oct. 31, 2001.

FIELD OF THE INVENTION

The present invention relates to novel alkaline protease variants. According to the numbering of *Bacillus lentus* alkaline protease, these have variations at amino acid position 61, at positions 199 and/or 211 and optionally at least one modification contributing to stabilization of the molecule, preferably point mutations at positions 3 and/or 4. The present invention also relates to possible uses of said enzymes in various technical processes and, in particular, to detergents and cleaning agents containing said novel alkaline protease variants.

BACKGROUND

Proteases of the subtilisin type (subtilases, subtilopeptidases, EC 3.4.21.62) are classed as belonging to the serine proteases, owing to the catalytically active amino acids. They are naturally produced and secreted by microorganisms, in particular by *Bacillus* species. They act as unspecific endopeptidases, i.e. they hydrolyze any acid amide bonds located inside peptides or proteins. Their pH optimum is usually within the distinctly alkaline range. A review of this family is provided, for example, by the paper "Subtilases: Subtilisin-like Proteases" by R. Siezen, pages 75-95 in "Subtilisin enzymes", edited by R. Bott and C. Betzel, New York, 1996. Subtilisins are suitable for a multiplicity of possible technical uses, as components of cosmetics and, in particular, as active ingredients of detergents or cleaning agents.

Apart from other enzymes such as, for example, amylases, lipases or cellulases, proteases are used as active components in detergents and cleaning agents. They have the ability to break down proteinaceous soilings on the material to be cleaned such as, for example, textiles or dishes. Owing to their relatively high solubility, the hydrolysis products are washed away with the wash liquor or are attacked, dissolved, emulsified or suspended by the other components of the detergents or cleaning agents. Thus, synergistic effects between the enzymes and the other components of the detergents and cleaning agents in question can arise. Owing to their favorable enzymic properties such as stability or pH optimum, subtilisins stand out among the detergent and cleaning agent proteases. The most important ones and the most important strategies for their technical development are stated below.

The fundamental strategy for developing detergent proteases is to first isolate microbially and naturally produced enzymes and to test them for their principle suitability for this possible use. These molecules may then be optimized. Thus, for example, the protease 164-A1 from Chemgen Corp., Gaithersburg, Md., USA, and Vista Chemical Company, Austin, Tex., USA, obtainable from *Bacillus* spec. 164-A1, is suitable for use in detergents and cleaning agents, according to the application WO 93/07276 A1. Other examples are alkaline protease from *Bacillus* sp. PD138, NCIMB 40338 from Novozymes (WO 93/18140 A1), the proteinase K-16 from Kao Corp., Tokyo, Japan, derived from *Bacillus* sp. ferm. BP-3376 (U.S. Pat. No. 5,344,770) and, according to WO 96/25489 A1 (Procter & Gamble, Cincinnati, Ohio, USA), the protease of the psychrophilic organism *Flavobacterium balustinum*.

Subtilisin BPN' which is derived from *Bacillus amyloliquefaciens*, and *B. subtilis*, respectively, has been disclosed in the studies by Vasantha et al. (1984) in J. Bacteriol., Volume 159, pp. 811-819 and by J. A. Wells et al. (1983) in *Nucleic Acids Research*, Volume 11, pp. 7911-7925. Subtilisin BPN' serves as reference enzyme of the subtilisins, in particular with respect to numbering of positions. Thus, for example, the point mutations of the application EP 130756 A1 which refer to all subtilisins are also indicated with BPN' numbering. These merely include position 217 which corresponds to position 211 in enzymes of the invention; no particular substitution is specifically emphasized for this; all of them are mentioned, except replacement with M, W, C or K; preference should be given to that with A or S.

The application CA 2049097 A1 studies multiple mutants of this molecule, in particular with respect to their stability in detergents and cleaning agents. These include variants containing the substitutions Y217K and Y217L and also the double mutant S63D/Y217K, i.e. those containing substitutions which correspond to positions 211 and, respectively, 61 and 211 of *B. lentus* alkaline protease. However, no amino acids corresponding to any of the proteases of the present application at these positions were introduced.

Variants obtained by point mutations in the loop regions of said enzyme and having reduced binding to the substrate with a simultaneously increased rate of hydrolysis are introduced, for example, in the patent applications WO 95/07991 A2 and WO 95/30010 A1. WO 95/07991 A2 relates to the sixth loop of the molecule and discloses double mutants in which, in addition to another mutation, the amino acids at position 217 (corresponding to 211 in *B. lentus* alkaline protease) has been mutated to D, for example. Since BPN' by nature has I at position 205 (corresponding to 199), these two positions at most may be regarded herein as having been described previously, but always in combination with other mutations in subtilisin loop regions and with specific changes in the enzymic properties. The patent application WO 95/29979 A1, for example, discloses detergents containing BPN' variants of this kind. WO 95/30010 A1 discloses further mutations in the other five loop regions, including at position 63 (corresponding to 61), but only to D or E at this position. In contrast, two of the amino acid positions considered in the present patent application, namely positions 3 and 4, are not located in loop regions. On the other hand, the numerous substitutions indicated in said documents do not correlate with stabilizations, in particular with stabilizing mutations of subtilisin BPN'.

The publications by E. L. Smith et al. (1968) in *J. Biol. Chem.*, Volume 243, pp. 2184-2191, and by Jacobs et al. (1985) in *Nucl. Acids Res.*, Volume 13, pp. 8913-8926 introduce the protease subtilisin Carlsberg. It is naturally produced by *Bacillus licheniformis* and was and, respectively, is obtainable under the trade name Maxatase® from Genencor International Inc., Rochester, N.Y., USA, and under the trade name Alcalase® from Novozymes A/S, Bagsvaerd, Denmark. Variants thereof which are obtainable by point mutations and have reduced binding to the substrate with a simultaneously increased rate of hydrolysis are disclosed, for example, by the application WO 96/28566 A2. These are variants in which single or multiple substitutions in the loop regions of the molecule have been carried out. The only variants having substitutions at positions corresponding to those of the present application, which have been tested in washing or cleaning experiments, are those of multiple mutants which have among other substitutions those of G62 (corresponding to position 61 of *B. lentus* alkaline protease) by N, D, Q, E, P or S, but not by A, of V204 (corresponding to position 199) by various other amino acids, but not by I, and of L216 (corresponding to position 211) by 14 other amino acids, including also by D. Thus, the only variations relating to the present application, which have been described previously by this document, are 3T—because T naturally occupies position 3 in subtilisin Carlsberg—and 211D.

The protease PB92 is produced naturally by the alkaliphilic bacterium *Bacillus nov.* spec. 92 and was obtainable under the trade name Maxacal® from Gist-Brocades, Delft, The Netherlands. Its original sequence is described in patent application EP 283075 A2. Variants of said enzyme which have been obtained by point mutation and which are suitable for use in detergents and cleaning agents are disclosed in the applications WO 94/02618 A1 and EP 328229 A1, for example. The first of said applications describes only substitutions at position 211, by various amino acids, but not by D. The second document discloses that particular regions in whch the two residues 61 and 211 are also present are involved in substrate binding. However, 61 is not listed among the positions particularly interesting for mutagenesis, and a substitution by Y is proposed for 211, which is able to increase the washing performance of a corresponding formulation only in combination with at least one further substitution, however.

The subtilisins 147 and 309 are sold by Novozymes under the trade names Esperase® and Savinase®, respectively. They are originally derived from *Bacillus* strains disclosed by the application GB 1243784 A. Variants of said enzymes, which have been developed by means of point mutagenesis with respect to usage in detergent and cleaning agents, are disclosed, for example, in the applications WO 94/02618 A1 (see above), WO 89/06279 A1, WO 95/30011 A2 and WO 99/27082 A1.

The application WO 89/06279 A1 aimed at achieving higher oxidation stability, an increased rate of proteolysis and enhanced washing performance. It reveals that substitutions at particular positions should alter the physical or chemical properties of subtilisin 147 or 309 molecules (whose numbering corresponds to that of *Bacillus lentus* DSM 5483 alkaline protease); among said positions, mention is made of, inter alia, position 199, but no special substitution is described. The application WO 95/30011 A2 introduces variants of subtilisin 309 which have point mutations in the loop regions of the molecule and thus exhibit reduced adsorption to the substrate with a simultaneously increased rate of hydrolysis. The positions 61, 199 and 211 are also present in such regions. The substitution L211D, inter alia, is proposed for position 211 therein; the substitutions of G by N, D, Q, E, P or S are proposed for positions 61, with numerous substitutions, but not I, being proposed for 199. The application WO 99/27082 A1 develops variants of, by way of example, subtilisin 309, whose washing performance is enhanced by enlarging the active loops by inserting at least one amino acid. Thus, they are not substitutions like in the present application.

Subtilisin DY has originally been described by Nedkov et al. 1985 in *Biol. Chem. Hoppe-Seyler*, Volume 366, pp. 421-430. According to the application WO 96/28557 A2, for example, it may be optimized via specific point mutations in the active loops for usage in detergents and cleaning agents, producing variants having reduced adsorption and an increased rate of hydrolysis, including those containing substitutions at position 62 (corresponding to 61 in *B. lentus* alkaline protease) of G by N, D, Q, E, P or S, at position 204 (corresponding to 199), but not 2041, and at position 216 (corresponding to 211) numerous substitutions, including also D. Since subtilisin DY by nature has T at position 3, only a variant 3T/211D has at most been previously described hereby.

The enzyme thermitase produced naturally by *Thermoactinomyces vulgaris* has originally been described by Meloun et al. (*FEBS Lett.* 1983, pp. 195-200). The application WO 96/28558 A2, for example, discloses variants having reduced absorption and an increased rate of hydrolysis, owing to substitutions in the loop regions. There, substitutions at position 211 (corresponding to 211 in *B. lentus* alkaline protease) by 14 amino acids, including also D, and at position 70 (corresponding to 61), of G by N, D, Q, E, P or S are described. Since I is naturally present at position 209 of thermitase (corresponding to 199), this suggests at most the variants 199I and 211D of the proteases essential to the present application. In particular it also does not suggest any stabilizations, for example by threonine at position 3 and/or isoleucine at position 4 (according to *B. lentus* alkaline protease). At the correspondingly, homologous positions 10 and 11, thermitase has the amino acids S and R (compare alignment in WO 91/00345 A1). Moreover, thermitase is a molecule whose sequence overall deviates considerably from those of the other subtilisins. Thus the homology between the mature proteins thermitase and *B. lentus* DSM 5483 alkaline protease (see below) is 45% identity (62% similar amino acids).

Proteinase K is also a protease which has comparatively low homology to *B. lentus* alkaline protease. Said homology is only 33% identity (46% similar amino acids) at the mature protein level. Proteinase K is originally from the microorganism *Tritirachium album* Limber and has been described by K.-D. Jany and B. Mayer 1985 in *Biol. Chem. Hoppe-Seyler*, Vol. 366, pp. 485-492. WO 88/07581 A1 discloses the very similar proteases TW3 and TW7, inter alia for usage in detergents and cleaning agents. The application WO 96/28556 A2 describes numerous substitutions in proteinase K, including at position 220 (corresponding to 211 in *B. lentus* alkaline protease) by 14 other amino acids, including also D, and at position 68 (corresponding to 61) of G by N, D, Q, E, P or S. Since proteinase K has by nature I at position 208 (corresponding to 199) and T at position 4 (corresponding to 3), this suggests at most the variations 3T, 199I and 211D of the proteases essential to the present application.

Finally, mention should also be made of *Bacillus subtilis* bacillopeptidase F which by nature has the amino acids alanine and isoleucine at positions 61 and 199, respectively. Otherwise, however, it has only low similarity to protease variants of the invention: at the amino acid level, only a homology of 30% identity, or 38% of similar amino acids, can be found. This enzyme is listed in the abovementioned work by Siezen et al., but up until now has not been described or claimed yet for usage in detergents and cleaning agents.

The applications EP 199404 A2, EP 251446 A1, WO 91/06637 A1 and WO 95/10591 A1, for example, describe further proteases which are referred to by Procter & Gamble Comp., Cincinnati, Ohio, USA as "protease A", "protease B", "protease C" and "protease D", respectively, and which are suitable for technical use, in particular in detergents and cleaning agents. The proteases of the application EP 199404 are various BPN' variants which are based on the application EP 130756 A1 (see above), but which have no variations at the positions relevant to the present application. EP 251446 A1 discloses numerous BPN' variants, including also 217-variants (corresponding to position 211 in *B. lentus* alkaline protease); any possible substitutions are mentioned here, not disclosing, however, which properties accompany the variation 217D. According to the application WO 91/06637 A1, "proteases C" are distinguished by point mutations of BPN' at positions 123 and/or 274. "Protease D" comprises variants, primarily of *Bacillus lentus* protease, which, according to WO 95/10591 A1, carry mutations at position 76 (according to BPN' numbering, corresponding to position 74 in *B. lentus* alkaline protease) and, in addition at other positions. The latter may also include position 217 (corresponding to 211); however, no substitution by D has been previously described therein. Virtually the same also applies to U.S. Pat. No. 6,017,871 A, for example, for usage in detergents and cleaning agents and cosmetics and to U.S. Pat. No. 5,677,272 A and U.S. Pat. No. 6,066,611 A, for example, for usage in bleaches: there, the substitution 217D is also mentioned in principle, again in combination with the substitution at position 76, but is not preferred.

Other known proteases are the enzymes obtainable under the trade names Durazym®, Relase®, Everlase®, Nafizym, Natalase® and Kannase® from Novozymes, under the trade names Maxapem®, Purafect®, Purafect OxP® and Properase® from Genencor, under the trade name Protosol® from Advanced Biochemicals Ltd., Thane, India and under the trade name Wuxi® from Wuxi Snyder Bioproducts Ltd., China.

One strategy for enhancing the washing performance of subtilisins is to introduce randomly or specifically point mutations into the known molecules, owing to known functions of individual amino acids, and to test the variants obtained for their washing performance contributions. This strategy is pursued, for example, by U.S. Pat. No. 5,700,676 and the application EP 130756 A1 (see above). The only position described therein which relates to the present invention is a substitution at position 217 (corresponding to 211 in *B. lentus* alkaline protease) by any of the 19 amino acids, either alone or in addition to other substitutions which, however, are not relevant to the present application. The same also applies to U.S. Pat. No. 5,801,038. U.S. Pat. No. 5,441,882 describes the method of modifying the enzymic properties via particular single substitutions, including also at position 217 (corresponding to 211 in *B. lentus* alkaline protease), either alone or in addition to other substitutions which, however, are not relevant to the present application. U.S. Pat. No. 4,760,025 discloses corresponding variants which, however, contain in each case only one substitution; included here is again only position 217 and without disclosure of a concrete substitution therefor.

In order to enhance the washing performance of subtilisins, numerous applications pursued the strategy of inserting additional amino acids into the active loops, thus, for example, apart from the already mentioned WO 99/27082 A1, also the applications published with the numbers WO 00/37599 A1, WO 00/37621 A1 to WO 00/37627 A1 and WO 00/71683 A1 to WO 00/71691 A1. Said strategy should accordingly be applicable in principle to all subtilisins belonging to either of the subgroups I-S1 (true subtilisins) or I-S2 (highly alkaline subtilisins).

Another strategy of enhancing the performance is to modify the surface charges and/or the isoelectric point of the molecules, thereby altering their interaction with the substrate. Variations of this kind are introduced, for example, by U.S. Pat. No. 5,665,587 and the applications EP 405901 A1 and WO 91/00334 A1. Numerous positions are mentioned therein, including in each case also 3, 4 and 217 (corresponding to 3, 4 and 211 in *B. lentus* alkaline protease), but without actually disclosing corresponding variants. The application WO 91/00345 A1 also refers to these positions for the same purpose, likewise without actually indicating corresponding variants. WO 92/11348 A1 discloses point mutations for reducing the pH-dependent variation in the molecular charge. This may at most relate to the substitutions S3T and L211D which characterize the present application; however, no relevant substitution is directly disclosed therein. The application WO 00/24924 A2 derives from this principle a method for identifying variants which are supposedly suitable for usage in detergents and cleaning agents; all variants disclosed here have at least one substitution at position 103, preference being given to multiple variants containing no substitution relevant to the present application. According to WO 96/34935 A2, it is also possible to increase the hydrophobicity of the molecules for the purpose of enhancing the performance in detergents and cleaning agents, and this may influence the stability of the enzyme.

The application WO 99/20727 A2 discloses subtilisin variants as may have been obtained by a method of the application WO 00/24924 A2: they all comprise at least one substitution at position 103, combined with a multiplicity of other possible substitutions, none of them, however, at the position corresponding to position 61 of *B. lentus* protease. Preference is given to multiple variants having at least six substitutions, including also positions 205 and 217 (corresponding to 199 and 211 in *B. lentus* alkaline protease); only two of more than 50 of said variants actually have the substitution 199I relevant to the present application. The applications WO 99/20723 A2 and WO 99/20726 A2 disclose the same mutants for detergents and cleaning agents which additionally contain an amylase, or bleach.

A modern direction in enzyme development is to combine, via statistical methods, elements from known proteins related to one another to give novel enzymes having properties which have not been achieved previously. Methods of this kind are also listed under the generic term directed evolution and include, for example, the following methods: the StEP method (Zhao et al. (1998), *Nat. Biotechnol.*, Volume 16, pp. 258-261), random priming recombination (Shao et al., (1998), Nucleic Acids Res., Volume 26, pp. 681-683), DNA shuffling (Semmer, W. P. C. (1994), *Nature*, Volume 370, pp. 389-391) or RACHITT (Coco, W. M. et al. (2001), *Nat. Biotechnol.*, Volume 19, pp. 354-359).

Another, in particular complementary, strategy is to increase the stability of the proteases concerned and thus to increase their efficacy. For example, U.S. Pat. No. 5,230,891 has described stabilization via coupling to a polymer for proteases used in cosmetics; said stabilization is accompanied by enhanced skin compatibility. Especially for detergents and cleaning agents, on the other hand, stabilizations by point mutations are more familiar. Thus, according to U.S. Pat. No. 6,087,315 and U.S. Pat. No. 6,110,884, it is possible to stabilize proteases by replacing particular tyrosine residues with other residues. WO 89/09819 A1 and WO 89/09830 A1 describe relatively thermostable BPN' variants which have at positions 217 (corresponding to 211 in *B. lentus* alkaline protease) substitutions by K or L and, in addition to 217K, the substitution S63D at position 63 (corresponding to position 61).

Other possible examples of stabilization via point mutagenesis, which have been described, are 1) replacing particular amino acid residues with proline according to WO 92/19729 A1, and, respectively, EP 583339 B1 and U.S. Pat.

No. 5,858,757 and according to EP 516200 A1; 2) introducing more polar or more highly charged groups on the molecule surface, according to EP 525610 A1, EP 995801 A1 and U.S. Pat. No. 5,453,372, inter alia at the position corresponding to V4 of *B. lentus* protease; in contrast, the exchange V4I, as in the present application, introduces a less polar amino acid; 3) enhancing the binding of metal ions, in particular via mutagenesis of calcium binding sites, for example according to the teaching of the applications WO 88/08028 A1 and WO 88/08033 A1; or 4) blocking autolysis by modification or mutagenesis, for example according to U.S. Pat. No. 5,543,302.

The application EP 398539 A1 discloses a combination of two or more stabilization strategies. Accordingly, subtilisins may be stabilized and their contribution to the washing or cleaning performance may be improved by (1.) replacing amino acids of the calcium binding sites with more negative ones, (2.) deleting or mutating natural Asn-Gly sequences, (3.) replacing Met residues with other residues and (4.) additionally substituting particular amino acids close to the catalytic center. None of the first three possibilities applies to the variants of the invention of the present application. The fourth possibility relates to positions 61 and 211. Here it is suggested, however, to replace the amino acids naturally present at these positions (S63 and Y217 in subtilisin BPN') with G and L, respectively. In contrast, these positions in particular are occupied by amino acids other than G or L in the molecules of the present application.

Further possibilities of stabilizing subtilisins, in particular those derived from that of *Bacillus lentus*, via point mutagenesis are reported in U.S. Pat. No. 5,340,735, U.S. Pat. No. 5,500,364, U.S. Pat. No. 5,985,639 and U.S. Pat. No. 6,136,553. The mutated positions are determined via analysis of the three dimensional structure. Variants at positions 61 and 211, however, are described in none of these documents.

The documents EP 755999 A1 and WO 98/30669 A1, for example, disclose that proteases, in particular performance-enhanced proteases, may be used together with α-amylases and other detergent enzymes in detergents and cleaning agents in order to enhance the washing or cleaning performance. The application WO 97/07770 A1, for example, discloses that some of those which have previously been established as detergent proteases (see below) are also suitable for cosmetic purposes. The application EP 380362 A1, for example, introduces another possible use of proteases, which relates to organochemical syntheses for which, according to said application, those subtilisins should be suitable which have been stabilized via point mutagenesis at, according to *B. lentus* alkaline protease numbering, positions 61 (by mutation to D) and/or 211 (by mutation to K or L), either alone or in addition to other mutations. Thus, in this connection too, no substitution relevant to the present invention has been described previously.

The *B. lentus* alkaline proteases are highly alkaline proteases of *Bacillus* species. According to the application WO 91/02792 A1, one of these strains has been deposited under number DSM 5483; the sequences and biochemical properties of the wild-type enzyme are also disclosed therein. WO 92/21760 A1 and WO 95/23221 A1 disclose variants of this enzyme, to be obtained by point mutation and suitable for use in detergents and cleaning agents.

The wild-type enzyme is derived from a producer which had originally been obtained by screening for alkaliphilic *Bacillus* strains and displayed itself a comparatively high stability to oxidation and the action of detergents. The applications WO 91/02792 A1 and, respectively EP 493398 B1 and U.S. Pat. No. 5,352,604 describe its heterologous expression in the host *Bacillus licheniformis* ATCC 53926. The claims of said US patent refer to positions 208, 210, 212, 213 and 268 as being characteristic for *B. lentus* alkaline protease; said positions correspond to positions 97, 99, 101, 102 and 157 in the numbering of the mature protein, in which positions this enzyme differs from the mature Savinase®. The three dimensional structure of this enzyme is described in the publication Goddette et al. (1992), *J. Mol. Biol.*, Volume 228, pp. 580-595: "The crystal structure of the *Bacillus lentus* alkaline protease, Subtilisin BL, at 1.4 Å resolution".

The application WO 92/21760 A1, or U.S. Pat No. 5340735, also discloses the amino acid sequence, under SEQ ID No. 52 therein, and the nucleotide sequence, under SEQ ID No. 106 therein, of the *B. lentus* alkaline protease wild-type enzyme produced by B. lentus DSM 5483. In addition, this application discloses 51 different variants derived from said protease, which differ from the wild type in single or in each two or more positions from the wild type and which thereby have been stabilized. Said variants also include the substitutions S3T, V4I and VI 199I. According to this application, most preference is given to the variant M131 containing the substitutions S3T/V4I/A188P/V193M/V199I which has been deposited under the reference ATCC 68614 with the American Type Culture Collection, 10801 University Boulevard, Manassas, Va. 20110-2209, USA. This variant serves as starting enzyme for the present application (see Example 1) and its DNA sequence and amino acid sequence are also indicated in the sequence listing under SEQ ID Nos 1 and 2, respectively. All of these variants are thus derived from *Bacillus lentus* DSM 5483 alkaline protease. The US patents U.S. Pat. No. 5,500,364 and U.S. Pat. No. 5,985,639 derived from the WO document, for example, disclose variants whose stability has been enhanced by point mutations at different positions.

The application WO 95/23221 A1 reveals *B. lentus* alkaline protease variants whose performance for usage in detergents and cleaning agents has been enhanced by specific point mutagenesis and which are to be considered as further developments of the aforementioned molecules. Some of those likewise have the three substitutions S3T, V4I and V199I. In addition, they all have two or three further point mutations compared to the wild-type enzyme from *B. lentus* DSM 5483. Some of them carry an additional mutation at position 211, namely 211D (variant F49, F54 and F55). Consequently, said application, and the corresponding U.S. Pat. No. 5,691,295, U.S. Pat. No. 5,801,039 and U.S. Pat. No. 5,855,625 claim variants containing the substitutions 211D and 211E. U.S. Pat. No. 6,197,589 illustrates the corresponding strategy, namely to specifically modify the charge conditions close to the substrate binding pocket.

As all of these studies which have been carried out over a long period of time confirm, there is high demand for technically useable proteases some of which differ drastically, some only in a few positions, from previously known proteases. They cover thus a broad spectrum of very drastic, down to very subtle performance differences. This is evident especially in their use in detergents and cleaning agents. During their development, the behavior of said enzymes, for example in the context of a detergent or cleaning agent formulation, cannot be readily inferred from the possibly calculable enzymic properties. Other factors such as stability toward high temperatures, oxidizing agents, denaturation by surfactants, folding effects or desired synergies with other ingredients play a part here and can frequently be determined only experimentally.

SUMMARY

The present invention provides protease variants having alanine, valine, leucine, isoleucine, cysteine, methionine, phenylalanine, tyrosine, tryptophan, threonine, histidine, lysine, or arginine at an amino acid residue position corresponding to position 61 of *Bacillus lentus* subtilisin.

These and other aspects of the invention, including methods for preparing the variants, as well as proteins, nucleic acids, vectors, cells, for production of the variants, and agents comprising the variants, will become more apparent from the detailed description and claims.

BRIEF DESCRIPTION OF THE DRAWINGS

FIG. 1 is an amino acid sequence alignment of the *B. lentus* alkaline protease variant of the invention with the most important known subtilisins, in each case in the mature, i.e. processed, form, in which:

Figure 2:
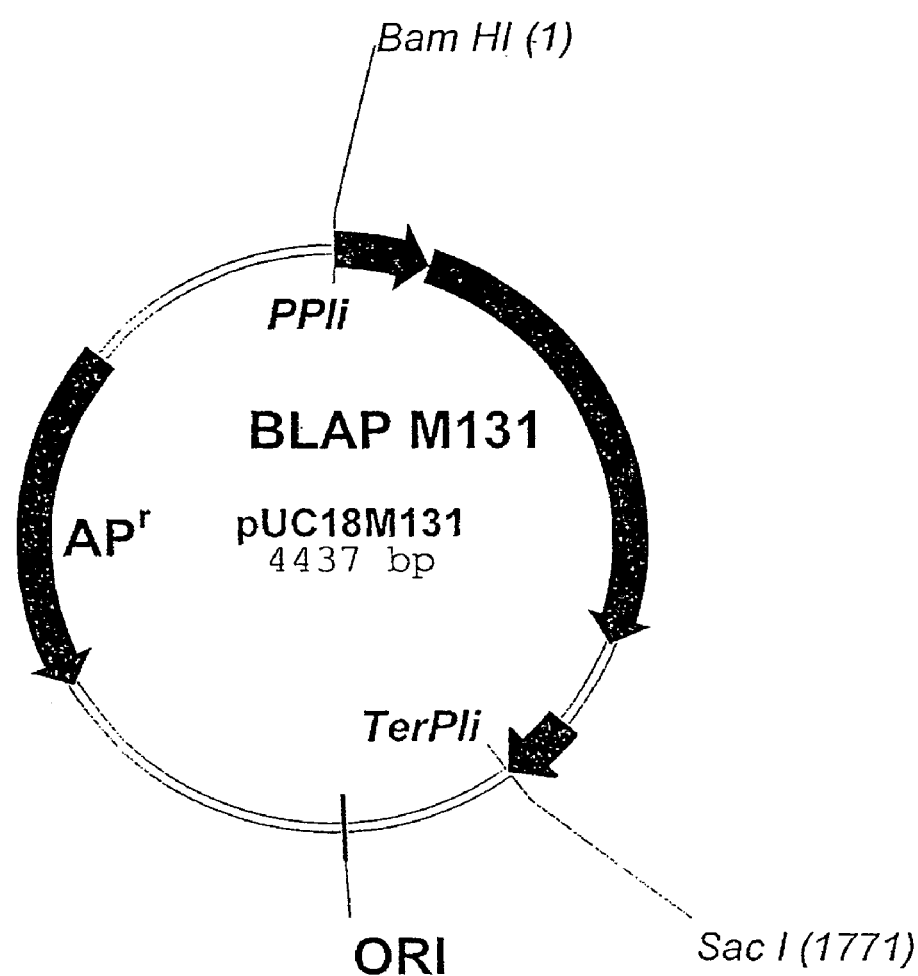

S3T/V4I/G61A/V199I is inventive *B. lentus* alkaline protease variant (SEQ ID NO: 15)

S3T/V4I/G61A/V199I/L211D is inventive *B. lentus* alkaline protease variant (SEQ TD NO:16)

Subtilisin 309 is *Bacillus lentus* subtilisin according to WO 89/06279 A1 (SEQ ID NO:17)

Subtilisin PB92 is *Bacillus* nov. spec. 92 subtilisin according to EP 283075 A2 (SEQ ID NO:18)

Subtilisin Carlsberg is *Bacillus lichenformis* subtilisin according to E.L. Smith et al., *J. Biol. Chem., Volume* 243, pp. 2184-2191 (SEQ ID NO:19)

Subtilisin BPN' is *Bacillus amyloliquefaciens* subtilisin according to J.A. Wells et al. (1983), Nucleic Acids Research, Volume 11, pp. 7911-7925 (SEQ ID NO:20)

Consensus is positions corresponding in the majority of the sequences indicated (SEQ ID NO:21).

FIG. 2 is the mutagenesis vector pUC18M131, wherein the Bam HI-Sac I fragment depicted in SEQ ID No. 1 extends therein over positions 1 to 1771; the remaining vector regions are identical to those of the starting plasmid pUC18 (Amersham Pharmacia Biotech, Freiburg, Germany). For reasons of clarity, further unique cleavage sites are not shown.

DETAILED DESCRIPTION

It was the object of the present invention to find subtilisins which show improved performances in technical applications. In particular, it was intended to find those subtilisins which improve the washing or cleaning performance of detergents and/or cleaning agents. Part of the object was not only to improve the proteases with respect to their hydrolytic activity but also to maintain their stability in appropriate formulations.

Further parts of the object were to provide nucleic acids coding for proteases of this kind and to provide vectors, host cells and preparation methods which may be utilized for obtaining proteases of this kind. It was further intended to provide corresponding agents, in particular detergents and cleaning agents, corresponding washing and cleaning methods and also corresponding possible uses for proteases of this kind. Finally, it was intended to define possible technical uses for the proteases found.

Surprisingly, it was found that replacing the amino acid glycin at position 61 with a different amino acid, in particular with an aliphatic amino acid and very particularly with alanine results in an increased washing performance contribution. This effect benefits from the contributions of other substitutions such as that by isoleucine at position 199 and/or other defined amino acid residues such as aspartic acid at position 211, presumably via an enzymic effect. This increased efficacy is enhanced, presumably via a stabilizing effect, by the amino acids threonine and isoleucine at positions 3 and 4, respectively.

According to the invention, this object is thus achieved by alkaline proteases of the subtilisin type, which are characterized in that, according to the numbering of *Bacillus lentus* subtilisin, they have, compared with the starting enzyme, a substitution by any of the amino acids alanine, valine, leucine, isoleucine, cysteine, methionine, phenylalanine, tyrosine, tryptophan, threonine, histidine, lysine and arginine, preferably by any of the amino acids alanine, valine, leucine and isoleucine, particularly preferably by alanine, at position 61.

Increasing preference is given to those solutions in which an isoleucine is present at position 199, in addition to the substitution at position 61; those in which any of the amino acids defined above is present at position 61, isoleucine is present at position 199, aspartic acid is present at position 211 and, for stabilization, threonine is present at 3 and/or isoleucine is present at position 4. Particularly preferred solutions are those proteases which are derived from *B. lentus* alkaline protease, in particular either of the two variants *B. lentus* alkaline protease S3T/V4I/G61A/V199I or *B. lentus* alkaline protease S3TN4I/G61A/V199I/L211D. This subject matter of the invention also comprises developments and derivatives of said proteases.

The parts of the object are achieved by providing with the present invention nucleic acids coding for proteases of the invention and also vectors, host cells and preparation methods, all of which are in each case separate subject matters of the invention and can be utilized for obtaining proteases of this kind. Also provided are corresponding agents, in particular detergents and cleaning agents, corresponding washing and cleaning methods and also corresponding possible uses for proteases of this kind. Finally, possible technical uses for the proteases found are defined.

A protein means in accordance with the present application a polymer which is composed of the natural amino acids, has a substantially linear structure and usually adopts a three dimensional structure to exert its function. The present application refers to the 19 proteinogenic, naturally occurring L-amino acids by the internationally used 1- and 3-letter codes.

The combination of any of these names with a number indicates the amino acid residue which the particular protein carries at the respective position. Thus, for example, S3 indicates a serine residue at position 3, starting with the numbering at the N terminus of the protein in question. According to this nomenclature, a point mutation at this site, for example to give the amino acid threonine, is abbreviated with S3T. In order to indicate variants having a plurality of point mutations, these substitutions are separated from one another by forward slashes. Accordingly, the variant S3T/V4I is characterized in that the serine previously present at position 3 of said variant has been replaced with a threonine and the valine at position 4 has been replaced with an isoleucine.

Unless stated otherwise, the positions indicated in the present invention refer to the in each case mature forms of the proteins concerned, i.e. without the signal peptides (see below).

An enzyme in accordance with the present application means a protein which exerts a particular biochemical function. Proteolytic enzymes or enzymes with proteolytic function, for example, mean generally those which hydrolyze the acid amide bonds of proteins, in particular those bonds located inside the proteins, and which may therefore also be referred to as endopeptidases. Subtilisin proteases are those endopeptidases which are naturally produced by Gram-positive bacteria and usually secreted or which are derived from the latter, for example via molecular-biological methods, and can be homologized with the natural subtilisin proteases via part regions such as structure-forming or function-carrying regions. They are described, for example, in the paper "Subtilases: Subtilisin-like Proteases" by R. Siezen, pages 75-95 in "Subtilisin enzymes", edited by R. Bott and C. Betzel, New York, 1996.

Numerous proteins are formed as "preproteins", i.e. together with a signal peptide. This then means the N-terminal part of the protein, whose function usually is to ensure the export of the protein produced from the producing cell into the periplasm or into the surrounding medium and/or the correct folding thereof. Subsequently, the signal peptide is removed from the remaining protein under natural conditions by a signal peptidase so that said protein exerts its actual catalytic activity without the initially present N-terminal amino acids. According to FIG. 1 in WO 91/02792 A1, the preprotein of *Bacillus lentus* DSM 5483 subtilisin contains 380 amino acids; the mature protein, however, contains only 269; the numbering starts with the first amino acid of the mature protein, i.e. in this case with the alanine which would have number 112 according to the preprotein sequence. According to SEQ ID No. 1 of the present application, the signal peptide of *B. licheniformis* ATCC 68614 subtilisin is 111 amino acids and the mature peptide is 269 amino acids in length. Without this division, the complete protein is 380 amino acids in length, as SEQ ID No. 2 reveals. According to the sequence listing, the same also applies to the particularly preferred embodiments.

Owing to their enzymic activity, preference is given for technical applications to the mature peptides, i.e. the enzymes processed after their preparation, over the preproteins.

Pro-proteins are inactive precursors of proteins. The precursors of the former containing a signal sequence are referred to as prepro-proteins.

The term "antibody" is intended to encompass both polyclonal and monoclonal antibodies, as well as a functional fragment thereof (e.g., an antigen-binding fragment). Preparation of immunizing antigen, and polyclonal and monoclonal antibody production are well known to those skilled in the art, and can be achieved with a variety of well known techniques.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids according to aspects of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

Nucleic acids are compounds naturally composed of nucleotides, serve as information carriers and code for the linear amino acid sequence in proteins or enzymes. For molecular-biological work, preference is given to the nucleic acid DNA as the naturally more durable information carrier. In contrast, an RNA is produced to implement the invention in a natural environment such as, for example, in an expressing cell, and RNA molecules important to the invention are therefore likewise embodiments of the present invention.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "oligonucleotide," as used herein refers to sequences, primers and probes according to aspects of the present invention, and is defined as a nucleic acid molecule comprised of two or more ribo or deoxyribonucleotides, preferably more than three. The exact size of the oligonucleotide will depend on various factors and on the particular application and use of the oligonucleotide.

In accordance with the present application, the information unit of a nucleic acid, which corresponds to a protein, is also referred to as gene. In the case of DNA, the sequences of both complementary strands in in each case all three possible reading frames must be taken into account. The fact that different codon triplets can code for the same amino acids so that a particular amino acid sequence can be derived from a plurality of different nucleotide sequences which possibly only have low identity must also be taken into account (degeneracy of the genetic code). Moreover, various organisms differ in the use of these codons. For these reasons, both amino acid sequences and nucleotide sequences must be incorporated into the scope of protection, and nucleotide sequences indicated are in each case to be regarded only as coding by way of example for a particular amino acid sequence.

It is possible for a skilled worker, via nowadays generally known methods such as, for example, chemical synthesis or polymerase chain reaction (PCR) in combination with molecular-biological and/or protein-chemical standard methods, to prepare complete genes on the basis of known DNA sequences and/or amino acid sequences. Methods of this kind are known, for example, from the "Lexikon der Biochemie" [encyclopedia of biochemistry], Spektrum Akademischer Verlag, Berlin, 1999, Volume 1, pp. 267-271 and Volume 2, pp. 227-229. This is possible, in particular, if a strain deposited with a strain collection can be used. Using PCR primers which have been synthesized on the basis of a known sequence, it is possible to synthesize, clone and, if desired, further process the genes in question from such strains without any problems. This further process includes, for example, site-directed or random mutagenesis.

Changes of the nucleotide sequence, such as those which may be produced, for example, by molecular-biological methods known per se, are referred to as mutations. Depending on the type of change, deletion, insertion or substitution mutations, for example, or those in which various genes or parts of genes are fused to one another (shuffling) are known; these are gene mutations. The corresponding organisms are referred to as mutants. The proteins derived from mutated nucleic acids are referred to as variants. Thus, for example, deletion, insertion, substitution mutations or fusions result in deletion-, insertion-, substitution-mutated or fusion genes and, at the protein level, in corresponding deletion, insertion or substitution variants, or fusion proteins.

Vectors mean in accordance with the present invention elements which consist of nucleic acids and which comprise a gene of interest as characteristic nucleic acid region. They are capable of establishing said gene as a stable genetic element replicating independently of the remaining genome in a species or a cell line over several generations or cell divisions. Vectors are, in particular when used in bacteria, special plasmids, i.e. circular genetic elements. Genetic engineering distinguishes between, on the one hand, those vectors which are used for storage and thus, to a certain extent, also for genetic engineering work, the "cloning vectors", and, on the other hand, those which perform the function of establishing the gene of interest in the host cell, i.e. enabling expression of the protein in question. These vectors are referred to as expression vectors.

Homologization, i.e. comparison with known enzymes, as carried out via an alignment, for example, makes it possible to deduce the enzymic activity of an enzyme studied from the amino acid or nucleotide sequence. Said activity may be modified qualitatively or quantitatively by other regions of the protein which are not involved in the actual reaction. This could concern, for example, enzyme stability, activity, reaction conditions or substrate specificity.

The term proteolytic enzyme or protease therefore means, in addition to the functions of the few amino acid residues of the catalytically active site, any functions as resulting from the action of the entire remaining protein or one or more parts of the remaining protein on the actually catalytically active regions. In accordance with the invention, such modifying functions or part activities alone are also regarded as proteolytic activity, as long as they support a proteolytic reaction. Such auxiliary functions or part activities include, for example, binding of a substrate, an intermediate or an end product, the activation or inhibition or mediation of a regulating influence on the hydrolytic activity. Another possible example is the formation of a structural element located far away from the active site. The second precondition for the fact that it is a proteolytic protein of the invention, however, is that the chemical behavior of the actually active residues alone or, in addition, the action of the modifying parts results in a hydrolysis of peptide bonds. It is furthermore possible that one or more parts of, for example, the protein of the invention also modify qualitatively or quantitatively the activities of other proteases. This influencing of other factors is likewise regarded as proteolytic activity. Proteolytically active enzymes are also those whose activity at a given point in time is blocked, for example by an inhibitor. Their principle suitability for the corresponding proteolytic reaction is crucial.

Fragments mean any proteins or peptides which are smaller than natural proteins or those which correspond to completely translated genes, and may also be obtained synthetically, for example. Owing to their amino acid sequences, they may be related to the corresponding complete proteins. They may adopt, for example, identical structures or exert proteolytic activities or part activities such as complexing of a substrate, for example. Fragments and deletion variants of starting proteins are very similar in principle; while fragments represent rather relatively small pieces, the deletion mutants rather lack only short regions and thus only individual partial functions.

Chimeric or hybrid proteins mean in accordance with the present application those proteins which are composed of elements which naturally originate from different polypeptide chains from the same organism or from different organisms. This procedure is also called shuffling or fusion mutagenesis. The purpose of such a fusion may be, for example, to cause or to modify an enzymic function with the aid of the fused-to protein part of the invention. In accordance with the present invention, it is unimportant as to whether such a chimeric protein consists of a single polypeptide chain or of a plurality of subunits between which different functions may be distributed. To implement the latter alternative, it is possible, for example, to break down a single chimeric polypeptide chain into a plurality of polypeptide chains by a specific proteolytic cleavage, either posttranslationally or only after a purification step.

Proteins obtained by insertion mutation mean those variants which have been obtained via methods known per se by inserting a nucleic acid fragment or protein fragment into the starting sequences. They should be classified as chimeric proteins, due to their similarity in principle. They differ from the latter merely in the size ratio of the unaltered protein part to the size of the entire protein. The proportion of foreign protein in such insertion-mutated proteins is lower than in chimeric proteins.

Inversion mutagenesis, i.e. a partial sequence conversion, may be regarded as a special form of both deletion and insertion. The same applies to a regrouping of various molecule parts, which deviates from the original amino acid sequence. Said regrouping can be regarded as deletion variant, as insertion variant and also as shuffling variant of the original protein.

Derivatives mean in accordance with the present application those proteins whose pure amino acid chain has been chemically modified. Those derivatizations may be carried out, for example, biologically in connection with protein biosynthesis by the host organism. Molecular-biological methods may be employed here. However, said derivatizations may also be carried out chemically, for example by chemical conversion of an amino acid side chain or by covalent binding of another compound to the protein. Such a compound may also be, for example, other proteins which are bound, for example, via bifunctional chemical compounds to proteins of the invention. Modifications of this kind may influence, for example, substrate specificity or strength of binding to the substrate or may cause transient blocking of the enzymic activity if the coupled-to substance is an inhibitor. This may be useful for the period of storage, for example. Likewise, derivatization means covalent binding to a macromolecular support.

In accordance with the present invention, all enzymes, proteins, fragments and derivatives, unless they need to be explicitly referred to as such, are included under the generic term proteins.

The performance of an enzyme means its efficacy in the technical area considered in each case. Said performance is based on the actual enzymic activity but, in addition, depends on further factors relevant to the particular process. These include, for example, stability, substrate binding, interaction with the material supporting the substrate or interactions with other ingredients, in particular synergies.

The washing or cleaning performance of an agent means in accordance with the present application the effect exerted by the agent studied on the soiled articles, for example textiles or objects with hard surfaces. Individual components of such agents, for example individual enzymes, are evaluated with respect to their contribution to the washing or cleaning performance of the entire agent, for it is not readily possible to deduce the contribution of an enzyme to the washing performance of an agent from the enzymic properties of said enzyme. Examples of other factors which play a part here are stability, substrate binding, binding to the material to be cleaned and interactions with other ingredients of the said agents, in particular synergies in removing the soils.

With respect to the stated object, the present patent application has pursued the strategy of further improving Bacillus lentus DSM 5483 subtilisin, in particular compared to the molecules disclosed in the applications WO 91/02792 A1, WO 92/21760 A1 and WO 95/23221 A1, and very particularly compared to variants M131 S3T/V4I/A188P/V193M/V199I and F49 S3T/V4I/A188P/V193M/V199I/L211D, for usage in detergents and cleaning agents. The corresponding technical teaching can be applied accordingly also to other, in particular closely related proteases, very particularly of the subtilisin type.

Particularly important to the invention are positions 3, 4, 61, 199 and 211 of the mature proteins according to the Bacillus lentus DSM 5483 subtilisin numbering (WO 92/21760 A1). These can be homologized according to Table 1 with those of the most important subtilisins; said homologization can be transferred to all other subtilisins. Thus, for example, the paper "Subtilases: Subtilisin-like Proteases" by R. Siezen, pages 75-95 in "Subtilisin enzymes", edited by R. Bott and C. Betzel, New York, 1996, shows an alignment of more than 20 subtilisins in relation to the known sequence of subtilisin BPN'. Table 1 shows homologization of the five positions particularly important to the invention.

question. In particular, it can be expected, owing to the teaching of the present patent application, that those subtilisins which have already been developed in the prior art with regard to their usage in detergent and cleaning agents can be improved further with respect to their contributions to the washing and cleaning performances by adopting said point mutations.

In the prior art (see above), substitutions by the amino acids N, D, Q, E, P and S, in particular in combination with other point mutations not relating to the present invention, have been described for position 61 according to the numbering of B. lentus alkaline protease. Substitutions by the neutral amino acid threonine which contains a hydroxyl group, by the basic amino acids histidine, lysine, arginine, by the aromatic amino acids phenylalanine, tyrosine, tryptophan, by the sulfur-containing amino acids cysteine, methionine and by the aliphatic amino acids alanine, valine, leucine, isoleucine have not been described previously, in particular not with the aim of improving thereby the performance of the enzyme, that is particularly its contribution to the washing or cleaning performance of a corresponding agent. This is achieved by the present patent application.

According to the present invention, the performance-enhancing substitution at position 61 is preferably a substitution by an aliphatic amino acid, namely alanine, valine, leucine or isoleucine, particularly preferably by alanine, for this characterizes the variants studied in the examples, B. lentus alkaline protease S3T/V4I/G61A/V199I and B. lentus alkaline protease S3T/V4I/G61A/V199I/L211D. For surprisingly it was found that replacing the amino acid glycine at position 61 with a different amino acid, in particular with an aliphatic amino acid and very particularly with alanine, results in an increased washing performance contribution.

The variant of a Bacillus lentus subtilisin, which may be regarded as having the highest degree of homology to the variant of the invention, B. lentus alkaline protease S3T/V4I/G61A/V199I/L211D, is the B. lentus alkaline protease variant F49, disclosed in WO 95/23221 A1, which has the characterizing substitutions S3T/V4I/A188P/V193M/

TABLE 1

| Reference enzymes | Numbering according to the sequences in | Pos. 3 | Pos. 4 | Pos. 61 | Pos. 199 | Pos. 211 |
|---|---|---|---|---|---|---|
| B. lentus alkaline protease | WO 92/21760 A1 | S 3 | V 4 | G 61 | V 199 | L 211 |
| BPN' | Wells et al. (see above) | S 3 | V 4 | S 63 | I 205 | Y 217 |
| Subtilisin Carlsberg | Smith et al. (see above) | T 3 | V 4 | G 62 | V 204 | L 216 |
| PB92 | EP 283075 A2 | S 3 | V 4 | G 61 | V 199 | L 211 |
| Subtilisin 309 | WO 89/06279 A1 | S 3 | V 4 | G 61 | V 199 | L 211 |
| Thermitase | WO 91/00345 A1 | S 10 | R 11 | G 70 | I 209 | L 221 |
| Proteinase K | WO 91/00345 A1 | T 4 | A 6 | G 68 | I 208 | I 220 |

FIG. 1 of the present patent application also depicts an alignment of the amino acid sequences of the B. lentus alkaline protease variants of the invention S3T/V4I/G61A/V199I and S3T/V4I/G61A/V199I/L211D with these most important subtilisins described at the outset, namely subtilisin 309 (Savinase®), subtilisin PB92, subtilisin Carlsberg and subtilisin BPN'.

The transferability of the teaching of the present invention is based on the high structural homologies between the subtilisins and on the substantially identical reaction mechanism. Thus it can be expected that said point mutations act in each case comparably in the context of the molecule in V199I/L211D. Accordingly, the variant which is the next most similar to S3T/V4I/G61A/V199I is the B. lentus alkaline protease variant S3T/V4I/A188P/V193M/V199I disclosed in WO 92/21760 A1 and referred to in WO95/23221 A1 as M131.

Thus, instead of the two substitutions A188P and V193M, the present invention contains in each case a variation in position 61. As, for example, application WO 95/30011 A2 demonstrates, the amino acid 193 of B. lentus subtilisins is located at the start of loop 6, while the amino acid 188 is to be assigned not to any loop but to the compact protein region located in-between. In this respect, both mutations are located in structurally different regions of the molecule. Surprisingly, it was found in the present invention that reversing the two positions 188 and 193 to the amino acids of the wild type and an additional mutation at position 61, i.e. in loop 1, results in an enzyme which is superior to the previously known enzymes, in particular the previously known variants of *B. lentus* alkaline protease, with respect to its washing and cleaning performance. The results shown in Examples 3, 5 and 7, in particular, verify this.

For example, the applications CA2049097 A1, EP 380362 A1 and WO 95/30010 A1 (see above) suggest variations in position 61, but only to acidic amino acids. A series of applications regarding point mutagenesis on subtilisins, including WO 96/28556 A2 and in particular WO 95/30011 A2 (see above), additionally describe for position 61 (naturally glycine in most subtilisins) substitutions of the kinds which mean locally very drastic changes for the molecule and which possibly also influence the substrate interactions exerted by the first loop (N, D, Q, E, P and S). On the other hand, EP 398539 B1 even suggests a mutagenesis which results in the amino acid glycine only being introduced for the first time at this site in the subtilisin in question, while it is naturally present there in *Bacillus lentus* subtilisin. In view of this prior art, it is a surprise that a change especially in this position, in particular to an amino acid having an aliphatic side chain, and very particularly to alanine, has an advantageous effect on the reaction exerted by the enzyme.

It is surprising, from the viewpoint of application, in particular in detergents and cleaning agents, that this results in performance improvement, in particular in an improvement of the contribution of enzymes of this kind to the washing and cleaning performance on various soilings. This is shown in the exemplary embodiments 2 to 7 of the present application.

According to these observations, preference is furthermore given to those variants which, in addition to the substitutions mentioned at position 61, according to the numbering of *Bacillus lentus* subtilisin, have the amino acid isoleucine at position 199. The influence of this substitution on the enzymic properties of *Bacillus lentus* DSM 5483 subtilisin have been described in WO 92/21760 A1, for example.

Further preference is given to alkaline proteases of the subtilisin type, which are characterized in that they have, according to the numbering of *Bacillus lentus* subtilisin, isoleucine at position 199, aspartic acid at position 211 and any of the amino acids alanine, valine, leucine, isoleucine, cysteine, methionine, phenylalanine, tyrosine, tryptophan, threonine, histidine, lysine and arginine, preferably alanine, valine, leucine or isoleucine, particularly preferably alanine, at position 61. This relates to both natural molecules and molecules obtained by mutagenesis which contain said amino acids at said positions.

The contribution of the amino acid residue aspartic acid at position 211 to the increase in washing or cleaning performance of a corresponding agent is revealed, for example, in Example 10 of the application WO 95/23221 A1.

Alkaline proteases of the invention are preferably characterized in that they have at least one stabilization, since this increases their stability during storage and/or during their use so that the advantageous action of the aforementioned amino acids and, respectively, amino acid substitutions is prolonged and thus enhanced.

The stability of proteases of the invention may be increased by coupling to polymers, for example. A method of this kind is described in U.S. Pat. No. 5,230,891, for example. It requires linking the proteins, prior to their use in appropriate agents, via a chemical coupling step to such polymers.

Preference is given to stabilizations possible via point mutagenesis of the molecule itself, since they do not require any further working steps following obtainment of the protein. Some point mutations suitable for this are known per se from the prior art. Thus, according to U.S. Pat. No. 6,087,315 and U.S. Pat. No. 6,110,884, proteases may be stabilized by replacing particular tyrosine residues with other residues. Applied to *Bacillus lentus*-derived proteins of the invention, this would mean substitutions of the tyrosine residues at positions 89, 161, 165, 208 and 257, according to SEQ ID No. 2; the other two positions indicated there are already occupied by tyrosine anyway in *B. lentus* alkaline protease.

Other possibilities are, for example:
replacing particular amino acid residues with proline, according to EP 583339 B1; this would mean for enzymes derived from *B. lentus* the substitutions S55P, A96P, A166P, A188P and/or S253P);
introducing more polar or more highly charged groups on the surface of the molecule, according to EP 995801 A1;
altering the binding of metal ions, in particular the calcium binding sites, for example according to the teaching of the applications WO 88/08028 A1 and WO 88/08033 A1. According to the first of these documents, one or more of the amino acid residues involved in calcium binding would have to be replaced with negatively charged amino acids. According to the publication by D. W. Goddette et al. (1992) in *J. Mol. Biol.*, Volume 228, pages 580-595, *Bacillus lentus* subtilisin has the following two calcium binding sites: Ca1 (with high binding affinity), comprising positions 2 Q(s), D40 (s, 2×), L73*, N75 (m), 177 (s), V79 (m) and the site Ca3 (with low binding affinity), comprising positions A168, A163, Y165, water 273, 317; in each case according to the numbering of *Bacillus lentus* subtilisin.
according to the teaching of the application WO 88/08033 A1, point mutations would have to be introduced simultaneously in at least one of the sequences of the two residues arginine/glycine for stabilization via calcium binding; this relates, for example in *Bacillus lentus* subtilisins, to the NG sequences in positions 60/61, 115/116 and 212/213.
according to U.S. Pat. No. 5,453,372, proteins may be protected by particular mutations on the surface against the effect of denaturating agents such as surfactants; the positions indicated there correspond to positions 134, 155, 158, 164, 188 and/or 189 in *B. lentus* alkaline protease.

Further comparable possibilities are indicated in U.S. Pat. No. 5,340,735, U.S. Pat. No. 5,500,364, U.S. Pat. No. 5,985,639 and U.S. Pat. No. 6,136,553.

A preferred stabilization of this kind for alkaline proteases of the invention is that due to the amino acid threonine at position 3 according to the numbering of *Bacillus lentus* subtilisins, since, for example, Table 3 of the application WO 92/21760 A1 reveals that this substitution stabilizes the molecule both with respect to increased temperature and with respect to the action of surfactants, in comparison with the wild-type enzyme. The N terminus of the molecule, which includes positions 3 and 4, is located, after processing, on the surface, more precisely at the end of the cleft containing the active site. This loose end is connected to the rest of the molecule in particular via noncovalent interactions and thus contributes to maintaining the globular structure. It can be assumed, without being bound to this theory, that any mutations which limit the flexibility of said loose end contribute to the stability of the entire molecule.

A preferred stabilization of this kind for alkaline proteases of the invention is also that due to the amino acid isoleucine at position 4 according to the numbering of *Bacillus lentus* subtilisin. The stabilizing action of this substitution is likewise revealed in Table 3 of the application WO 92/21760 A1.

Particularly preferably, the molecule is stabilized and its performance profile is modified via both the substitution by threonine at position 3 and the substitution by isoleucine at position 4.

Corresponding subtilisins of the invention exhibited, in the examples of the present application, performance increases in corresponding detergent or cleaning agent formulations, compared to the enzyme Savinase® known from the prior art, which does not have this stabilization. It might be assumed, without being bound to this theory, that the stability of the variants concerned contributes to maintaining the activity of said enzymes in the wash liquor for a sufficiently long period and thus supporting the improved performance.

In addition, each of these substitutions may also improve in a different way the performance of the molecule, in particular in detergents and cleaning agents, for example via interaction with a substrate or with another ingredient of corresponding agents.

Particular preference is given to the embodiments in which the alkaline protease of the invention is characterized in that it has, according to the numbering of *Bacillus lentus* subtilisin, threonine at position 3, isoleucine at position 4, alanine at position 61 and isoleucine at position 199.

The contribution of a variant of this kind to the washing or cleaning performance of a corresponding agent is documented in the Examples 3, 5 and 7 of the present application.

Very particular preference is given to the embodiments in which the alkaline protease of the invention is characterized in that it has, according to the numbering of *Bacillus lentus* subtilisin, threonine at position 3, isoleucine at position 4, alanine at position 61, isoleucine at position 199 and aspartic acid at position 211.

The contribution of a variant of this kind to the washing or cleaning performance of a corresponding agent is documented in Examples 2, 4 and 6 of the present application.

Variants of this kind are preferably derived from a bacillar subtilisin, in particular from *Bacillus lentus* subtilisin.

Bacillar proteases have from the outset favorable properties for various possible technical uses. These include a certain stability to increased temperature, oxidizing or denaturing agents. Moreover, most experience has been obtained with microbial proteases with respect to their biotechnological production, concerning, for example, the construction of suitable cloning vectors, the selection of host cells and fermentation conditions or the evaluation of risks such as allergenicity, for example.

Especially *Bacillus lentus* subtilisins and subtilisins derived from the naturally produced proteases thereof are established in the prior art, for example for usage in detergents and cleaning agents. They include the proteases mentioned at the outset, subtilisin 147, subtilisin 309 and *B. lentus* alkaline protease. The amount of knowledge obtained for preparation and use of these proteases benefits further inventive developments of these enzymes, including, for example, their compatibility with other chemical compounds such as ingredients of detergents or cleaning agents, for example.

A suitable starting strain which may be used for this is the *B. lentus* strain deposited under the deposition number DSM 5483 with the Deutsche Sammlung von Mikroorganismen und Zellkulturen GmbH, Mascheroder Weg 1b, 38124 Braunschweig, Germany (http://www.dsmz.de) and described, for example, in the applications WO 91/02792 A1, WO 92/21760 A1 and WO 95/23221 A1. It is possible to prepare from this or from related strains such variants by applying molecular-biological standard methods such as, for example, PCR and point mutagenesis methods known per se.

The particularly preferred variants described in the examples have been derived via the procedure illustrated in Example 1 from *B. lentus* alkaline protease of B. lentus which has been deposited under the reference ATCC 68614 with the American Type Culture Collection, 10801 University Boulevard, Manassas, Va. 20110-2209, USA. The nucleotide sequence and the amino acid sequence of this enzyme are disclosed in the sequence listing of the present application under SEQ ID No. 1 and 2, respectively.

This sequence may be used, for example, for constructing primers in order to prepare from DNA preparations of Gram-positive bacteria, preferably Gram-positive bacteria such as *Bacillus lentus*, for example, to modify, where appropriate according to methods known per se, to mutagenize, for example by applying the teaching of the present application, and to express a nucleic acid coding for such a protease. Owing to the degeneracy of the genetic code, in addition numerous other nucleic acids are conceivable which likewise code for said variant and represent equally preferred alternatives within this subject matter of the invention.

This includes, in particular, the *B. lentus* alkaline protease S3T/V4I/G61A/V199I according to the nucleotide sequence indicated in the sequence listing under SEQ ID No. 3, but especially according to the amino acid sequence indicated under SEQ ID No. 4, since the improved washing performance contribution thereof is proved by the corresponding application examples of the present application.

Preference is also given according to the comments above to an alkaline protease which is characterized in that it is a subtilisin derived from *Bacillus lentus* DSM 5483 subtilisin or from the ATCC 68614 subtilisin indicated in SEQ ID No. 2, in particular the *B. lentus* alkaline protease S3T/V4I/G61A/V199I/L211D according to the amino acid sequence indicated in SEQ ID No. 6, and, respectively, the nucleotide sequence indicated in SEQ ID No. 5.

This protease showed, in experiments as described in the application examples of the present application, the greatest improvement in performance in comparison with the comparative molecules. It may be obtained as described above.

A preferred embodiment is a protein derived from any of the above-described proteases, in particular by fragmentation or deletion mutagenesis, by insertion mutagenesis, by substitution mutagenesis or by fusion of at least one part with at least one other protein.

Methods of this kind are established in the prior art. Appropriate molecular-biological methods are also discussed in detail, for example, in the textbook Sambrook and Maniatis "Molecular cloning: a laboratory manual", Cold Spring Harbour Laboratory Press, New York, 1989.

Examples here include variants to which additional properties have been imparted via substitution mutagenesis or via further point mutations and which are, due to said additional properties, predestined with respect to specific possible uses, for example due to changes in surface charges, as disclosed in WO 00/36069 A1, or due to alterations in the loops involved in catalysis or substrate binding, as disclosed in WO 99/27082 A1, for example. It is also possible to subject larger partial regions of said variants to mutagenesis. Thus it may be the aim of fragment generation or deletion mutagenesis, for example, to select specific partial functions of the protease or, on the other hand, to exclude them, for example substrate binding and the interactions with other compounds, exerted via particular regions of the molecule.

Insertion, substitution or fusion may provide proteases of the invention with additional functions. Conceivable in this context is, for example, coupling to particular domains, such as binding to cellulose-binding domains, as described in the publications WO 99/57154 A1 to WO 99/57157 A1, for example. The amino acid linkers described herein may be constructed by forming an integrated fusion protein of protease, linker region and binding domain. Such a binding domain could also come from the same or a different protease, for example in order to enhance binding of the protein of the invention to a protease substrate. This increases the local protease concentration, which increase may be advantageous in individual applications, for example in the treatment of raw materials.

According to another embodiment, the protein of the invention is characterized in that it is additionally derivatized.

This serves in particular for optimization for their particular application purpose. This includes chemical modifications as described, for example, in application DE 4013142 A1. They may also be modified, for example, by coupling of low or high molecular weight chemical compounds, as carried out naturally by various organisms in connection with protein biosynthesis, such as, for example, binding of a fatty acid radical close to the N terminus or glycosylations in the synthesis by eukaryotic host cells. Proteolytic enzymes or fragments which are additionally derivatized are thus embodiments of the present invention.

In connection with the use of proteins of the invention in detergents or cleaning agents, coupling to other detersive substances or enzymes, for example, is particularly useful. The patent applications WO 00/18865 A1 and WO 00/57155 A1, for example, describe comparable coupling approaches for cellulose-binding domains. Analogously, couplings to macromolecular compounds such as, for example, polyethylene glycol may also be carried out in order to modify the molecule with respect to further properties such as stability or skin compatibility. U.S. Pat. No. 5,230,891, for example, describes a modification of this kind for rendering the proteases in question more suitable for use in cosmetics.

Derivatives of proteins of the invention can, in the broadest sense, also mean preparations of these enzymes. Depending on its obtainment, workup or preparation, a protein may be associated with various other substances, for example from the culture of the producing microorganisms, since culture supernatants of protease-producing microorganisms already exhibit a proteolytic activity, indicating that even crude extracts may be used appropriately, for example for inactivating other proteinogenic activities.

A protein may also have been specifically admixed with particular other substances, for example to increase its storage stability. Therefore, any preparations of the actual protein of the invention are also in accordance with the invention. This is also independent of whether or not it actually produces said enzymic activity in a particular preparation, since it may be desired that it has only low activity, if any, during storage and produces its proteolytic function only when used. This may depend, for example, on the folding state of the protein or may result from the reversible binding of one or more accompanying substances of the preparation to a protein of the invention. The joint preparation of proteases with protease inhibitors, in particular, is known from the prior art (WO 00/01826 A2). Also included here are fusion proteins in which the inhibitors are bound via linkers, in particular amino acid linkers, to the particular proteases (WO 00/01831 A2).

Said developments, derivatizations and preparations of proteins of the invention are particularly desired if said proteins continue to be proteolytically active, since this is the precondition for their possible uses of the invention. Preferably, the proteases obtained by any kind of mutagenesis and/or derivatizations have, compared to the starting molecule and to the non-derivatized molecule, respectively, increased proteolytic activity and very particularly improved performances with respect to their intended technical field of use in each case, including, in particular, improvement of their washing and/or cleaning performance for use in detergents or cleaning agents.

This is possible, for example, by combining the point mutations of the invention with further point mutations which relate to the catalyzed reaction, for example at the active site. Thus it would be possible, following the teaching of application WO 95/30011 A2, for example, to mutate proteases of the invention which are those derived from *Bacillus lentus* subtilisin in the loop regions or to introduce additional amino acids. Such studies are described in the applications published under numbers WO 00/37599 A1, WO 00/37621 A1 to WO 00/37627 A1 and WO 00/71683 A1 to WO 00/71691 A1.

The deletion of a region of the enzyme, which interacts with other active compounds in the reaction medium and thus impairs the overall reaction, for example via folding effects, could be such a desired development. Analogously, fusion to other active enzymes, for example to other proteases, is conceivable in order to achieve an increased rate of hydrolysis.

The reversible blocking of a proteolytic activity during storage, due to binding of an inhibitor, for example, can stop autoproteolysis and thus effect a higher rate of proteolysis in the reaction medium at the time of dilution. Coupling to special binding domains, for example, may increase in the purification process the concentration of the protease close to the substrate relative to that in the liquor and thus increase the contribution of said enzyme to the performance of the agent.

In another embodiment, said proteins or derivatives are characterized in that they are additionally stabilized or have more than one of the stabilizations illustrated above.

Particularly relevant to the invention among these are, for practicability reasons, those methods which are based on point mutagenesis. All of the possibilities already illustrated above can also be applied in combination to variants of the invention, since, according to WO 89/09819 A1, it can be assumed that multiple stabilizing mutations have an additive effect. Thus, variants of the invention, for example, which have already been stabilized by either of or both of the two amino acids 3T and 4I, can be additionally stabilized by coupling to a polymer or in a different manner described above.

The second subject matter of the invention are nucleic acids. They include, in each case with corresponding preference, the nucleic acids coding for the proteins or derivatives of the first subject matter of the invention.

Nucleic acids are the starting point for virtually all common molecular-biological studies and developments of proteins and production thereof, including, in particular, sequencing of genes and derivation of the corresponding amino acid sequence, any kind of mutagenesis and expression of the proteins. Such methods are described, for example, in the manual by Fritsch, Sambrook and Maniatis "Molecular cloning: a laboratory manual", Cold Spring Harbour Laboratory Press, New York, 1989.

At the DNA level, the enzymes important to the invention may be optimized for various applications via any methods generally listed under the term "protein engineering". This makes it possible, in particular, to achieve the following properties which occur at the protein level: improvement of the resistance of the derived protein to oxidation, of the stability to denaturing agents or proteases, to high temperatures, to acidic or strongly alkaline conditions, alteration of the sensitivity to calcium or other cofactors, reduction in immunogenicity or allergenic action.

Examples of mutated genes of the invention include those responsible for individual, specific base substitutions or randomized point mutations, for deletions of individual bases or of partial sequences, fusions to other genes or gene fragments or inversions. Mutations or modifications of this kind can predestine the enzyme derived from the respective nucleic acids for specific applications. Such a mutagenesis may be carried out target-specifically or via random methods, for example using a subsequent recognition and/or selection method (screening and selection) on the cloned genes, targeted on the activity.

In particular for the nucleic acids coding for protein fragments, all three reading frames, both in sense and in antisense orientation, must be taken into account, since such oligonucleotides can be used via the polymerase chain reaction (PCR) as starting points for the synthesis of related nucleic acids. Such oligonucleotides are explicitly included within the scope of protection of the present invention, in particular when covering any of the regions corresponding to the five amino acid positions 3, 4, 61, 199 and/or 211. This applies also to those which have variable sequences at precisely these positions so that, within a population of a multiplicity of primers, there may also be at least one that codes for a partial sequence corresponding to either of SEQ ID No. 3 and/or SEQ ID No. 5 for such a position. The same applies to antisense oligonucleotides which may be used for regulating expression, for example.

The development of the proteases of the invention may be oriented in particular on the ideas presented in the publication "Protein engineering" by P. N. Bryan (2000) in *Biochim. Biophys. Acta.*, Volume 1543, pp. 203-222.

The representatives of this subject matter of the invention are preferably nucleic acids coding for subtilisin proteases, whose nucleotide sequence corresponds to either of the nucleotide sequences indicated in SEQ ID No. 3 and SEQ ID No. 5. Said correspondence relates particularly to the regions coding, according to the amino acid sequences SEQ ID No. 4 and SEQ ID No. 6, for isoleucine at position 199, for aspartic acid at position 211, for threonine at position 3 and/or for isoleucine at position 4, and very particularly for alanine at position 61 or including these regions.

As illustrated above and in the examples, said positions characterize particularly preferred representatives of alkaline proteases of the invention. This teaching is transferred to other subtilisins conveniently by mutation of the respective other molecules in one or more of said positions. Expediently, said mutation is carried out according to methods known per se (see above) at the nucleic acid level.

This preferentially applies to those nucleic acids which can be derived from a sequence for a *Bacillus lentus* protease, and particularly from a sequence for a *Bacillus lentus* DSM 5483 protease. In very particularly preferred cases, the nucleic acid codes for either of the variants of the invention, *B. lentus* alkaline protease S3T/V4I/G61A/V199I and *B. lentus* alkaline protease S3T/V4I/G61A/V199I/L211D, and/or corresponds to either of the nucleotide sequences indicated in SEQ ID No. 3 and SEQ ID No. 5. Said correspondence refers to the regions characterizing said variants and particularly preferably to the complete sequences.

The scope of protection also includes, for example, those nucleic acids coding for proteolytically active insertion or fusion mutants. Thus the region responsible for this activity may be fused, for example, to cellulose-binding domains or may carry point mutations in catalytically inactive regions in order to enable the derived protein to be coupled to a polymer or to reduce the allergenicity thereof.

A separate subject matter of the invention comprises vectors. These include vectors comprising any of the nucleic acid regions defined above and in particular a nucleic acid region coding for any of the proteins or derivatives defined above.

In order to handle the nucleic acids relevant to the invention, they are conveniently ligated into vectors. Such vectors are described in detail in the prior art and are commercially available in a large number and range of variations, both for cloning and for expression. They include, for example, vectors derived from bacterial plasmids, from viruses or from bacteriophages, or largely synthetic vectors. They are suitable starting points for molecular-biological and biochemical studies, for expression of the gene in question or of the corresponding protein.

Vectors of the invention are preferably cloning vectors which comprise any of the nucleic acid regions defined above and in particular comprise a nucleic acid region coding for any of the proteins or derivatives defined above.

Cloning vectors are, in addition to storage, biological amplification or selection of the gene of interest, suitable for molecular-biological characterization of said gene. At the same time, they are transportable and storable forms of the claimed nucleic acids and are also starting points for molecular-biological techniques not linked to cells, such as PCR or in-vitro mutagenesis methods, for example.

Likewise preferably, vectors of the invention are expression vectors which comprise any of the nucleic acid regions defined above and comprise in particular a nucleic acid region coding for any of the proteins or derivatives defined above and making possible the biosynthesis thereof.

Expression vectors of this kind are the basis for implementing the corresponding nucleic acids in biological production systems and thereby producing the corresponding proteins. Preferred embodiments of this subject matter of the invention are expression vectors which carry all the genetic elements necessary for expression, for example the natural promoter originally located upstream of said gene or a promoter from another organism. Said elements may be arranged, for example, the form of an "expression cassette". Particular preference is given to matching them to the chosen expression system, in particular the host cell (see below).

A separate subject matter of the invention comprises cells which may be utilized in any form for developing, modifying or producing proteins or derivatives of the invention. They include in particular cells containing any of the vectors defined above or the characterizing regions thereof, located either on a plasmid or in the chromosome.

These make possible, for example, amplification of the corresponding genes, but also mutagenesis or transcription and translation thereof and, ultimately, biotechnological production.

Preference is given to host cells which express or can be induced to express any of the proteins or derivatives defined above, in particular using any of the nucleic acid regions defined above, very particularly using an expression vector defined above.

The host cells producing said proteins make possible the biotechnological production thereof. For this purpose, they must have received the gene in question, conveniently via a vector, i.e. they must have been transformed. Said vector or its characterizing regions may be present in the host cell extrachromosomally as separate genetic element or may have been integrated into a chromosome.

Suitable host cells are in principle all organisms, i.e. prokaryotes, eukaryotes or Cyanophyta. Preference is given to those host cells which are easily manageable genetically, with respect to, for example, transformation with the expression vector or to its stable establishment, for example unicellular fungi or bacteria. Moreover, preferred host cells are distinguished by good microbiological and biotechnological manageability. This relates, for example, to easy culturability, high growth rates, low demands on fermentation media and good rates of production and secretion of foreign proteins. In this way, any protein of the invention can be obtained from a multiplicity of host organisms. Frequently, it is necessary to determine experimentally the expression systems optimal for the individual case from the abundance of different systems available according to the prior art.

Preferred embodiments are those host cells whose activity can be regulated owing to appropriate genetic elements, for example by controlled addition of chemical compounds, by changing the culturing conditions or as a function of the particular cell density. This controllable expression makes possible very economical production of the proteins of interest. Conveniently, expression vector and host cell match one another, with respect to the genetic elements required for expression (ribosome-binding site, promoters, terminators) or to codon usage, for example. The latter, for example, may be optimized by replacing in the gene those codons which are translated only poorly by the host in question with those more commonly used by the particularly host, with identical meaning in each case.

In a preferred embodiment, the host cell is characterized in that it is a bacterium, in particular one which secretes the protein produced into the surrounding medium.

Bacteria distinguish themselves by short generation times and low demands on the culturing conditions. This makes it possible to establish cost-effective methods. Moreover, a wealth of experience in bacterial fermentation techniques is available. For a large variety of reasons to be determined experimentally in the individual case, such as nutrient sources, rate of product formation, time required, etc., Gram-negative or Gram-positive bacteria may be suitable for a specific production.

Gram-negative bacteria such as *E. coli*, for example, secrete a multiplicity of proteins into the periplasmic space. This may be advantageous for special applications. In contrast, Gram-positive bacteria such as bacilli, for example, release secreted proteins immediately into the nutrient medium surrounding the cells, from which the expressed proteins of the invention can be purified directly, according to another preferred embodiment. The application WO 01/81597 even discloses a method according to which export of the expressed proteins by Gram-negative bacteria is also achieved.

Preference is given to bacteria characterized in that they are Gram-positive bacteria, in particular that they belong to the genus *Bacillus*, very particularly to the species *Bacillus lentus*, *Bacillus licheniformis*, *Bacillus amyloliquefaciens*, *Bacillus subtilis* or *Bacillus alcalophilus*.

One embodiment of the present invention utilizes *Bacillus lentus*, in particular *B. lentus* DSM 5483 itself, in order to (homologously) express proteins of the invention. On the other hand, however, preference is given to heterologous expression for which bacteria of the genus *Bacillus* are preferred, because they are the best characterized among Gram-positive bacteria, with respect to production. Included here are in particular those of the species *Bacillus licheniformis*, *Bacillus amyloliquefaciens*, *Bacillus subtilis* or other species or strains of *Bacillus alcalophilus*, since these species which are related to *Bacillus lentus* have a similar codon usage and produce comparable subtilisins themselves, i.e. have by nature an appropriately orientated synthesis apparatus.

Another advantage may be the possibility of obtaining via this method a mixture of proteins of the invention with the subtilisins endogenously produced by the host strains. The application WO 91/02792 (EP 493398 B1) describes, for example, coexpression of this kind of *B. lentus* alkaline protease in *Bacillus licheniformis* ATCC 53926; numerous possible expression vectors are also disclosed there. These systems may also be applied to the newly found variants of the invention.

Further preference is given to host cells characterized in that they are eukaryotic cells, in particular those which modify posttranslationally the protein produced.

Examples of suitable eukaryotes are fungi such as actinomycetes or yeasts such as *Saccharomyces* or *Kluyveromyces*. The modifications which systems of this kind carry out, in particular in connection with protein synthesis, include binding of low molecular compounds such as membrane anchors or oligosaccharides, for example. Oligosaccharide modifications of this kind may be desirable, for example, for reducing allergenicity.

Methods for preparing a proteolytic enzyme or derivative of the invention are a separate subject matter of the invention.

Thus, methods for preparing an above-described proteolytic enzyme or derivative by using a nucleic acid defined above and/or using a vector defined above and/or using any of the host cells defined above are claimed.

Thus, it is possible, for example on the basis of the above-defined DNA sequences and amino acid sequences, as can be derived, for example, also from the sequence listing, to synthesize corresponding oligopeptides and oligonucleotides up to the complete genes and proteins according to molecular-biological methods known per se. Starting from the known subtilisin-producing microorganisms, it is also possible to isolate further natural subtilisin producers, to determine their subtilisin sequences and to develop them, according to the conditions made herein. Bacterial species of this kind may also be cultured for appropriate production methods. Analogously, novel expression vectors may be developed according to the model of the vectors disclosed in the application WO 91/02792. Cell-free expression systems in which protein biosynthesis is carried out in vitro may also be embodiments of the present invention, on the basis of the corresponding nucleic acid sequences. Any elements already set forth above may also be combined to give novel methods for preparing proteins of the invention. In this connection, a multiplicity of possible combinations of the method steps for each protein of the invention is conceivable so that optimal methods must be determined experimentally for each specific individual case.

A separate subject matter of the invention comprises agents containing an above-defined proteolytic enzyme of the invention. They are in particular detergents or cleaning agents, very particularly in an amount of from 2 µg to 20 mg per g of said agent.

Virtually all possible technical uses of enzymes of the invention depend on using the functional enzyme in an appropriate medium. Thus, for example, the possible microbiological uses demand agents in which the enzyme, usually in the form of highly pure preparations, is combined with the necessary reaction partners or cofactors. Agents for the treatment of raw materials or cosmetic preparations are likewise characterized by specific formulations. According to the invention, all these formulations should be understood as being agents containing the enzyme of the invention.

Preferred embodiments included in this subject matter of the invention are detergents or cleaning agents, since, as the exemplary embodiments of the present application show, it was surprisingly found that a subtilisin variant having a substitution at position 61 (numbering according to *B. lentus* alkaline protease) by any of the amino acids alanine, valine, leucine, isoleucine, cysteine, methionine, phenylalanine, tyrosine, tryptophan, threonine, histidine, lysine and arginine, particularly by any of the amino acids alanine, valine, leucine and isoleucine, very particular by alanine, gives a distinct performance increase, in comparison with the non-mutated molecule, on various soilings both of textiles and of hard surfaces. This effect occurs reproducibly both at different temperatures and at different concentrations.

Accordingly, preference is given to agents containing the above-described variants. Included here are in particular those containing the *B. lentus* alkaline protease variants S3T/V4I/G61A/V199I and S3T/V4I/G61A/V199I/L211D and those containing the molecules derived from the latter.

This subject matter of the invention includes any conceivable types of cleaning agents, both concentrates and agents to be applied in undiluted form; for use on the commercial scale, in the washing machine or for manual laundry or cleaning. They include, for example, detergents for textiles, carpets or natural fibers, for which the term detergent is used in the present invention. They also include, for example, dishwashing agents for dishwashers or manual dishwashing agents or cleaners for hard surfaces such as metal, glass, porcelain, ceramic, tiles, stone, coated surfaces, plastics, wood or leather; for those, the term cleaning agent is used in the present invention. Any type of cleaning agent is an embodiment of the present invention, as long as a protein of the invention has been added to it.

Embodiments of the present invention comprise any presentation forms of the agents of the invention, which are established in the prior art and/or appropriate. They include, for example, solid, pulverulent, liquid, gel-like or paste-like agents, where appropriate also composed of a plurality of phases, compressed or uncompressed; further examples include: extrudates, granules, tablets or pouches, packaged both in large containers and in portions.

Agents of the invention contain enzymes of the invention in an amount of from 2 µg to 20 mg and, increasingly preferably, from 5 µg to 17.5 mg, from 20 µg to 15 mg, from 50 µg to 10 mg, from 100 µg to 7.5 mg, from 200 µg to 5 mg and from 500 µg to 1 mg, per gram of agent. This results in amounts of from 40 µg to 4 g and, increasingly preferably, from 50 µg to 3 g, from 100 µg to 2 g, from 200 µg to 1 g and, particularly preferably, from 400 µg to 400 mg per application.

The protease activity in agents of this kind may be determined according to the method described in *Tenside*, Volume 7 (1970), pp. 125-132 and is, accordingly, indicated in protease units (PE=Protease-Einheiten). The protease activity of the agents may be up to 1 500000 protease units per gram of preparation.

Apart from an enzyme important to the invention, an agent of the invention contains, where appropriate, further ingredients such as surfactants, for example nonionic, anionic and/or amphoteric surfactants, and/or bleaches, and/or builders, and, where appropriate, further conventional ingredients.

The nonionic surfactants used are preferably alkoxylated, advantageously ethoxylated, in particular primary alcohols having preferably from 8 to 18 carbon atoms and, on average, from 1 to 12 mol of ethylene oxide (EO) per mole of alcohol, in which the alcohol radical can be linear or, preferably, methyl-branched in the 2-position or can comprise linear and methyl-branched radicals in a mixture as are customarily present in oxo alcohol radicals. Particular preference is, however, given to alcohol ethoxylates containing linear radicals of alcohols of native origin having from 12 to 18 carbon atoms, for example from coconut, palm, tallow fatty or oleyl alcohol, and, on average, from 2 to 8 EO per mole of alcohol. Preferred ethoxylated alcohols include, for example, $C_{12-14}$-alcohols having 3 EO or 4 EO, $C_{9-11}$-alcohol having 7 EO, $C_{13-15}$-alcohols having 3 EO, 5 EO, 7 EO or 8 EO, $C_{12-18}$-alcohols having 3 EO, 5 EO, or 7 EO, and mixtures of these, such as mixtures of $C_{12-14}$-alcohol having 3 EO and $C_{12-18}$-alcohol having 5 EO. The degrees of ethoxylation given are statistical averages which may be an integer or a fraction for a specific product. Preferred alcohol ethoxylates have a narrowed homolog distribution (narrow range ethoxylates, NRE). In addition to these nonionic surfactants, fatty alcohols having more than 12 EO can also be used. Examples thereof are tallow fatty alcohol having 14 EO, 25 EO, 30 EO or 40 EO.

A further class of preferably used nonionic surfactants which are used either as the sole nonionic surfactant or in combination with other nonionic surfactants are alkoxylated, preferably ethoxylated or ethoxylated and propoxylated, fatty acid alkyl esters, preferably having from 1 to 4 carbon atoms in the alkyl chain, in particular fatty acid methyl esters.

A further class of nonionic surfactants which can advantageously be used are the alkyl polyglycosides (APG). Alkyl polyglycosides which may be used satisfy the general formula $RO(G)_z$, in which R is a linear or branched, in particular methyl-branched in the 2-position, saturated or unsaturated, aliphatic radical having from 8 to 22, preferably from 12 to 18 carbon atoms, and G is the symbol which stands for a glycose unit having 5 or 6 carbon atoms, preferably for glucose. The degree of glycosylation z is here between 1.0 and 4.0, preferably between 1.0 and 2.0 and in particular between 1.1 and 1.4. Preference is given to using linear alkyl polyglucosides, i.e. alkyl polyglycosides in which the polyglycosyl radical is a glucose radical, and the alkyl radical is an n-alkyl radical.

Nonionic surfactants of the amine oxide type, for example N-cocoalkyl-N,N-dimethylamine oxide and N-tallow alkyl-N,N-dihydroxyethylamine oxide, and of the fatty acid alkanolamides may also be suitable. The proportion of these nonionic surfactants is preferably no more than that of the ethoxylated fatty alcohols, in particular no more than half thereof.

Further suitable surfactants are polyhydroxy fatty acid amides of the formula (II)

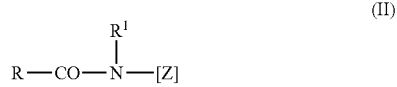

(II)

in which RCO is an aliphatic acyl radical having from 6 to 22 carbon atoms, $R^1$ is hydrogen, an alkyl or hydroxyalkyl radical having from 1 to 4 carbon atoms and [Z] is a linear or branched polyhydroxyalkyl radical having from 3 to 10 carbon atoms and from 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride.

The group of polyhydroxy fatty acid amides also includes compounds of the formula (III)

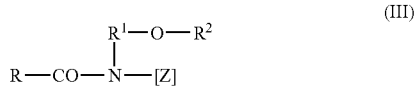

(III)

in which R is a linear or branched alkyl or alkenyl radical having from 7 to 12 carbon atoms, $R^1$ is a linear, branched or cyclic alkyl radical or an aryl radical having from 2 to 8 carbon atoms, and $R^2$ is a linear, branched or cyclic alkyl radical or an aryl radical or an oxyalkyl radical having from 1 to 8 carbon atoms, where $C_{1-4}$-alkyl or phenyl radicals are preferred, and [Z] is a linear polyhydroxyalkyl radical whose alkyl chain is substituted with at least two hydroxyl groups, or alkoxylated, preferably ethoxylated or propoxylated, derivatives of this radical.

[Z] is preferably obtained by reductive amination of a reducing sugar, for example glucose, fructose, maltose, lactose, galactose, mannose or xylose. The N-alkoxy- or N-aryloxy-substituted compounds may be converted, for example, by reaction with fatty acid methyl esters in the presence of an alkoxide as catalyst, into the desired polyhydroxy fatty acid amides.

The anionic surfactants used are, for example, those of the sulfonate and sulfate type. Suitable surfactants of the sulfonate type are preferably $C_{9-13}$-alkylbenzenesulfonates, olefinsulfonates, i.e. mixtures of alkene- and hydroxyalkanesulfonates, and disulfonates, as obtained, for example, from $C_{12-18}$-monoolefins having a terminal or internal double bond by sulfonation with gaseous sulfur trioxide and subsequent alkaline or acidic hydrolysis of the sulfonation products. Also suitable are alkanesulfonates which are obtained from $C_{12-18}$-alkanes, for example, by sulfochlorination or sulfoxidation with subsequent hydrolysis or neutralization. Likewise suitable are also the esters of α-sulfo fatty acids (estersulfonates), for example the α-sulfonated methyl esters of hydrogenated coconut, palm kernel or tallow fatty acids.

Further suitable anionic surfactants are sulfated fatty acid glycerol esters. Fatty acid glycerol esters mean the mono-, di- and triesters, and mixtures thereof, as are obtained during the preparation by esterification of a monoglycerol with from 1 to 3 mol of fatty acid or during the transesterification of triglycerides with from 0.3 to 2 mol of glycerol. Preferred sulfated fatty acid glycerol esters are here the sulfation products of saturated fatty acids having from 6 to 22 carbon atoms, for example of caproic acid, caprylic acid, capric acid, myristic acid, lauric acid, palmitic acid, stearic acid or behenic acid.

Preferred alk(en)yl sulfates are the alkali metal, and in particular the sodium, salts of sulfuric monoesters of $C_{12}$-$C_{18}$-fatty alcohols, for example of coconut fatty alcohol, tallow fatty alcohol, lauryl, myristyl, cetyl or stearyl alcohol or of $C_{10}$-$C_{20}$-oxo alcohols and those monoesters of secondary alcohols of these chain lengths. Further preferred are alk(en)yl sulfates of said chain length which comprise a synthetic, petrochemical-based straight-chain alkyl radical and have analogous degradation behavior to the equivalent compounds based on fatty chemical raw materials. From a washing performance viewpoint, preference is given to $C_{12}$-$C_{16}$-alkyl sulfates and $C_{12}$-$C_{15}$-alkyl sulfates, and $C_{14}$-$C_{15}$-alkyl sulfates. 2,3-Alkyl sulfates are also suitable anionic surfactants.

The sulfuric monoesters of straight-chain or branched $C_{7-21}$-alcohols ethoxylated with from 1 to 6 mol of ethylene oxide, such as 2-methyl-branched $C_{9-11}$-alcohols having, on average, 3.5 mol of ethylene oxide (EO) or $C_{12-18}$-fatty alcohols having from 1 to 4 EO, are also suitable. Owing to their high foaming behavior, they are used in cleaning agents only in relatively small amounts, for example in amounts up to 5% by weight, usually from 1 to 5% by weight.

Further suitable anionic surfactants are also the salts of alkylsulfosuccinic acid, which are also referred to as sulfosuccinates or as sulfosuccinic esters and which are monoesters and/or diesters of sulfosuccinic acid with alcohols, preferably fatty alcohols and, in particular, ethoxylated fatty alcohols. Preferred sulfosuccinates contain $C_{8-18}$-fatty alcohol radicals or mixtures thereof. Particularly preferred sulfosuccinates contain a fatty alcohol radical derived from ethoxylated fatty alcohols, which are themselves nonionic surfactants (see above for description). In this connection, sulfosuccinates whose fatty alcohol radicals are derived from ethoxylated fatty alcohols having a narrowed homolog distribution are, in turn, particularly preferred. Likewise, it is also possible to use alk(en)ylsuccinic acid having preferably from 8 to 18 carbon atoms in the alk(en)yl chain or salts thereof.

Further suitable anionic surfactants are, in particular, soaps. Saturated fatty acid soaps such as the salts of lauric acid, myristic acid, palmitic acid, stearic acid, hydrogenated erucic acid and behenic acid, and, in particular, soap mixtures derived from natural fatty acids, for example coconut, palm kernel or tallow fatty acids, are suitable.

The anionic surfactants including soaps may be present in the form of their sodium, potassium or ammonium salts, and as soluble salts of organic bases such as mono-, di- or triethanolamine. The anionic surfactants are preferably in the form of their sodium or potassium salts, in particular in the form of the sodium salts.

The surfactants may be present in the cleaning agents or detergents of the invention in an overall amount of from preferably 5% by weight to 50% by weight, in particular from 8% by weight to 30% by weight, based on the finished agent.

Agents of the invention may contain bleaches. Of the compounds which serve as bleaches and produce $H_2O_2$ in water, sodium percarbonate, sodium perborate tetrahydrate and sodium perborate monohydrate are of particular importance. Other bleaches which can be used are, for example, peroxopyrophosphates, citrate perhydrates and $H_2O_2$-producing peracidic salts or peracids, such as persulfates or persulfuric acid. Also useful is the urea peroxohydrate percarbamide which can be described by the formula $H_2N$—$CO$—$NH_2.H_2O_2$. In particular when used for cleaning hard surfaces, for example for machine dishwashing, the agents, if desired, may also contain bleaches from the group of organic bleaches, although the use thereof is possible in principle also in agents for washing textiles. Typical organic bleaches are diacyl peroxides such as, for example, dibenzoyl peroxide. Further typical organic bleaches are the peroxy acids, specific examples being alkyl peroxy acids and aryl peroxy acids. Preferred representatives are peroxy benzoic acid and its ring-substituted derivatives, such as alkylperoxybenzoic acids, but also peroxy-α-naphthoic acid and magnesium monoperphthalate, the aliphatic or substituted aliphatic peroxy acids such as peroxylauric acid, peroxystearic acid, ε-phthalimidoperoxycaproic acid (phthalimidoperoxyhexanoic acid, PAP), o-carboxy-benzamidoperoxycaproic acid, N-nonenylamidoperadipic acid and N-nonenylamidopersuccinates, and aliphatic and araliphatic peroxydicarboxylic acids such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyldi(6-aminopercaproic acid) may be used.

The bleach content of the agents may be from 1 to 40% by weight and, in particular, from 10 to 20% by weight, using advantageously perborate monohydrate or percarbonate.

In order to achieve improved bleaching action in cases of washing at temperatures of 60° C. and below, and in particular in the case of laundry pretreatment, the agents may also include bleach activators. Bleach activators which can be used are compounds which, under perhydrolysis conditions, give aliphatic peroxocarboxylic acids having preferably from 1 to 10 carbon atoms, in particular from 2 to 4 carbon atoms, and/or substituted or unsubstituted perbenzoic acid. Substances which carry O— and/or N-acyl groups of said number of carbon atoms and/or substituted or unsubstituted benzoyl groups are suitable. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular 1,3,4,6-tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), acylated hydroxycarboxylic acids such as triethyl O-acetylcitrate (TEOC), carboxylic anhydrides, in particular phthalic anhydride, isatoic anhydride and/or succinic anhydride, carboxamides such as N-methyldiacetamide, glycolide, acylated polyhydric alcohols, in particular triacetin, ethylene glycol diacetate, isopropenyl acetate, 2,5-diacetoxy-2,5-dihydrofuran and the enol esters disclosed in German patent applications DE 196 16 693 and DE 196 16 767, and acetylated sorbitol and mannitol, or mixtures thereof described in European patent application EP 0 525 239 (SORMAN), acylated sugar derivatives, in particular pentaacetylglucose (PAG), pentaacetylfructose, tetraacetylxylose and octaacetyllactose, and acetylated, optionally N-alkylated glucamine or gluconolactone, triazole or triazole derivatives and/or particulate caprolactams and/or caprolactam derivatives, preferably N-acylated lactams, for example N-benzoylcaprolactam and N-acetylcaprolactam, which are disclosed in international patent applications WO 94/27970, WO 94/28102, WO 94/28103, WO 95/00626, WO 95/14759 and WO 95/17498. The hydrophilically substituted acyl acetals disclosed in German patent application DE 196 16 769 and the acyl lactams described in German patent application DE 196 16 770 and in international patent application WO 95/14075 are likewise used with preference. It is also possible to use the combinations of conventional bleach activators disclosed in German patent application DE 44 43 177. Nitrile derivatives such as cyanopyridines, nitrile quats, e.g. N-alkylammonium acetonitriles, and/or cyanamide derivatives may also be used. Preferred bleach activators are sodium 4-(octanoyloxy)benzenesulfonate, n-nonanoyl- or isononanoyloxybenzenesulfonate (n- or iso-NOBS), undecenoyloxybenzenesulfonate (UDOBS), sodium dodecanoyloxybenzenesulfonate (DOBS), decanoyloxybenzoic acid (DOBA, OBC 10) and/or dodecanoyloxybenzenesulfonate (OBS 12), and N-methylmorpholinium acetonitrile (MMA). Such bleach activators may be present in the customary quantitative range from 0.01 to 20% by weight, preferably in amounts from 0.1 to 15% by weight, in particular 1% by weight to 10% by weight, based on the total composition.

In addition to the conventional bleach activators or instead of them, it is also possible for "bleach catalysts" to be present. These substances are bleach-enhancing transition metal salts or transition metal complexes such as, for example, Mn, Fe, Co, Ru or Mo salen complexes or carbonyl complexes. Mn, Fe, Co, Ru, Mo, Ti, V and Cu complexes containing N-containing tripod ligands, and Co, Fe, Cu and Ru ammine complexes are also suitable as bleach catalysts, preference being given to using those compounds described in DE 197 09 284 A1. Acetonitrile derivatives, according to WO 99/63038, and bleach-activating transition metal complex compounds, according to WO 99/63041, are capable of developing a bleach-activating action in combination with amylases.

Agents of the invention usually contain one or more builders, in particular zeolites, silicates, carbonates, organic cobuilders and, where no ecological reasons oppose their use, also phosphates. The latter are the preferred builders for use in particular in cleaning agents for machine dishwashing.

Compounds which may be mentioned here are crystalline, layered sodium silicates of the general formula $NaMSi_xO_{2x+1}.yH_2O$, where M is sodium or hydrogen, x is a number from 1.6 to 4, preferably from 1.9 to 4.0, and y is a number from 0 to 20, and preferred values for x are 2, 3 or 4. Crystalline phyllosilicates of this kind are described, for example, in European patent application EP 0 164 514. Preferred crystalline phyllosilicates of the formula indicated are those where M is sodium and x adopts the values 2 or 3. In particular, both β- and δ-sodium disilicates $Na_2Si_2O_5.yH_2O$ are preferred. Compounds of this kind are sold, for example, under the name SKS® (Clariant). Thus, SKS-6® is primarily a δ-sodium disilicate having the formula $Na_2Si_2O_5.yH_2O$, and SKS-7® is primarily the β-sodium disilicate. Reacting the δ-sodium disilicate with acids (for example citric acid or carboxylic acid) gives kanemite, $NaHSi_2O_5.yH_2O$, sold under the names SKS-9® and, respectively, SKS-10® (Clariant). It may also be advantageous to use chemical modifications of said phyllosilicates. The alkalinity of the phyllosilicates, for example, can thus be suitably influenced. Phyllosilicates doped with phosphate or with carbonate have, compared to the δ-sodium disilicate, altered crystal morphologies, dissolve more rapidly and display an increased calcium binding ability, compared to δ-sodium disilicate. Thus, phyllosilicates of the general empirical formula $xNa_2O \cdot ySiO_2O \cdot zP_2O_5$ where the x-to-y ratio corresponds to a number from 0.35 to 0.6, the x-to-z ratio to a number from 1.75 to 1 200 and the y-to-z ratio to a number from 4 to 2 800 are described in patent application DE 196 01 063. The solubility of the phyllosilicates may also be increased by using particularly finely granulated phyllosilicates. It is also possible to use compounds of the crystalline phyllosilicates with other ingredients. Compounds which may be mentioned here are in particular those with cellulose derivatives which have advantageous disintegrating action and are used in particular in detergent tablets, and those with polycarboxylates, for example citric acid, or polymeric polycarboxylates, for example copolymers of acrylic acid.

It is also possible to use amorphous sodium silicates having an $Na_2O:SiO_2$ modulus of from 1:2 to 1:3.3, preferably from 1:2 to 1:2.8, and in particular from 1:2 to 1:2.6, which have delayed dissolution and secondary detergent properties. The dissolution delay relative to conventional amorphous sodium silicates can have been induced by various means, for example by surface treatment, compounding, compaction/compression or by overdrying. Within the scope of this invention, the term "amorphous" also means "X-ray amorphous". This means that in X-ray diffraction experiments the silicates do not give the sharp X-ray reflections typical of crystalline substances, but instead, at best, one or more maxima of the scattered X-ray radiation, which have a width of several degree units of the diffraction angle. However, even particularly good builder properties will very likely result if, in electron diffraction experiments, the silicate particles give poorly defined or even sharp diffraction maxima. This is to be interpreted to the effect that the products have microcrystalline regions with a size from 10 to a few hundred nm, preference being given to values up to at most 50 nm and in particular up to at most 20 nm. Particular preference is given to compressed/compacted amorphous silicates, compounded amorphous silicates and overdried X-ray amorphous silicates.

A finely crystalline, synthetic zeolite containing bonded water, which may be used where appropriate, is preferably zeolite A and/or P. As zeolite P, zeolite MAP® (commercial product from Crosfield) is particularly preferred. However, zeolite X and mixtures of A, X and/or P are also suitable. A product which is commercially available and can be used with preference within the scope of the present invention is, for example, also a cocrystal of zeolite X and zeolite A (approx. 80% by weight zeolite X), which is sold by CONDEA Augusta S.p.A. under the trade name VEGOBOND AX® and can be described by the formula

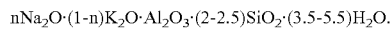
$nNa_2O \cdot (1-n)K_2O \cdot Al_2O_3 \cdot (2-2.5)SiO_2 \cdot (3.5-5.5)H_2O$.

Suitable zeolites have an average particle size of less than 10 μm (volume distribution; measurement method: Coulter counter) and preferably contain from 18 to 22% by weight, in particular from 20 to 22% by weight, of bonded water.

Use of the generally known phosphates as builder substances is of course also possible, provided such a use should not be avoided for ecological reasons. Among the multiplicity of commercially available phosphates, the alkali metal phosphates are the most important in the detergents and cleaning agents industry, with pentasodium or pentapotassium triphosphate (sodium or potassium tripolyphosphate) being particularly preferred.

In this connection, alkali metal phosphates is the collective term for the alkali metal (in particular sodium and potassium) salts of the various phosphoric acids, it being possible to differentiate between metaphosphoric acids $(HPO_3)_n$ and orthophosphoric acid $H_3PO_4$ as well as higher molecular weight representatives. The phosphates combine several advantages: they act as alkali carriers, prevent lime deposits on machine parts and lime incrustations in fabrics and, moreover, contribute to the cleaning performance.

Sodium dihydrogenphosphate, $NaH_2PO_4$, exists as dihydrate (density 1.91 $gcm^{-3}$, melting point 60° C.) and as monohydrate (density 2.04 $gcm^{-3}$). Both salts are white powders which are very readily soluble in water and which lose their water of crystallization upon heating and at 200° C. convert to the weakly acidic diphosphate (disodium hydrogendiphosphate, $Na_2H_2P_2O_7$), at a higher temperature to sodium trimetaphosphate $(Na_3P_3O_9)$ and Maddrell's salt (see below). $NaH_2PO_4$ is acidic; it forms when phosphoric acid is adjusted to a pH of 4.5 using sodium hydroxide solution and the slurry is sprayed. Potassium dihydrogenphosphate (primary or monobasic potassium phosphate, potassium biphosphate, KDP), $KH_2PO_4$, is a white salt of density 2.33 $gcm^{-3}$, has a melting point of 253° C. [decomposition with the formation of potassium polyphosphate $(KPO_3)_x$] and is readily soluble in water.

Disodium hydrogenphosphate (secondary sodium phosphate), $Na_2HPO_4$, is a colorless crystalline salt which is very readily soluble in water. It exists in anhydrous form and with 2 mol (density 2.066 $gcm^{-3}$, loss of water at 95° C.), 7 mol (density 1.68 $gcm^{-3}$, melting point 48° C. with loss of 5 $H_2O$), and 12 mol (density 1.52 $gcm^{-3}$, melting point 35° C. with loss of 5 $H_2O$) of water, becomes anhydrous at 100° C. and upon more vigorous heating converts to the diphosphate $Na_4P_2O_7$. Disodium hydrogenphosphate is prepared by neutralizing phosphoric acid with sodium carbonate solution using phenolphthalein as indicator. Dipotassium hydrogenphosphate (secondary or dibasic potassium phosphate), $K_2HPO_4$, is an amorphous, white salt which is readily soluble in water.

Trisodium phosphate, tertiary sodium phosphate, $Na_3PO_4$, are colorless crystals which, in the form of the dodecahydrate, have a density of 1.62 $gcm^{-3}$ and a melting point of 73-76° C. (decomposition), in the form of the decahydrate (corresponding to 19-20% $P_2O_5$) have a melting point of 100° C. and in anhydrous form (corresponding to 39-40% $P_2O_5$) have a density of 2.536 $gcm^{-3}$. Trisodium phosphate is readily soluble in water with an alkaline reaction and is prepared by evaporating a solution of exactly 1 mol of disodium phosphate and 1 mol of NaOH. Tripotassium phosphate (tertiary or tribasic potassium phosphate), $K_3PO_4$, is a white, deliquescent granular powder of density 2.56 $gcm^{-3}$, has a melting point of 1 340° C. and is readily soluble in water with an alkaline reaction. It is produced, for example, during the heating of Thomas slag with carbon and potassium sulfate. Despite the higher price, the more readily soluble, and therefore highly effective, potassium phosphates are often preferred over corresponding sodium compounds in the cleaning agents industry.

Tetrasodium diphosphate (sodium pyrophosphate), $Na_4P_2O_7$, exists in anhydrous form (density 2.534 $gcm^{-3}$, melting point 988° C., also 880° C. quoted) and as decahydrate (density 1.815-1.836 $gcm^{-3}$, melting point 94° C. with loss of water). Both substances are colorless crystals which dissolve in water with an alkaline reaction. $Na_4P_2O_7$ is formed during the heating of disodium phosphate to >200° C. or by reacting phosphoric acid with sodium carbonate in a stoichiometric ratio and dewatering the solution by spraying. The decahydrate complexes heavy metal salts and hardness constituents and thus reduces the water hardness. Potassium diphosphate (potassium pyrophosphate), $K_4P_2O_7$, exists in the form of the trihydrate and is a colorless, hygroscopic powder of density 2.33 gcm$^{-3}$, which is soluble in water, the pH of the 1% strength solution at 25° C. being 10.4.

Condensation of $NaH_2PO_4$ and $KH_2PO_4$ results in higher molecular weight sodium phosphates and potassium phosphates, respectively, amongst which cyclic representatives, the sodium and potassium metaphosphates, respectively, and chain-like types, the sodium and potassium polyphosphates, respectively, can be differentiated. Particularly for the latter, a multiplicity of names are in use: melt or thermal phosphates, Graham's salt, Kurrol's and Maddrell's salt. All higher sodium and potassium phosphates are together referred to as condensed phosphates.

The industrially important pentasodium triphosphate, $Na_5P_3O_{10}$ (sodium tripolyphosphate), is a nonhygroscopic, white, water-soluble salt which is anhydrous or crystallizes with 6 $H_2O$ and is of the general formula $NaO-[P(O)(ONa)-O]_n-Na$ where n=3. In 100 g of water, about 17 g of the salt which is free of water of crystallization dissolve at room temperature, approx. 20 g dissolve at 60° C., and about 32 g dissolve at 100° C.; if the solution is heated at 100° C. for two hours, about 8% of orthophosphate and 15% of diphosphate form due to hydrolysis. In the preparation of pentasodium triphosphate, phosphoric acid is reacted with sodium carbonate solution or sodium hydroxide solution in a stoichiometric ratio, and the solution is dewatered by spraying. Similarly to Graham's salt and sodium diphosphate, pentasodium triphosphate dissolves many insoluble metal compounds (including lime soaps, etc.). Pentapotassium triphosphate, $K_5P_3O_{10}$ (potassium tripolyphosphate), is available commercially, for example, in the form of a 50% strength by weight solution (>23% $P_2O_5$, 25% $K_2O$). The potassium polyphosphates are used widely in the detergents and cleaning agents industry. In addition, sodium potassium tripolyphosphates also exist which can likewise be used within the scope of the present invention. These form, for example, when sodium trimetaphosphate is hydrolyzed with KOH:

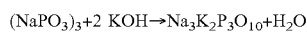

$(NaPO_3)_3 + 2\ KOH \rightarrow Na_3K_2P_3O_{10} + H_2O$

According to the invention, these can be used in exactly the same way as sodium tripolyphosphate, potassium tripolyphosphate or mixtures of these two; mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate can also be used according to the invention.

Organic cobuilders which can be used in the detergents and cleaning agents of the invention are, in particular, polycarboxylates or polycarboxylic acids, polymeric polycarboxylates, polyaspartic acid, polyacetals, optionally oxidized dextrins, further organic cobuilders (see below), and phosphonates. These classes of substance are described below.

Useable organic builder substances are, for example, the polycarboxylic acids usable in the form of their sodium salts, the term polycarboxylic acids meaning those carboxylic acids which carry more than one acid function. Examples of these are citric acid, adipic acid, succinic acid, glutaric acid, malic acid, tartaric acid, maleic acid, fumaric acid, sugar acids, aminocarboxylic acids, nitrilotriacetic acid (NTA), as long as such a use is not to be avoided for ecological reasons, and mixtures thereof. Preferred salts are the salts of the polycarboxylic acids such as citric acid, adipic acid, succinic acid, glutaric acid, tartaric acid, sugar acids, and mixtures thereof.

It is also possible to use the acids per se. In addition to their builder action, the acids typically also have the property of an acidifying component and thus also serve to establish a lower and milder pH of detergents or cleaning agents, if the pH resulting from the mixture of the remaining components is not desired. Particular mention should be made here of system-compatible and environmentally safe acids such as citric acid, acetic acid, tartaric acid, malic acid, lactic acid, glycolic acid, succinic acid, glutaric acid, adipic acid, gluconic acid and any mixtures thereof. However, mineral acids, in particular sulfuric acid, or bases, in particular ammonium or alkali metal hydroxides, may also serve as pH regulators. The agents of the invention contain such regulators in amounts of preferably not more than 20% by weight, in particular from 1.2% by weight to 17% by weight.

Suitable builders are also polymeric polycarboxylates; these are, for example, the alkali metal salts of polyacrylic acid or of polymethacrylic acid, for example those having a relative molecular mass of from 500 to 70000 g/mol.

The molar masses given for polymeric polycarboxylates are, for the purposes of this specification, weight-average molar masses, $M_W$, of the respective acid form, always determined by means of gel permeation chromatography (GPC), using a UV detector. The measurement was made against an external polyacrylic acid standard which, owing to its structural similarity toward the polymers studied, provides realistic molecular weight values. These figures differ considerably from the molecular weight values obtained using polystyrenesulfonic acids as the standard. The molar masses measured against polystyrenesulfonic acids are usually considerably higher than the molar masses given in this specification.

Suitable polymers are, in particular, polyacrylates which preferably have a molecular mass of from 2000 to 20000 g/mol. Owing to their superior solubility, preference in this group may be given in turn to the short-chain polyacrylates which have molar masses of from 2000 to 10000 g/mol, and particularly preferably from 3 000 to 5 000 g/mol.

Also suitable are copolymeric polycarboxylates, in particular those of acrylic acid with methacrylic acid and of acrylic acid or methacrylic acid with maleic acid. Copolymers which have proven to be particularly suitable are those of acrylic acid with maleic acid which contain from 50 to 90% by weight of acrylic acid and from 50 to 10% by weight of maleic acid. Their relative molecular mass, based on free acids, is generally from 2000 to 70000 g/mol, preferably 20000 to 50000 g/mol and in particular 30000 to 40000 g/mol. The (co)polymeric polycarboxylates may be used either as powders or as aqueous solution. The (co)polymeric polycarboxylates may be from 0.5 to 20% by weight, in particular 1 to 10% by weight of the content of the agent.

To improve the solubility in water, the polymers may also contain allylsulfonic acids such as, for example, allyloxybenzenesulfonic acid and methallylsulfonic acid as monomers.

Particular preference is also given to biodegradable polymers of more than two different monomer units, for example those which contain, as monomers, salts of acrylic acid and of maleic acid, and vinyl alcohol or vinyl alcohol derivatives, or those which contain, as monomers, salts of acrylic acid and of 2-alkylallylsulfonic acid, and sugar derivatives.

Further preferred copolymers are those which preferably have, as monomers, acrolein and acrylic acid/acrylic acid salts or acrolein and vinyl acetate.

Further preferred builder substances which may be mentioned are also polymeric aminodicarboxylic acids, their salts or their precursor substances. Particular preference is given to polyaspartic acids or salts and derivatives thereof.

Further suitable builder substances are polyacetals which can be obtained by reacting dialdehydes with polyolcarboxylic acids having from 5 to 7 carbon atoms and at least 3 hydroxyl groups. Preferred polyacetals are obtained from dialdehydes such as glyoxal, glutaraldehyde, terephthalaldehyde and mixtures thereof and from polyolcarboxylic acids such as gluconic acid and/or glucoheptonic acid.

Further suitable organic builder substances are dextrins, for example oligomers or polymers of carbohydrates, which can be obtained by partial hydrolysis of starches. The hydrolysis can be carried out by customary processes, for example acid-catalyzed or enzyme-catalyzed processes. The hydrolysis products preferably have average molar masses in the range from 400 to 500000 g/mol. Preference is given here to a polysaccharide having a dextrose equivalent (DE) in the range from 0.5 to 40, in particular from 2 to 30, where DE is a common measure of the reducing action of a polysaccharide compared with dextrose which has a DE of 100. It is possible to use both maltodextrins having a DE between 3 and 20 and dried glucose syrups having a DE between 20 and 37, and also "yellow dextrins" and "white dextrins" with higher molar masses in the range from 2000 to 30000 g/mol.

The oxidized derivatives of such dextrins are their reaction products with oxidizing agents which are able to oxidize at least one alcohol function of the saccharide ring to the carboxylic acid function. Particularly preferred organic builders for agents of the invention are oxidized starches and derivatives thereof of the applications EP 472042, WO 97/25399 and EP 755944, respectively.

Oxydisuccinates and other derivatives of disuccinates, preferably ethylenediamine disuccinate, are also further suitable cobuilders. Here, ethylenediamine N,N'-disuccinate (EDDS) is preferably used in the form of its sodium or magnesium salts. In this connection, further preference is also given to glycerol disuccinates and glycerol trisuccinates. Suitable use amounts in zeolite-containing, carbonate-containing and/or silicate-containing formulations are between 3 and 15% by weight.

Further organic cobuilders which can be used are, for example, acetylated hydroxycarboxylic acids or salts thereof, which may also be present, where appropriate, in lactone form and which contain at least 4 carbon atoms and at least one hydroxy group and at most two acid groups.

A further class of substance having cobuilder properties is the phosphonates. These are, in particular, hydroxyalkane- and aminoalkanephosphonates. Among the hydroxyalkanephosphonates, 1-hydroxyethane 1,1-diphosphonate (HEDP) is of particular importance as a cobuilder. It is preferably used as sodium salt, the disodium salt being neutral and the tetrasodium salt being alkaline (pH 9). Suitable aminoalkanephosphonates are preferably ethylenediaminetetramethylenephosphonate (EDTMP), diethylenetriamine-pentamethylenephosphonate (DTPMP) and higher homologs thereof. They are preferably used in the form of the neutral sodium salts, for example as the hexasodium salt of EDTMP or as the hepta- and octasodium salt of DTPMP. Here, preference is given to using HEDP as builder from the class of phosphonates. In addition, the aminoalkanephosphonates have a marked heavy metal-binding capacity. Accordingly, particularly if the agents also contain bleaches, it may be preferable to use aminoalkanephosphonates, in particular DTPMP, or mixtures of said phosphonates.

In addition, all compounds which are able to form complexes with alkaline earth metal ions can be used as cobuilders.

The agents of the invention may contain builder substances, where appropriate, in amounts of up to 90% by weight, and preferably contain them in amounts of up to 75% by weight. Detergents of the invention have builder contents of, in particular, from 5% by weight to 50% by weight. In inventive agents for cleaning hard surfaces, in particular for machine cleaning of dishes, the builder substance content is in particular from 5% by weight to 88% by weight, with preferably no water-insoluble builder materials being used in such agents. A preferred embodiment of inventive agents for, in particular, machine cleaning of dishes contains from 20% by weight to 40% by weight water-soluble organic builders, in particular alkali metal citrate, from 5% by weight to 15% by weight alkali metal carbonate and from 20% by weight to 40% by weight alkali metal disilicate.

Solvents which may be used in the liquid to gelatinous compositions of detergents and cleaning agents are, for example, from the group of monohydric or polyhydric alcohols, alkanolamines or glycol ethers, as long as they are miscible with water in the given concentration range. Preferably, the solvents are selected from ethanol, n- or isopropanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or monoethyl ether, diisopropylene glycol monomethyl or monoethyl ether, methoxy, ethoxy or butoxy triglycol, 1-butoxyethoxy-2-propanol, 3-methyl-3-methoxybutanol, propylene glycol t-butyl ether, and mixtures of these solvents.

Solvents may be used in the liquid to gelatinous detergents and cleaning agents of the invention in amounts of between 0.1 and 20% by weight, but preferably below 15% by weight, and in particular below 10% by weight.

To adjust the viscosity, one or more thickeners or thickening systems may be added to the composition of the invention. These high molecular weight substances which are also called swell(ing) agents usually soak up the liquids and swell in the process, converting ultimately into viscous, true or colloidal solutions.

Suitable thickeners are inorganic or polymeric organic compounds. Inorganic thickeners include, for example, polysilicic acids, clay minerals, such as montmorillonites, zeolites, silicas and bentonites. The organic thickeners are from the groups of natural polymers, modified natural polymers and completely synthetic polymers. Such natural polymers are, for example, agar-agar, carrageen, tragacanth, gum arabic, alginates, pectins, polyoses, guar flour, carob seed flour, starch, dextrins, gelatins and casein. Modified natural substances which are used as thickeners are primarily from the group of modified starches and celluloses. Examples which may be mentioned here are carboxymethylcellulose and other cellulose ethers, hydroxyethylcellulose and hydroxypropylcellulose, and carob flour ether. Completely synthetic thickeners are polymers such as polyacrylic and polymethacrylic compounds, vinyl polymers, polycarboxylic acids, polyethers, polyimines, polyamides and polyurethanes.

The thickeners may be present in an amount up to 5% by weight, preferably from 0.05 to 2% by weight, and particularly preferably from 0.1 to 1.5% by weight, based on the finished composition.

The detergent and cleaning agent of the invention may, where appropriate, comprise, as further customary ingredients, sequestering agents, electrolytes and further excipients such as optical brighteners, graying inhibitors, silver corrosion inhibitors, color transfer inhibitors, foam inhibitors, abrasive substances, dyes and/or fragrances, and microbial active substances and/or UV-absorbents.

The textile detergents of the invention may contain, as optical brighteners, derivatives of diaminostilbenedisulfonic acid or alkali metal salts thereof. Suitable are, for example, salts of 4,4'-bis(2-anilino-4-morpholino-1,3,5-triazinyl-6-amino)stilbene-2,2'-disulfonic acid or similarly constructed compounds which carry a diethanolamino group, a methylamino group, an anilino group or a 2-methoxyethylamino group instead of the morpholino group. In addition, brighteners of the substituted diphenylstyryl type may be present, for example the alkali metal salts of 4,4'-bis(2-sulfostyryl) diphenyl, 4,4'-bis(4-chloro-3-sulfostyryl)diphenyl, or 4-(4-chlorostyryl)-4'-(2-sulfostyryl)diphenyl. Mixtures of the abovementioned optical brighteners may also be used.

Graying inhibitors have the function of keeping the soil detached from the textile fiber in suspension in the liquor. Suitable for this purpose are water-soluble colloids, usually organic in nature, for example starch, size, gelatin, salts of ethercarboxylic acids or ethersulfonic acids of starch or of cellulose, or salts of acidic sulfuric esters of cellulose or of starch. Water-soluble polyamides containing acidic groups are also suitable for this purpose. Furthermore, starch derivatives other than those mentioned above may be used, for example aldehyde starches. Preference is given to cellulose ethers such as carboxymethylcellulose (Na salt), methylcellulose, hydroxyalkylcellulose and mixed ethers such as methylhydroxyethylcellulose, methylhydroxypropylcellulose, methylcarboxymethylcellulose, and mixtures thereof, for example in amounts of from 0.1 to 5% by weight, based on the agents.

In order to protect against silver corrosion, silver corrosion inhibitors may be used in dishwashing cleaning agents of the invention. Such inhibitors are known in the prior art, for example benzotriazoles, iron(III) chloride or $CoSO_4$. As disclosed by, for example, European patent EP 0 736 084 B1, silver corrosion inhibitors which are particularly suitable for being used together with enzymes are manganese, titanium, zirconium, hafnium, vanadium, cobalt, or cerium salts and/or complexes in which the specified metals are present in any of the oxidation states II, III, IV, V or VI. Examples of such compounds are $MnSO_4$, $V_2O_5$, $V_2O_4$, $VO_2$, $TiOSO_4$, $K_2TiF_6$, $K_2ZrF_6$, $Co(NO_3)_2$, $Co(NO_3)_3$, and mixtures thereof.

Soil-release active ingredients or soil repellents are usually polymers which, when used in a detergent, impart soil-repellent properties to the laundry fiber and/or assist the ability of the other detergent ingredients to detach soil. A comparable effect can also be observed with their use in cleaning agents for hard surfaces.

Soil-release active ingredients which are particularly effective and have been known for a long time are copolyesters having dicarboxylic acid, alkylene glycol and polyalkylene glycol units. Examples thereof are copolymers or mixed polymers of polyethylene terephthalate and polyoxyethylene glycol (DT 16 17 141, and, respectively, DT 2200 911). German Laid-Open Specification DT 22 53 063 discloses acidic agents containing, inter alia, a copolymer of a dibasic carboxylic acid and an alkylene or cycloalkylene polyglycol. German documents DE 28 57 292 and DE 33 24 258 and European patent EP 0 253 567 describe polymers of ethylene terephthalate and polyethylene oxide terephthalate and the use thereof in detergents. European patent EP 066 944 relates to agents containing a copolyester of ethylene glycol, polyethylene glycol, aromatic dicarboxylic acid and sulfonated aromatic dicarboxylic acid in particular molar ratios. European patent EP 0 185 427 discloses methyl or ethyl group end-capped polyesters having ethylene and/or propylene terephthalate and polyethylene oxide terephthalate units, and detergents containing such a soil-release polymer. European patent EP 0 241 984 discloses a polyester which contains, in addition to oxyethylene groups and terephthalic acid units, also substituted ethylene units and glycerol units. European patent EP 0 241 985 discloses polyesters which contain, in addition to oxyethylene groups and terephthalic acid units, 1,2-propylene, 1,2-butylene and/or 3-methoxy-1,2-propylene groups, and glycerol units and which are end-group-capped with $C_1$- to $C_4$-alkyl groups. European patent application EP 0 272033 discloses polyesters having polypropylene terephthalate and polyoxyethylene terephthalate units, which are at least partially end-group-capped by $C_{1-4}$-alkyl or acyl radicals. European patent EP 0 274 907 describes sulfoethyl end-group-capped terephthalate-containing soil-release polyesters. According to European patent application EP 0 357 280, sulfonation of unsaturated end groups produces soil-release polyesters having terephthalate, alkylene glycol and poly-$C_{2-4}$-glycol units. International patent application WO 95/32232 relates to acidic, aromatic polyesters capable of detaching soil. International patent application WO 97/31085 discloses nonpolymeric soil-repellent active ingredients for materials made of cotton, which have a plurality of functional units: a first unit which may be cationic, for example, is able to adsorb to the cotton surface by means of electrostatic interaction, and a second unit which is hydrophobic is responsible for the active ingredient remaining at the water/cotton interface.

The color transfer inhibitors suitable for use in laundry detergents of the invention include, in particular, polyvinylpyrrolidones, polyvinylimidazoles, polymeric N-oxides such as poly(vinylpyridine N-oxide) and copolymers of vinylpyrrolidone with vinylimidazole.

For use in machine cleaning processes, it may be of advantage to add foam inhibitors to the agents. Examples of suitable foam inhibitors are soaps of natural or synthetic origin having a high proportion of $C_{18}$-$C_{24}$ fatty acids. Examples of suitable nonsurfactant-type foam inhibitors are organopolysiloxanes and their mixtures with microfine, optionally silanized silica and also paraffins, waxes, microcrystalline waxes, and mixtures thereof with silanized silica or bis-stearyl-ethylenediamide. With advantages, use is also made of mixtures of different foam inhibitors, for example mixtures of silicones, paraffins or waxes. The foam inhibitors, in particular those containing silicone and/or paraffin, are preferably bound to a granular, water-soluble or dispersible support substance. Particular preference is given here to mixtures of paraffins and bis-stearylethylenediamides.

A cleaning agent of the invention for hard surfaces may, in addition, contain ingredients with abrasive action, in particular from the group comprising quartz flours, wood flours, polymer flours, chalks and glass microbeads, and mixtures thereof. Abrasives are present in the cleaning agents of the invention preferably at not more than 20% by weight, in particular from 5% by weight to 15% by weight.

Dyes and fragrances are added to detergents and cleaning agents in order to improve the esthetic appeal of the products and to provide the consumer, in addition to washing and cleaning performance, with a visually and sensorially "typical and unmistakable" product. As perfume oils and/or fragrances it is possible to use individual odorant compounds, for example the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenyl glycinate, allylcyclohexyl propionate, styrallyl propionate and benzyl salicylate. The ethers include, for example, benzyl ethyl ether; the aldehydes include, for example, the linear alkanals having 8-18 carbon atoms, citral, citronellal, citronellyloxyacetaldehyde, cyclamen aldehyde, hydroxycitronellal, lilial and bourgeonal; the ketones include, for example, the ionones, α-isomethylionone and methyl cedryl ketone; the alcohols include anethol, citronellol, eugenol, geraniol, linalool, phenylethyl alcohol, and terpineol; the hydrocarbons include primarily the terpenes such as limonene and pinene. Preference, however, is given to the use of mixtures of different odorants which together produce an appealing fragrance note. Such perfume oils may also contain natural odorant mixtures, as obtainable from plant sources, for example pine oil, citrus oil, jasmine oil, patchouli oil, rose oil or ylang-ylang oil. Likewise suitable are muscatel, sage oil, camomile oil, clove oil, balm oil, mint oil, cinnamon leaf oil, lime blossom oil, juniperberry oil, vetiver oil, olibanum oil, galbanum oil and labdanum oil, and also orange blossom oil, neroli oil, orange-peel oil and sandalwood oil. The dye content of detergents and cleaning agents is usually less than 0.01% by weight, while fragrances may make up up to 2% by weight of the overall formulation.

The fragrances may be incorporated directly into the detergents and cleaning agents; however, it may also be advantageous to apply the fragrances to carriers which enhance the adhesion of the perfume to the material to be cleaned and, by means of slower fragrance release, ensure long-lasting fragrance, in particular of treated textiles. Materials which have been established as such carriers are, for example, cyclodextrins, it being possible, in addition, for the cyclodextrin-perfume complexes also to be coated with further auxiliaries. Another preferred carrier for fragrances is the described zeolite X which can also absorb fragrances instead of or in a mixture with surfactants. Preference is therefore given to detergents and cleaning agents which contain the described zeolite X and fragrances which, preferably, are at least partially absorbed on the zeolite.

Preferred dyes whose selection is by no means difficult for the skilled worker have high storage stability and insensitivity to the other ingredients of the agents and to light, and also have no pronounced affinity for textile fibers, so as not to stain them.

To control microorganisms, detergents or cleaning agents may contain antimicrobial active ingredients. Depending on antimicrobial spectrum and mechanism of action, a distinction is made here between bacteriostatics and bactericides, fungistatics and fungicides, etc. Examples of important substances from these groups are benzalkonium chlorides, alkylarylsulfonates, halophenols and phenylmercury acetate. The terms antimicrobial action and antimicrobial active ingredient have, within the teaching of the invention, the meaning common in the art, which is described, for example, by K. H. Wallhäußer in "Praxis der Sterilisation, Desinfektion-Konservierung: Keimidentifizierung-Betriebshygiene" (5th Edition,—Stuttgart; New York: Thieme, 1995), it being possible to use all of the substances having antimicrobial action described there. Suitable antimicrobial active ingredients are preferably selected from the groups of alcohols, amines, aldehydes, antimicrobial acids or their salts, carboxylic esters, acid amides, phenols, phenol derivatives, diphenyls, diphenylalkanes, urea derivatives, oxygen acetals, nitrogen acetals and also oxygen and nitrogen formals, benzamidines, isothioazolines, phthalimide derivatives, pyridine derivatives, antimicrobial surfactant compounds, guanidines, antimicrobial amphoteric compounds, quinolines, 1,2-dibromo-2,4-dicyanobutane, iodo-2-propylbutyl carbamate, iodine, iodophors, peroxo compounds, halogen compounds, and any mixtures of the above.

The antimicrobial active ingredient may be selected from ethanol, n-propanol, isopropanol, 1,3-butanediol, phenoxyethanol, 1,2-propylene glycol, glycerol, undecylenic acid, benzoic acid, salicylic acid, dihydracetic acid, o-phenylphenol, N-methylmorpholinoacetonitrile (MMA), 2-benzyl-4-chlorophenol, 2,2'-methylenebis(6-bromo-4-chlorophenol), 4,4'-dichloro-2'-hydroxydiphenyl ether (dichlosan), 2,4,4'-trichloro-2'-hydroxydiphenyl ether (trichlosan), chlorohexidine, N-(4-chlorophenyl)-N-(3,4-dichlorophenyl)urea, N,N'-(1,10-decanediyldi-1-pyridinyl-4-ylidene)-bis(1-octanamine)dihydrochloride,N,N'-bis(4-chlorophenyl)-3,12-diimino-2,4,11,13-tetraazatetradecanedmieamideamide, glucoprotamines, antimicrobial surface-active quaternary compounds, guanidines including the bi- and polyguanidines, such as, for example, 1,6-bis(2-ethylhexylbiguanidohexane)dihydrochloride, 1,6-di-($N_1$,$N_1$'-phenyldiguanido-$N_5$,$N_5$')hexane tetrahydrochloride, 1,6-di-($N_1$,$N_1$'-phenyl-$N_1$,$N_1$-methyldiguanido-$N_5$,$N_5$')hexane dihydrochloride, 1,6-di-($N_1$,$N_1$'-o-chlorophenyldiguanido-$N_5$,$N_5$')hexane dihydrochloride, 1,6-di-($N_1$,$N_1$'-2,6-dichlorophenyldiguanido-$N_5$,$N_5$')hexane dihydrochloride, 1,6-di-[$N_1$,$N_1$'-beta-(p-methoxyphenyl)diguanido-$N_5$,$N_5$']hexane dihydrochloride, 1,6-di-($N_1$,$N_1$'-alpha-methyl-beta-phenyldiguanido-$N_5$,$N_5$')hexane dihydro-chloride, 1,6-di-($N_1$,$N_1$'-p-nitrophenylddguanido-$N_5$,$N_5$')hexane dihydrochloride, omega:omega-di-($N_1$,$N_1$'-phenyldiguanido-$N_5$,$N_5$')-di-n-propyl ether dihydrochloride, omega:omega'-di-($N_1$,$N_1$'-p-chlorophenyldiguanido-$N_5$,$N_5$')-di-n-propyl ether tetrahydrochloride, 1,6-di-($N_1$,$N_1$'-2,4-dichlorophenyldiguanido-$N_5$,$N_5$')hexane tetrahydrochloride, 1,6-di-($N_1$,$N_1$'-p-methylphenyl-diguanido-$N_5$,$N_5$')hexane dihydrochloride, 1,6-di-($N_1$,$N_1$'-2,4,5-trichlorophenyldiguanido-$N_5$,$N_5$')hexane tetrahydrochloride, 1,6-di-[$N_1$,$N_1$'-alpha-(p-chlorophenyl)ethyldiguanido-$N_5$,$N_5$']hexane dihydrochloride, omega:omega-di-($N_1$,$N_1$'-p-chlorophenyldiguanido-$N_5$,$N_5$')m-xylene dihydrochloride, 1,12-di-($N_1$,$N_1$'-p-chlorophenyldiguanido-$N_5$,$N_5$')dodecane dihydrochloride, 1,10-di-($N_1$,$N_1$'-phenyldiguanido-$N_5$,$N_5$')decane tetrahydrochloride, 1,12-di-($N_1$,$N_1$'-phenyldiguanido-$N_5$,$N_5$')dodecane tetrahydrochloride, 1,6-di-($N_1$,$N_1$'-o-chlorophenyldiguanido-$N_5$,$N_5$')hexane dihydrochloride, 1,6-di-($N_1$,$N_1$'-o-chlorophenyldiguanido-$N_5$,$N_5$')hexane tetrahydrochloride, ethylenebis(1-tolylbiguanide), ethylenebis(p-tolylbiguanide), ethylenebis(3,5-dimethylphenylbiguanide), ethylene-bis(p-tert-amylphenylbiguanide), ethylenebis(nonylphenylbiguanide), ethylenebis(phenylbiguanide), ethylenebis(N-butylphenylbiguanide), ethylene-bis(2,5-diethoxyphenylbiguanide), ethylene-bis(2,4-dimethylphenylbiguanide), ethylenebis(o-diphenylbiguanide), ethylenebis(mixed amyl naphthylbiguanide), N-butylethylenebis(phenylbiguanide), trimethylenebis(o-tolylbiguanide), N-butyl-trimethylbis(phenylbiguanide) and the corresponding salts such as acetates, gluconates, hydrochlorides, hydrobromides, citrates, bisulfites, fluorides, polymaleates, N-cocoalkylsarcosinates, phosphites, hypophosphites, perfluorooctanoates, silicates, sorbates, salicylates, maleates, tartrates, fumarates, ethylenediaminetetraacetates, iminodiacetates, cinnamates, thiocyanates, arginates, pyromellitates, tetracarboxybutyrates, benzoates, glutarates, monofluorophosphates, perfluoropropionates, and any mixtures thereof. Also suitable are halogenated xylene and cresol derivatives, such as p-chlorometacresol or p-chlorometaxylene, and natural antimicrobial active ingredients of plant origin (for example from spices or herbs), animal origin and microbial origin. Preference may be given to using antimicrobial surface-active quaternary compounds, a natural antimicrobial active ingredient of plant origin and/or a natural antimicrobial active ingredient of animal origin, most preferably at least one natural antimicrobial active ingredient of plant origin from the group comprising caffeine, theobromine and theophylline and essential oils such as eugenol, thymol and geraniol, and/or at least one natural antimicrobial active ingredient of animal origin from the group comprising enzymes such as milk protein, lysozyme and lactoperoxidase, and/or at least one antimicrobial surface-active quaternary compound having an ammonium, sulfonium, phosphonium, iodonium or arsonium group, peroxo compounds and chlorine compounds. It is also possible to use substances of microbial origin, the "bacteriocines".

The quaternary ammonium compounds (QACs) which are suitable as antimicrobial active ingredients have the general formula $(R^1)(R^2)(R^3)(R^4)N^+X^-$ where $R^1$ to $R^4$ are identical or different $C_1$-$C_{22}$-alkyl radicals, $C_7$-$C_{28}$-aralkyl radicals or heterocyclic radicals, where two, or in the case of an aromatic incorporation such as in pyridine, even three radicals, together with the nitrogen atom, form the heterocycle, for example a pyridinium or imidazolinium compound, and $X^-$ are halide ions, sulfate ions, hydroxide ions or similar anions. For optimal antimicrobial action, at least one of the radicals preferably has a chain length of from 8 to 18, in particular 12 to 16, carbon atoms.

QACs can be prepared by reacting tertiary amines with alkylating agents such as, for example, methyl chloride, benzyl chloride, dimethyl sulfate, dodecyl bromide, or else ethylene oxide. The alkylation of tertiary amines having one long alkyl radical and two methyl groups proceeds particularly readily, and the quaternization of tertiary amines having two long radicals and one methyl group can also be carried out with the aid of methyl chloride under mild conditions. Amines which have three long alkyl radicals or hydroxy-substituted alkyl radicals have low reactivity and are preferably quaternized using dimethyl sulfate.

Examples of suitable QACs are benzalkonium chloride (N-alkyl-N,N-dimethylbenzylammonium chloride, CAS No. 8001-54-5), benzalkone B (m,p-dichlorobenzyldimethyl-C12-alkylammonium chloride, CAS No. 58390-78-6), benzoxonium chloride (benzyldodecylbis(2-hydroxyethyl) ammonium chloride), cetrimonium bromide (N-hexadecyl-N,N-trimethylammonium bromide, CAS No. 57-09-0), benzetonium chloride (N,N-dimethyl-N-[2-[2-[p-(1,1,3,3-tetramethylbutyl)phenoxy]ethoxy]ethyl]benzylammonium chloride, CAS No. 121-54-0), dialkyldimethylammonium chlorides such as di-n-decyldimethylammonium chloride (CAS No. 7173-51-5-5), didecyldimethylammonium bromide (CAS No. 2390-68-3), dioctyldimethylammonium chloride, 1-cetylpyridinium chloride (CAS No. 123-03-5) and thiazoline iodide (CAS No. 15764-48-1), and mixtures thereof. Particularly preferred QACs are the benzalkonium chlorides having $C_8$-$C_{18}$-alkyl radials, in particular $C_{12}$-$C_{14}$-alkylbenzyldimethylammonium chloride.

Benzalkonium halides and/or substituted benzalkonium halides are commercially available, for example, as Barquat® ex Lonza, Marquat® ex Mason, Variquat® ex Witco/Sherex and Hyamine® ex Lonza, and Bardac® ex Lonza. Further commercially available antimicrobial active ingredients are N-(3-chloroallyl)hexaminium chloride such as Dowicide® and Dowicil® ex Dow, benzethonium chloride such as Hyamine® 1622 ex Rohm & Haas, methylbenzethonium chloride such as Hyamine® 10× ex Rohm & Haas, cetylpyridinium chloride such as cepacol chloride ex Merrell Labs.

The antimicrobial active ingredients are used in amounts of from 0.0001% by weight to 1% by weight, preferably from 0.001% by weight to 0.8% by weight, particularly preferably from 0.005% by weight to 0.3% by weight, and in particular from 0.01 to 0.2% by weight.

The agents may contain UV absorbers which attach to the treated textiles and improve the light stability of the fibers and/or the light stability of other formulation constituents. UV absorbers mean organic substances (light protection filters) which are able to absorb ultraviolet radiation and to emit the absorbed energy again in the form of radiation of longer wavelength, for example heat.

Compounds which have these desired properties are, for example, the compounds which are active via radiationless deactivation and derivatives of benzophenone having substituents in position(s) 2 and/or 4. Furthermore, also suitable are substituted benzotriazoles, acrylates which are phenyl-substituted in position 3 (cinnamic acid derivatives, with or without cyano groups in position 2), salicylates, organic Ni complexes and natural substances such as umbelliferone and the endogenous urocanic acid. Of particular importance are biphenyl and especially stilbene derivatives, as described, for example, in EP 0728749 A and commercially available as Tinosorb® FD or Tinosorb® FR ex Ciba. UV-B absorbers which may be mentioned are: 3-benzylidenecamphor or 3-benzylidenenorcamphor and derivatives thereof, for example 3-(4-methylbenzylidene)camphor, as described in EP 0693471 B1; 4-aminobenzoic acid derivatives, preferably 2-ethylhexyl 4-(dimethylamino)benzoate, 2-octyl 4-(dimethylamino)benzoate and amyl 4-(dimethylamino) benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylenes); esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives such as, for example, 2,4,6-trianilino-(p-carbo-2'-ethyl-1'-hexyloxy)-1,3,5-triazine and octyltriazone, as described in EP 0818450 A1, or dioctylbutamidotriazones (Uvasorb® HEB); propane-1,3-diones such as, for example, 1-(4-tert-butylphenyl)-3-(4'-methoxyphenyl)propane-1,3-dione; ketotricyclo(5.2.1.0)decane derivatives, as described in EP 0694521 B1. Further suitable are 2-phenylbenzimidazole-5-sulfonic acid and its alkali metal, alkaline earth metal, ammonium, alkylammonium, alkanolammonium and glucammonium salts; sulfonic acid derivatives of benzophenones, preferably 2-hydroxy-4-methoxybenzophenone-5-sulfonic acid and its salts; sulfonic acid derivatives of 3-benzylidenecamphor, such as, for example, 4-(2-oxo-3- bornylidenemethyl)benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in DE 19712033 A1 (BASF). The UV-A and UV-B filters may of course also be used in mixtures. In addition to said soluble substances, insoluble light protection pigments, namely finely dispersed, preferably nanoized, metal oxides or salts, are also suitable for this purpose. Examples of suitable metal oxides are, in particular, zinc oxide and titanium dioxide and also oxides of iron, zirconium, silicon, manganese, aluminum and cerium, and mixtures thereof. Salts which may be used are silicates (talc), barium sulfate or zinc stearate. The oxides and salts are already used in the form of the pigments for skin-care and skin-protective emulsions and decorative cosmetics. The particles here should have an average diameter of less than 100 nm, preferably between 5 and 50 nm, and in particular between 15 and 30 nm. They can have a spherical shape, but it is also possible to use particles which have an ellipsoidal shape or a shape deviating in some other way from the spherical form. The pigments may also be surface-treated, i.e. hydrophilicized or hydrophobicized. Typical examples are coated titanium dioxides such as, for example, titanium dioxide T 805 (Degussa) or Eusolex® T2000 (Merck); suitable hydrophobic coating agents are here preferably silicones and, particularly preferably, trialkoxyoctylsilanes or simethicones. Preference is given to using micronized zinc oxide. Further suitable UV light protection filters can be found in the review by P. Finkel in SÖFW-Journal 122 (1996), p. 543.

The UV absorbers are usually used in amounts of from 0.01% by weight to 5% by weight, preferably from 0.03% by weight to 1% by weight.

The ingredients usual for detergents and cleaning agents generally also include detersive and, respectively, cleaning-active enzymes. At the same time, detergents or cleaning agents which are also characterized by further enzymes in addition to a protein of the invention are preferred embodiments of the present invention. Examples of these include other proteases but also oxidoreductases, cutinases, esterases and/or hemicellulases, and particularly preferably lipases, amylases, cellulases and/or β-glucanases.

Enzymes such as proteases, amylases, lipases or cellulases have been used for decades as active components in detergents and cleaning agents. Their particular contribution to the washing and, respectively, cleaning performance of the agent in question is, in the case of protease, the ability to break down proteinaceous soilings, in the case of amylase, the breaking-down of starch-containing soilings, and, in the case of lipase, fat-cleaving activity. Cellulases are preferably used in detergents, in particular due to their contribution to the secondary washing performance of a detergent and due to their fiber action on textiles, in addition to their soil-removing, i.e. primary washing and cleaning performance. The particular hydrolysis products are attacked, dissolved, emulsified or suspended by the other detergent or cleaning agent components or are, due to their greater solubility, washed away with the wash liquor, advantageously resulting in synergistic effects between the enzymes and the other components.

Proteases can exert an effect on natural fibers, in particular on wool or silk, which is comparable to the contribution by cellulase to the secondary washing performance of an agent. Due to their action on the surface structure of such fabrics, they can exert a smoothing influence on the material and thereby counteract felting.

Other enzymes extend the cleaning performance of appropriate agents by their in each case specific enzyme performance. Examples of these include hemicellulases such as, for example, β-glucanases (WO 99/06515 A1 and WO 99/06516 A1), oxidoreductases such as, for example, laccases (WO 00/39306 A2) or pectin-dissolving enzymes (WO 00/42145 A1) which are used, in particular, in special detergents.

Enzymes suitable for use in agents of the invention are primarily those from microorganisms such as bacteria or fungi. They are obtained from suitable microorganisms in a manner known per se by means of fermentation processes which are described, for example, in German Laid-Open Specifications DE 1940488, and DE 2121397, the U.S. Pat. Nos. 3,623,957, 4,264,738, European patent application EP 006638 A2 and international patent application WO 91/02792 A1.

Particularly during storage, a protein of the invention and/or other proteins present may be protected by stabilizers from, for example, denaturing, decay or inactivation, for example by physical influences, oxidation or proteolytic cleavage.

One group of stabilizers is of reversible protease inhibitors which dissociate off when diluting the agent in the wash liquor. Benzamidine hydrochloride and leupeptin are established for this purpose. Frequently, borax, boric acids, boronic acids or salts or esters thereof are used, including especially derivatives with aromatic groups, for example, according to WO 95/12655 A1, ortho-substituted, according to WO 92/19707 A1, meta-substituted, and, according to U.S. Pat. No. 5,972,873, para-substituted phenylboronic acids, or salts or esters thereof. The applications WO 98/13460 A1 and EP 583534 B1 disclose peptide aldehydes, i.e. oligopeptides with reduced C terminus, specifically those of 2-50 monomers, for the reversible inhibition of detergent and cleaning agent proteases. The peptidic reversible protease inhibitors include, inter alia, ovomucoid (WO 93/00418 A1). For example, the application WO 00/01826 A2 discloses specific reversible peptide inhibitors of the protease subtilisin for use in protease-containing agents, and WO 00/01831 A2 discloses corresponding fusion proteins of protease and inhibitor.

Further enzyme stabilizers are amino alcohols such as mono-, di-, triethanol- and -propanolamine and mixtures thereof, aliphatic carboxylic acids up to $C_{12}$, as disclosed, for example, by the applications EP 0378261 B1 and WO 97/05227 A1, such as succinic acid, other dicarboxylic acids or salts of said acids. The application DE 19650537 A1 discloses end-group-capped fatty amide alkoxylates for this purpose. As disclosed in WO 97/18287 A1, particular organic acids used as builders are capable of additionally stabilizing a contained enzyme.

Lower aliphatic alcohols, but especially polyols such as, for example, glycerol, ethylene glycol, propylene glycol or sorbitol, are other frequently used enzyme stabilizers. Calcium salts are also used, such as, for example, calcium acetate or the calcium formate disclosed for this purpose in EP 028865 B2, and magnesium salts, for example according to EP 378262 B1.

Polyamide oligomers (WO 99/43780 A1) or polymeric compounds such as lignin (WO 97/00932 A1), water-soluble vinyl copolymers (EP 828762 B1) or, as disclosed in EP 702712 B1, cellulose ethers, acrylic polymers and/or polyamides stabilize the enzyme preparation inter alia against physical influences or pH fluctuations. Polyamine N-oxide-containing polymers (EP 587550 B1 and EP 581751 B1) simultaneously act as enzyme stabilizers and as color transfer inhibitors. Other polymeric stabilizers are the linear $C_8$-$C_{18}$ polyoxyalkylenes disclosed, in addition to other components, in WO 97/05227 A1. As in the applications WO 97/43377 A1 and WO 98/45396 A1, alkylpolyglycosides could stabilize the enzymic components of the agent of the invention and even increase their performance. Crosslinked N-containing compounds, as disclosed in WO 98/17764 A1, fulfill a double function as soil release agents and as enzyme stabilizers. Hydrophobic, nonionic polymer acts in a mixture together with other stabilizers, according to the application WO 97/32958 A1, in a stabilizing manner on a cellulase so that those or similar components may also be suitable for the enzyme essential to the invention.

As disclosed inter alia in EP 780466 A1, reducing agents and antioxidants increase the stability of the enzymes against oxidative decay. Sulfur-containing reducing agents are disclosed, for example, in EP 080748 B1 and EP 080223 B1. Other examples are sodium sulfite (EP 533239 B1) and reducing sugars (EP 656058 B1).

Frequently used are also combinations of stabilizers, for example of polyols, boric acid and/or borax in the application WO 96/31589 A1, the combination of boric acid or borate, reducing salts and succinic acid or other dicarboxylic acids in the application EP 126505 B1 or the combination of boric acid or borate with polyols or polyamino compounds and with reducing salts, as disclosed in the application EP 080223 B1. According to WO 98/13462 A1, the action of peptide-aldehyde stabilizers is increased by combination with boric acid and/or boric acid derivatives and polyols and, according to WO 98/13459 A1, still further enhanced by the additional use of calcium ions.

Agents containing stabilized enzyme activities are preferred embodiments of the present invention. Particular preference is given to those containing enzymes stabilized in a plurality of the ways indicated.

Since agents of the invention can be provided in any conceivable form, enzymes or proteins of the invention in any formulations appropriate for addition to the particular agents are respective embodiments of the present invention. Examples thereof include liquid formulations, solid granules or capsules.

The encapsulated form is a way of protecting the enzymes or other ingredients against other components such as, for example, bleaches, or of making possible a controlled release. Depending on their size, said capsules are divided into milli-, micro- and nanocapsules, microcapsules being particularly preferred for enzymes. Such capsules are disclosed, for example, in the patent applications WO 97/24177 A1 and DE 19918267 A1. A possible encapsulation method is to encapsulate the proteins, starting from a mixture of the protein solution with a solution or suspension of starch or a starch derivative, in this substance. The application WO 01/38471 A1 entitled "Verfahren zur Herstellung von mikroverkapselten Enzymen" [Method for preparing microencapsulated enzymes] describes such an encapsulation method.

In the case of solid agents, the proteins may be used, for example, in dried, granulated and/or encapsulated form. They may be added separately, i.e. as a separate phase, or together with other components in the same phase, with or without compaction. If microencapsulated enzymes are to be processed in solid form, it is possible to remove the water from the aqueous solutions resulting from the work-up by using methods known in the prior art, such as spray drying, removing by centrifugation or resolubilizing. The particles obtained in this way are usually between 50 and 200 μm in size.

It is possible to add to liquid, gel-like or paste-like agents of the invention the enzymes and also the protein of the invention, starting from protein recovery carried out according to the prior art, and preparation in a concentrated aqueous or nonaqueous solution, suspension or emulsion, but also in gel form or encapsulated or as dried powder. Such detergents or cleaning agents of the invention are usually prepared by simply mixing the ingredients which may be introduced as solids or as solution into an automated mixer.

Apart from the primary washing performance, the proteases present in detergents may further fulfill the function of activating, or, after an appropriate period of action, inactivating other enzymic components by proteolytic cleavage. Comparable regulatory functions are also possible via the enzyme of the invention. Another embodiment of the present invention relates to those agents containing capsules of protease-sensitive material, which capsules are hydrolyzed, for example, by proteins of the invention at the intended time and release their contents. A comparable effect may also be achieved in other multi-phase agents.

Agents for the treatment of textile raw materials or for textile care, which are characterized in that they contain any of the proteolytic enzymes defined above, either alone or in addition to other ingredients, in particular for fibers or textiles containing natural components and, very particularly, for those containing wool or silk are a further embodiment of the invention.

Natural fibers in particular, such as wool or silk, for example, are distinguished by a characteristic, microscopic surface structure. Said surface structure can, in the long term, result in undesired effects such as, for example, felting, as discussed by way of example for wool in the article by R. Breier in *Melliand Textilberichte* from Mar. 1, 2000 (p. 263). In order to avoid such effects, the natural raw materials are treated with agents of the invention which contribute, for example, to smoothing the flaked surface structure based on protein structures and thereby counteract felting. Agents of this kind for fibers or textiles containing natural components and, very particularly, containing wool or silk are a particularly preferred embodiment.

In one preferred embodiment, the agent containing a protease of the invention is designed in such a way that it can be used regularly as a care agent, for example by adding it to the washing process, applying it after washing or independently of the washing. The desired effect is to obtain a smooth surface structure of the textile and/or to prevent and/or reduce damage to the fabric.

Methods for machine cleaning of textiles or of hard surfaces, which methods are characterized in that a proteolytic enzyme of the invention becomes active in at least one of the method steps, are a separate subject matter of the invention.

Methods for machine cleaning of textiles are generally distinguished by several method steps comprising applying various cleaning-active substances to the material to be cleaned and, after the time of action, washing them off, or by the material to be cleaned being treated in any other way with a cleaning agent or a solution of said agent. The same applies to methods for machine cleaning of any other materials as textiles which are classified under the term hard surfaces. It is possible to add proteins of the invention to at least one of the method steps of such methods, which methods then become embodiments of the present invention.

Preference is given to methods in which an enzyme of the invention is used in an amount of from 40 µg to 4 g and, more preferably, from 50 µg to 3 g, from 100 µg to 2 g, from 200 µg to 1 g and, particularly preferably, from 400 µg to 400 mg per application.

Since the enzyme of the invention already by nature possesses a protein-dissolving activity and also exhibits said activity in media which otherwise have no cleaning power, such as, for example, in straight buffer, an individual partial step of such a method for machine cleaning of textiles may consist of applying, if desired in addition to stabilizing compounds, salts or buffer substances, the enzyme of the invention as single cleaning-active component. This is a particularly preferred embodiment of the present invention.

Methods for the treatment of textile raw materials or textile care, which methods are characterized in that a proteolytic enzyme of the invention becomes active in at least one of the method steps, are preferred embodiments of this subject matter of the invention. They may be, for example, methods in which materials are prepared for use in textiles, for example for anti-felt finishing, or, for example, methods which add a care component to the cleaning of worn textiles. Due to the above-described action of proteases on particular fabrics, particular embodiments comprise textile raw materials or textiles containing natural components, in particular containing wool or silk.

The use of a proteolytic enzyme of the invention for cleaning textiles or hard surfaces is a separate subject matter of the invention, since enzymes of the invention may be used, in particular according to the above-described methods, in order to remove proteinaceous soilings from textiles or from hard surfaces. The use outside a machine-based method, for example in manual laundry or manual removal of stains from textiles or from hard surfaces, are preferred embodiments.

Preference is given to using an enzyme of the invention in an amount of from 40 µg to 4 g and, more preferably, from 50 µg to 3 g, from 100 µg to 2 g, from 200 µg to 1 g and, particularly preferably, from 400 µg to 400 mg per application.

The use of a proteolytic enzyme of the invention for activating or deactivating ingredients of detergents or cleaning agents is a preferred embodiment of this subject matter of the invention, since protein components of detergents or cleaning agents, as is known, can be inactivated by the action of a protease. The present invention relates to specifically using this otherwise rather undesired effect. It is likewise possible that proteolysis actually activates another component, for example if said component is a hybrid protein of the actual enzyme and the corresponding inhibitor, as disclosed, for example, in the application WO 00/01831 A2. Another example of a regulation of this kind is one in which an active component, in order to protect or control its activity, has been encapsulated in a material susceptible to proteolytic attack. Proteins of the invention can thus be used for inactivation reactions, activation reactions or release reactions.

Despite their diversity, all other technical methods, uses and corresponding agents outside the problem of washing and cleaning are combined into one subject matter of the invention hereinbelow, as long as they are characterized by a protein of the invention. This compilation is not to be understood as an exclusive listing, but lists the most important, currently discernible possible uses of proteases of the invention. If other technical fields prove able to be developed by using proteases of the invention, then said fields are included within the scope of protection of the present invention.

The use of a proteolytic enzyme of the invention for biochemical or molecular-biological analysis, in particular within the framework of an enzymic analytical method, is subject matter of the invention. According to the invention and according to Rompp, "Lexikon Chemie" (Version 2.0, Stuttgart/New York: Georg Thieme Verlag, 1999), enzymic analysis means any biochemical analysis which uses specific enzymes or substrates in order to determine, on the one hand, the identity or concentration of substrates or, on the other hand, the identity or activity of enzymes. Areas of application are any areas of work related to biochemistry. A preferred embodiment of this subject matter of the invention is the use for determining the terminal groups in a sequence analysis.

The use of a proteolytic enzyme of the invention for the preparation, purification or synthesis of natural substances or biological valuable substances is subject matter of the invention. Thus, it may be necessary, for example, in the course of purifying natural substances or biological valuable substances, to remove from said substances protein contaminations, examples of which are low molecular weight compounds, any cellular constituents or storage substances or proteins. This can be carried out both on the laboratory scale and the industrial scale, for example after biotechnological production of a valuable substance.

A proteolytic enzyme of the invention is used for the synthesis of proteins or other low molecular weight chemical compounds by reversing the reaction which they catalyze by nature, for example when it is intended to link protein fragments to one another or to bind amino acids to a compound which is not predominantly composed of protein. Possible uses of this kind are introduced, for example, in the application EP 380362 A1.

The use of a proteolytic enzyme of the invention for the treatment of natural raw materials is another embodiment of this subject matter of the invention, if it is intended to remove protein contaminations from said raw materials, which mean primarily raw materials which are obtained non-microbiologically, for example those from agriculture.

A preferred embodiment is the use for the treatment of surfaces, and very particularly in a method for the treatment of the economically important raw material leather. Thus, water-soluble proteins are removed from the hide material with the aid of proteolytic enzymes during the tanning process, in particular in the step of alkaline steep (Römpp, "Lexikon Chemie", Version 2.0, Stuttgart/New York: Georg Thieme Verlag, 1999). Proteases of the invention are suitable for this, in particular under alkaline conditions and in the presence of denaturing agents.

The use of a proteolytic enzyme of the invention for the obtainment or treatment of raw materials or intermediates in the manufacture of textiles is another embodiment of this subject matter of the invention. An example thereof is the processing of cotton from which capsule components need to be removed in a process referred to as sizing; another example is the treatment of wool; the processing of raw silk is also similar. Enzymic methods are superior to comparable chemical methods, in particular with respect to their environmental compatibility.

In a preferred embodiment, proteins of the invention are used for removing protective layers from textiles, in particular from intermediate products or valuable substances, or smoothing their surface, before further treatment in a subsequent processing step.

The use of a protein of the invention for the treatment of textile raw materials or for textile care, in particular for the treatment of surfaces of wool or silk or of wool- or silk-containing mixed textiles is another embodiment of this subject matter of the invention. This applies both to the production of such textiles and to the care during usage, for example in connection with the cleaning of textiles (see above).

The use of a proteolytic enzyme of the invention for the treatment of photographic films, in particular for removing gelatin-containing or similar protective layers, is another embodiment of this subject matter of the invention, since films such as, for example, X-ray films, are coated with such protective layers, in particular those made of silver salt-containing gelatin emulsions, which films need to be removed from the backing material after exposure. For this, proteases of the invention may be used, in particular under alkaline or slightly denaturing reaction conditions.

The use of a proteolytic enzyme of the invention for preparing food or animal feed is a separate subject matter of the invention. Thus proteases have been used for the preparation of food from time immemorial. An example of this is the use of rennet for the maturing process of cheese or other milk products. A protein of the invention may be added to or be used to completely carry out such processes. Carbohydrate-rich food or food raw materials for non-nutritional purposes, such as, for example, flour or dextrin, may also be treated with appropriate proteases in order to remove accompanying proteins from them. A protease of the invention is suitable for those applications, too, in particular if they are to be carried out under alkaline or slightly denaturing conditions.

This applies accordingly for the preparation of animal feed. In addition to a complete removal of proteins, it may also be of interest here to treat the proteinaceous starting substances or substance mixtures with proteases only for a short time in order to render them more readily digestible for domestic animals.

In another embodiment of this subject matter of the invention, proteins of the invention may be used for cosmetic purposes. Thus, cosmetic agents containing a proteolytic enzyme of the invention, cosmetic methods incorporating a proteolytic enzyme of the invention and the use of a proteolytic enzyme of the invention for cosmetic purposes, in particular within the framework of corresponding methods or in corresponding agents, are claimed.

Since proteases also play a crucial part in the desquamation of human skin (T. Egelrud et al., *Acta Derm. Venerol.*, volume 71 (1991), pp. 471-747), proteases are accordingly also used as bioactive components in skincare products in order to support degradation of the desmosome structures increasingly present in dry skin, for example according to the applications WO 95/07688 A1 and WO 99/18219 A1. WO 97/07770 A1, for example, describes the use of subtilisin proteases, in particular of the *B. lentus* alkaline protease variants described above, for cosmetic purposes. Proteases of the invention, in particular those whose activity is controlled, for example, after mutagenesis or due to addition of appropriate substances interacting with them, are also suitable as active components in skin- or hair-cleaning compositions or care compositions. Particular preference is given to those preparations of said enzymes, which, as described above, are stabilized, for example by coupling to macromolecular supports (compare U.S. Pat. No. 5,230, 891), and/or are derivatized by point mutations at highly allergenic positions so that their compatibility with human skin is increased.

Accordingly, the use of proteolytic enzymes of this kind for cosmetic purposes, in particular in appropriate agents such as, for example, shampoos, soaps or washing lotions or in care compositions provided, for example, in the form of creams, is also included in this subject matter of the invention. The use in a peeling medicament is also included in this claim.

Thus, in addition to the variant itself and certain agents incorporating the variant, protease variants of the present invention are useful in a variety of embodiments of the present invention, including compositions and methods for: 1) activating or deactivating ingredients of detergents or cleaning agents; 2) biochemically analyzing or for synthesizing low molecular weight compounds or proteins; 3) preparing, purifying or synthesizing natural substances or biological valuable substances; 4) treating natural raw materials, in particular for the treatment of surfaces, very particularly in a method for the treatment of leather; 5) in textile manufacture, particularly removing protective layers on fabric; 6) treating wool or silk or of wool- or silk-containing mixed textiles; 7) treating photographic films, in particular for removing gelatin-containing or similar protective layers; 8) preparing food or animal feed; or 9) preparing a cosmetic including the variant.

EXAMPLES

Example 1

Generation of the Proteases of the Invention

All molecular-biological working steps follow standard methods as indicated, for example, in the manual by Fritsch, Sambrook and Maniatis "Molecular cloning: a laboratory manual", Cold Spring Harbour Laboratory Press, New York, 1989, or in international patent application WO 92/21760 A1.

Construction of the Mutagenesis Vector

The mutagenesis was carried out starting from the protease variant *B. lentus* alkaline protease M131 having the amino acid sequence indicated in SEQ ID No. 2. This variant is described in WO 92/21760 A1 and the strain according to this application, which produces it, has been deposited with the American Type Culture Collection, Rockville, Md., USA under the name *Bacillus licheniformis* ATCC 68614. This strain contains the gene on plasmid pCB56M131 which replicates in Bacillus in an expression cassette comprising the promoter, the ribosomal binding site and the ATG start codon and the 22 amino-terminal amino acids of the alkaline protease from *Bacillus licheniformis* ATCC 53926 which are fused to the prepro-protein and the mutated sequence of Bacillus lentus DSM 5483 alkaline protease. The variant *B. lentus* alkaline protease M131 having the amino acid sequence indicated in SEQ ID No. 2 has the following mutations, compared to the native sequence: S3T, V4I, A188P, V193M, V199I.

For mutagenesis, the entire expression cassette was excised by means of restriction enzymes Bam HI and Sac I and cloned into the pUC18 vector (Amersham Pharmacia Biotech, Freiburg, Germany) which had likewise been cut with Bam HI and Sac I. The pUC18M131 vector thus obtained was then used to carry out the following mutagenesis steps. FIG. 2 depicts the pUC18M131 vector. The DNA fragment containing the expression cassette for *B. lentus* alkaline protease M131 is documented in SEQ ID NO. 1; SEQ ID NO. 2 depicts the amino acid sequence derived therefrom. The Bam HI-SacI fragment depicted in SEQ ID NO. 1 extends over positions 1 to 1771 in the pUC18M131 vector depicted in FIG. 2; the remaining vector regions are identical to those of the starting plasmid pUC18.

Mutagenesis

First, the original sequence of *Bacillus lentus* DSM 5483 alkaline protease at positions 188 and 193 was restored using the QuikChange® method from Stratagene (La Jolla, Calif., USA) according to the manufacturer's instructions. According to this system, a mutated plasmid was generated in a polymerase reaction using two complementary primers containing the mutation in each case. After digesting the starting plasmid by means of DpnI, as stipulated in the QuikChange® method, the reaction mixture was transformed into *E. coli* XL-1 blue. The clones obtained thereby which contain the gene of interest located on a plasmid can, where appropriate, be readily identified by means of a restriction cleavage site introduced via the mutation, with checking by DNA sequencing according to the chain termination method with the aid of a conventional kit being possible in each case. The same method was also used for all subsequent mutagenesis steps.

The triplet coding for the amino acid in position 188, CCA (proline), was converted to GCC (alanine) by using the two primers 5'-TCA CAG TAT GGC GCC GGG CTT GAC ATT-3' (SEQ ID NO:7) and 5-AAT GTC AAG CCC GGC GCC ATA CTG TGA-3' (SEQ ID NO:8), which contain, directly adjacent to the mutation, an Nar I restriction cleavage site which does not alter the amino acid sequence.

The triplet coding for the amino acid at position 193, ATG (methionine), was converted to ATT (isoleucine) by using the two primers 5'-GGG CTT GAC ATT GTG GCA CCC GGG GTA AAC-3' (SEQ ID NO:10) and 5'-GTT TAC CCC GGG TGC CAC AAT GTC AAG CCC-3' (SEQ ID NO:10) which contain, directly adjacent to the mutation, an Xma CI restriction site which does not alter the amino acid sequence.

A clone containing the doubly mutated plasmid then provided the template for subsequent mutation of the triplet at position 61, GGG (glycine) to GCT (alanine). For this purpose, the two complementary primers with the sequences 5'-CAA GAT GGG AAT GCT CAT GGC ACG CAT-3' (SEQ ID NO:11) and 5'-ATG CGT GCC ATG AGC ATT CCC ATC TTG-3' (SEQ ID NO:12) were used. Thus, the gene for the variant *B. lentus* alkaline protease S3T/V4I/G61A/V199I was already present.

Finally, starting from this mutant, the second particularly preferred variant was generated by mutating the leucine at position 211 to the amino acid aspartate. For this purpose, the two complementary primers with the sequences 5'-ACG TAT GCC AGC GAC AAC GGT ACA TCG-3' (SEQ ID NO:13) and 5'-CGA TGT ACC GTT GTC GCT GGC ATA CGT-3' (SEQ ID NO:14) were used. The clones obtained were then checked by DNA sequencing.

The DNA sequence of the S3T/V4I/G61A/V199I mutant gene coding for the complete protease is indicated in the sequence listing under SEQ ID No. 3. The amino acid sequence indicated in the sequence listing under SEQ ID No. 4 can be derived therefrom. The DNA sequence and protein sequence of the mutant S3T/V4V/G61A/V199I/L211D are described in the sequence listing under SEQ ID No. 5 and SEQ ID No. 6, respectively. Due to these positions deviating from the wild-type enzyme of *B. lentus* DSM 5483, these variants are referred to as *B. lentus* alkaline protease S3T/V4I/G61A/V199I and, respectively, as *B. lentus* alkaline protease S3T/V4I/G61A/V199I/L211D.

Expression of the Mutants and Protease Preparation

The expression cassette containing the mutated sequence was cloned back as Bam HI-Sac I fragment into the pCB56M131 vector, replacing the fragment depicted in SEQ ID NO. 1, and transformed into *Bacillus subtilis* DB104. The *Bacillus subtilis* DB 104 strain has the genotype his, nprR2, nprE18, aprA3 (Kawamura, F. and Doi, R. H. (1984), J. Bacteriol., volume 160, pages 442-444). The DNA was transformed into *Bacillus* according to the variant described in WO 91/02792 of the protoplast method originally developed by Chang and Cohen (1979; *Molec. Gen. Genet.*, volume 168, pages 111-115).

Protease-positive clones obtained thereby were, after checking, incubated in 500 ml of MLBSP medium (10 g/l casitone; 20 g/l tryptone, 10 g/l yeast extract, all from Becton Dickinson, Cockeysville; 5 g/l NaCl; 27 g/l sodium succinate; 100 mg/l $MgSO_4$*7 $H_2O$; 75 mg/l $CaCl_2$*2 $H_2O$; 0.5 µM $MnCl_2$; 0.5 µM $FeSO_4$; 2% (w/v) glucose; 50 mM PIPES buffer (from a 1 M stock solution, pH 7.2); 75 mM $KPO_4$ (from a 1.5 M stock solution, pH 7.0); pH=7.0, adjusted with KOH—and 10 µg/ml tetracycline) in 2000 ml shaker flasks at 37° C. and 200 revolutions per minute for 72 h. The supernatant obtained, after removing the cells by centrifugation, was used for the experiments below, after determining the protease activity (according to the methods described in *Tenside*, volume 7 (1970), pp. 125-132).

Example 2

Textiles which had been soiled in a standardized manner and obtained from the Eidgenössische Material-Prüfungs- und-Versuchsanstalt, St. Gallen, Switzerland (EMPA) or the Wäschereiforschungsanstalt, Krefeld, Germany, were used for the following examples. The following stains/textiles were used in example 2: A (blood/milk/soot on cotton), B (blood/milk/ink on cotton), C (blood/milk/ink on a polyester-cotton blend) and D (egg/soot on cotton).

This test material was used to test the washing performances of various detergent formulations, using a launderometer. For this purpose, the liquor ratio was set in each case to 1:12, and washing was carried out at a temperature of 40° C. for 30 min. The dosage was 5.88 g of the particular detergent per 1 of wash liquor. The water hardness was 16° German hardness.

The control detergent used was a basic detergent formulation of the following composition (all values in percent by weight): 4% linear alkyl benzenesulfonate (sodium salt), 4% $C_{12}$-$C_{18}$-fatty alcohol sulfate (sodium salt), 5.5% $C_{12}$-$C_{18}$-fatty alcohol with 7 EO, 1% sodium soap, 11% sodium carbonate, 2.5% amorphous sodium disilicate, 20% sodium perborate tetrahydrate, 5.5% TAED, 25% zeolite A, 4.5% polycarboxylate, 0.5% phosphonate, 2.5% foam inhibitor granules, 5% sodium sulfate, rest: water, optical brighteners, salts. Said formulation was admixed for the different series of experiments with the following proteases in such a way that in each case a final concentration of 2.250 PE of proteolytic activity per 1 wash liquor was obtained: *B. lentus* alkaline protease F49 (WO 95/23221; manufacturer: Biozym, Kundl, Austria), Savinase® (Novozymes A/S, Bagsvaerd, Denmark) and the protease of the invention, *B. lentus* alkaline protease S3T/V4I/G61A/V199I/L211D.

After washing, the degree of whiteness of the washed textiles was measured in comparison to that of barium sulfate, which had been normalized to 100%. The measurement was carried out in a Datacolor SF500-2 spectrometer at 460 nm (UV blocking filter 3), 30 mm diaphragm, without gloss, D65 illuminant, 10°, d/8°. Table 2 below summarizes the results obtained as percent reflectance, i.e. as percentages in comparison with barium sulfate together with the respective starting values. The averages of in each case 4 measurements are listed. They allow an immediate conclusion to be drawn about the contribution of the enzyme present on the washing performance of the agent used.

TABLE 2

| Basic detergent with | A | B | C | D |
|---|---|---|---|---|
| starting value | 22.9 | 13.0 | 11.3 | 26.4 |
| Control without protease | 34.1 | 18.5 | 15.1 | 42.4 |
| B. lentus alkaline protease S3T/V4I/G61A/V199I/L211D | 45.1 | 33.5 | 42.5 | 72.6 |
| B. lentus alkaline protease F49 | 40.1 | 28.6 | 26.8 | 71.3 |
| Savinase ® | 43.0 | 30.5 | 29.5 | 48.6 |
| standard deviation | 0.7 | 0.7 | 1.2 | 0.9 |

The data show that B. lentus alkaline protease S3T/V4I/G61A/V199I/L211D exhibits distinctly superior washing performances on all stains than the established proteases B. lentus alkaline protease F49 and Savinase®.

Example 3

Cotton textiles having the same soilings as in Example 2, A, B and C, were studied in the same way as in Example 2. The difference was that in this example the protease of the invention, B. lentus alkaline protease S3T/V4I/G61A/V199I, was compared with the variant B. lentus alkaline protease S3T/V4I/V199I and the likewise known proteases B. lentus alkaline protease F49 and Savinase®, with otherwise identical detergent formulations. They were again concentrated in such a way that in each case a final concentration of 2 250 PE of proteolytic activity per 1 wash liquor was obtained, with the temperature again being 40° C.

The measurement and evaluation of the experimental series were likewise carried out as in Example 2. Table 3 below shows the results obtained.

TABLE 3

| Basic detergent with | A | B | C |
|---|---|---|---|
| starting value | 13.6 | 13.2 | 11.1 |
| Control without protease | 24.5 | 17.8 | 14.4 |
| B. lentus alkaline protease S3T/V4I/G61A/V199I | 36.2 | 37.0 | 46.9 |
| B. lentus alkaline protease S3T/V4I/V199I | 31.6 | 33.1 | 39.6 |
| B. lentus alkaline protease F49 | 28.7 | 28.6 | 25.9 |
| Savinase ® | 29.0 | 30.8 | 29.0 |
| standard deviation | 1.0 | 0.8 | 1.3 |

Comparison of the two variants B. lentus alkaline protease S3T/V4I/G61A/V199I and B. lentus alkaline protease S3T/V4I/V199I reveals that replacing the amino acid glycine at position 61 with the aliphatic amino acid alanine has improved the performance of the enzyme in a detergent formulation, with respect to various soilings and on various fabrics. It thus clearly surpasses the established proteases B. lentus alkaline protease F49 and Savinase®.

Example 4

Vessels with hard, smooth surfaces were contacted in a standardized way with (A) soft-boiled egg and (B) egg/milk and washed at 45° C. using the standard program of a domestic dishwasher type Miele® G 676. 20 g of dishwashing agent were used per dishwashing run; the water hardness was 16° German hardness.

The dishwashing agent used had the following basic formulation (all values in each case in percent by weight): 55% sodium tripolyphosphate (calculated as anhydrous), 4% amorphous sodium disilicate (calculated as anhydrous), 22% sodium carbonate, 9% sodium perborate, 2% TAED, 2% nonionic surfactant, rest: water, dyes, perfume. This basic formulation was admixed for the various experiments, with identical activities, with the various proteases, B. lentus alkaline protease F49, Savinase® and the protease variant of the invention, B. lentus alkaline protease S3T/V4I/G61A/V199I/L211D, in such a way that in each case an activity of 10000 PE per dishwashing run was obtained. This corresponded in each case to approx. 0.1 mg of protease protein per g of cleaning agent concentrate.

After washing, the removal of the soilings was determined gravimetrically in percent. For this purpose, the difference between the weight of the soiled and then rinsed vessel and the starting weight of said vessel was related to the weight difference of the unwashed vessel to the starting weight. This relation can be regarded as percent removal. The results obtained are summarized in Table 4 below which lists the averages of in each case 9 measurements. They allow an immediate conclusion to be drawn about the contribution of the enzyme present to the washing performance of the agent used.

TABLE 4

| Basic detergent with | A | B |
|---|---|---|
| B. lentus alkaline protease S3T/V4I/G61A/V199I/L211D | 29.8 | 33.2 |
| B. lentus alkaline protease F49 | 26.2 | 22.4 |
| Savinase ® | 12.5 | 12.0 |

These results show that the cleaning performance of the B. lentus alkaline protease of the invention, S3T/V4I/G61A/V199I/L211D, in machine dishwashing agents is superior, but at least equal, to that of the other proteases tested; and this even at a comparatively low activity used.

Example 5

Vessels with hard, smooth surfaces were contacted with the same soilings as in the previous examples and additionally with the soiling D (lasagna) and washed in the same way and again at 45° C. The difference was that in this example the protease of the invention, B. lentus alkaline protease S3T/V4I/G61A/V199I, was compared with the variant B. lentus alkaline protease S3T/V4I/V199I and the likewise known proteases B. lentus alkaline protease F49 and Savinase®, with otherwise identical cleaning agent formulations. They were again concentrated in such a way that in each case a proteolytic activity of 10000 PE per dishwashing run was obtained. The measurements were likewise carried out as described in the previous example. Table 5 summarizes the results.

TABLE 5

| Basic detergent with | A | B | C | D |
|---|---|---|---|---|
| B. lentus alkaline protease S3T/V4I/G61A/V199I | 20.3 | 17.3 | 72.3 | 82.3 |
| B. lentus alkaline protease S3T/V4I/V199I | 19.3 | 15.5 | 61.6 | 77.1 |

TABLE 5-continued

| Basic detergent with | A | B | C | D |
|---|---|---|---|---|
| B. lentus alkaline protease F49 | 28.5 | 23.0 | 69.3 | 74.5 |
| Savinase ® | 13.6 | 13.5 | 67.5 | 64.5 |

The data show that the contribution of the variant B. lentus alkaline protease S3T/V4I/G61A/V199I to the cleaning performance is superior also in cleaning agents to that of the variant B. lentus alkaline protease S3T/V4I/V199I, with respect to various soilings. This performance increase can be attributed only to the change at position 61. With respect to all the soilings tested, a better performance than that of Savinase® is obtained; and, with respect to the soilings C and D, a better performance than that of the B. lentus alkaline protease F49 is also obtained.

Example 6

As in Example 4, vessels were contacted with the same soilings according to a standard and washed in the same way with in each case the same cleaning agent formulations, again at 45° C. The only difference was the fact that in each case 20000 PE of the particular proteases were used. This corresponded in each case to approx. 0.2 mg of protease in the cleaning agent concentrate. The results of the measurements, which were obtained in the same way as in Example 5, are listed in Table 6 below.

TABLE 6

| Basic detergent with | A | B |
|---|---|---|
| B. lentus alkaline protease S3T/V4I/G61A/V199I/L211D | 35.3 | 39.1 |
| B. lentus alkaline protease F49 | 33.2 | 32.7 |
| Savinase ® | 12.4 | 14.0 |

With higher protease activities used too, the higher contribution of the protease of the invention to the overall cleaning performance of the particular agent in comparison with the proteases established for machine dishwashing agents, B. lentus alkaline protease F49 and Savinase®, is also evident.

Example 7

In the same way as in the previous example, vessels having the soilings B and D were once more studied with cleaning agent formulations containing the protease of the invention, B. lentus alkaline protease S3T/V4I/G61A/V199I, the variant B. lentus alkaline protease S3T/V4I/V199I, the B. lentus alkaline protease F49 or Savinasee. They were concentrated in such a way that in each case a proteolytic activity of 20000 PE per dishwashing run was obtained. The temperature was 45° C. The measurements were likewise carried out as described in Example 5. The results obtained are listed in Table 7.

TABLE 7

| Basic detergent with | B | D |
|---|---|---|
| B. lentus alkaline protease S3T/V4I/G61A/V199ID | 34.7 | 89.4 |
| B. lentus alkaline protease S3T/V4I/V199ID | 30.7 | 88.4 |
| B. lentus alkaline protease F49 | 40.6 | 87.5 |
| Savinase ® | 14.0 | 80.6 |

The data show that also at higher concentrations the contribution of the variant B. lentus alkaline protease S3T/V4I/G61A/V199I to the cleaning performance in cleaning agents is superior to that of the variant B. lentus alkaline protease S3T/V4I/V199I, with respect various soilings. This performance increase can be attributed only to the change at position 61. With respect to all the soilings tested, a sometimes distinctly superior performance is obtained than for Savinase®; and with respect to soiling D, a performance superior to that of B. lentus alkaline protease F49 is also obtained.

The disclosures of each patent, patent application, and publication cited or described in this document are hereby incorporated herein by reference, in their entireties.

Various modifications of the invention, in addition to those described herein, will be apparent to those skilled in the art from the foregoing description. Such modifications are also intended to fall within the scope of the appended claims.

The invention claimed is:

1. A modified alkaline protease comprising:

a substitution of a threonine for the residue at the position corresponding to position 3 of the mature protease of SEQ ID NO:2;

a substitution of an isoleucine for the residue at the position corresponding to position 4 of the mature protease of SEQ ID NO:2;

a substitution of an alanine, a threonine, or an arginine for the residue at the position corresponding to position 61 of the mature protease of SEQ ID NO:2; and a substitution of an isoleucine for the residue at the position corresponding to position 199 of the mature protease of SEQ ID NO:2, wherein the modified alkaline protease is a mature protease comprising the gaps in amino acid sequence relative to the amino acid sequences of subtilisin BPN' and subtilisin Carlsberg depicted in FIG. 1.

2. The modified alkaline protease of claim 1 further comprising a substitution of an aspartic acid for the residue at the position corresponding to position 211 of the mature protease of SEQ ID NO:2.

3. The modified alkaline protease of claim 1, wherein the alkaline protease is derived from *Bacillus lentus* DSM 5483 subtilisin.

4. The modified alkaline protease of claim 3, wherein the mature protease has the amino acid sequence from position 1 through position 269 of SEQ ID NO:4.

5. The modified alkaline protease of claim 3, wherein the mature protease has the amino acid sequence from position 1 through position 269 of SEQ ID NO:6.

6. The modified alkaline protease of claim 1 having a substitution of an alanine, a threonine, or an arginine for the residue at the position corresponding to position 61 of the mature protease of SEQ ID NO:2, said mature protease having the amino acid sequence from position 1 through position 269 of SEQ ID NO:2.

7. A nucleic acid molecule encoding the modified alkaline protease of claim 1.

8. A vector comprising the nucleic acid molecule of claim 7.

9. The vector of claim 8, wherein the vector is a cloning vector or an expression vector.

10. A host cell comprising the vector of claim 8.

11. A host cell that expresses or can be induced to express the modified alkaline protease of claim 1.

12. The host cell of claim 11, wherein the cell secretes the modified alkaline protease into the surrounding medium.

13. The host cell of claim 11, wherein the cell is a Gram-positive bacterium.

14. The host cell of claim 11, wherein the cell is a *Bacillus lentus, Bacillus licheniformis, Bacillus amyloliquefaciens, Bacillus subtilis*, or *Bacillus alcalophilus* cell.

15. The host cell of claim 11, wherein the cell is a eukaryotic cell that posttranslationally modifies the modified alkaline protease.

16. A composition comprising the modified alkaline protease of claim 1 and a detergent or a cleaning agent.

17. The composition of claim 16, wherein the modified alkaline protease is present in an amount of from 2 µg to 20 mg per gram of the composition.

18. The composition of claim 16, further comprising at least one of an additional protease, an amylase, a cellulase, a hemicellulase, an oxidoreductase, or a lipase.

19. A method for cleaning a textile or surface comprising providing a modified alkaline protease of claim 1 and activating the modified alkaline protease.

* * * * *

SEQUENCE LISTING

<160> NUMBER OF SEQ ID NOS: 21

<210> SEQ ID NO 1
<211> LENGTH: 1773
<212> TYPE: DNA
<213> ORGANISM: Bacillus licheniformis ATCC 68614
<220> FEATURE:
<221> NAME/KEY: CDS
<222> LOCATION: (233)..(1372)
<220> FEATURE:
<221> NAME/KEY: mat_peptide
<222> LOCATION: (566)..(1372)

<400> SEQUENCE: 1

```
ggatcctcgg gacctctttc cctgccaggc tgaagcggtc tattcatact ttcgaactga      60 acattttct aaaacagtta ttaataacca aaaaatttta aattggtcct ccaaaaaaat     120
```

-continued

```
aggcctacca tataattcat ttttttttcta taataaatta acagaataat tggaatagat      180
tatattatcc ttctatttaa attattctga ataaagagga ggagagtgag ta atg          235
                                                           Met atg agg aaa aag agt ttt tgg ctt ggg atg ctg acg gcc ttc atg             280
Met Arg Lys Lys Ser Phe Trp Leu Gly Met Leu Thr Ala Phe Met
-110        -105            -100 ctc gtg ttc acg atg gca tcg atc gca tcg gct gct gag gaa gca aaa         328
Leu Val Phe Thr Met Ala Ser Ile Ala Ser Ala Ala Glu Glu Ala Lys
-95             -90             -85             -80 gaa aaa tat tta att ggc ttt aat gag cag gaa gct gtc agt gag ttt         376
Glu Lys Tyr Leu Ile Gly Phe Asn Glu Gln Glu Ala Val Ser Glu Phe
            -75             -70             -65 gta gaa caa gta gag gca aat gac gag gtc gcc att ctc tct gag gaa         424
Val Glu Gln Val Glu Ala Asn Asp Glu Val Ala Ile Leu Ser Glu Glu
        -60             -55             -50 gag gaa gtc gaa att gaa ctg ctt cat gag ttt gaa acg att cct gtt         472
Glu Glu Val Glu Ile Glu Leu Leu His Glu Phe Glu Thr Ile Pro Val
    -45             -40             -35 tta tcc gtt gag tta agc cca gaa gat gtg gac gcg ctt gaa ctt gat         520
Leu Ser Val Glu Leu Ser Pro Glu Asp Val Asp Ala Leu Glu Leu Asp
 -30             -25             -20 cca gcg att tct tat att gaa gag gat gca gaa gta acg aca atg gcg         568
Pro Ala Ile Ser Tyr Ile Glu Glu Asp Ala Glu Val Thr Thr Met Ala
-15             -10             -5              -1  1 caa aca atc cca tgg gga att agc cgt gtg caa gcc ccg gct gcc cat         616
Gln Thr Ile Pro Trp Gly Ile Ser Arg Val Gln Ala Pro Ala Ala His
                5               10              15 aac cgt gga ttg aca ggt tct ggt gta aaa gtt gct gtc ctc gat aca         664
Asn Arg Gly Leu Thr Gly Ser Gly Val Lys Val Ala Val Leu Asp Thr
        20              25              30 ggt att tcc act cat cca gac tta aat att cgt ggt ggc gct agc ttt         712
Gly Ile Ser Thr His Pro Asp Leu Asn Ile Arg Gly Gly Ala Ser Phe
    35              40              45 gta cca ggg gaa cca tcc act caa gat ggg aat ggg cat ggc acg cat         760
Val Pro Gly Glu Pro Ser Thr Gln Asp Gly Asn Gly His Gly Thr His
50              55              60              65 gtg gcc ggg acg att gct gct tta aac aat tcg att ggc gtt ctt ggc         808
Val Ala Gly Thr Ile Ala Ala Leu Asn Asn Ser Ile Gly Val Leu Gly
            70              75              80 gta gcg cct agt gcg gaa cta tac gct gtt aaa gtt tta gga gcc gac         856
Val Ala Pro Ser Ala Glu Leu Tyr Ala Val Lys Val Leu Gly Ala Asp
        85              90              95 ggt aga ggt gca atc agc tcg att gcc caa ggg ttg gaa tgg gca ggg         904
Gly Arg Gly Ala Ile Ser Ser Ile Ala Gln Gly Leu Glu Trp Ala Gly
    100             105             110 aac aat ggc atg cac gtt gct aat ttg agt tta gga agc cct tcg cca         952
Asn Asn Gly Met His Val Ala Asn Leu Ser Leu Gly Ser Pro Ser Pro
115             120             125 agt gcc aca ctt gag caa gct gtt aat agc gcg act tct aga ggc gtt        1000
Ser Ala Thr Leu Glu Gln Ala Val Asn Ser Ala Thr Ser Arg Gly Val
130             135             140             145 ctt gtt gta gcg gca tct ggg aat tca ggt gca agc tca atc agc tat        1048
Leu Val Val Ala Ala Ser Gly Asn Ser Gly Ala Ser Ser Ile Ser Tyr
            150             155             160 ccg gcc cgt tat gcg aac gca atg gca gtc gga gct act gac caa aac        1096
Pro Ala Arg Tyr Ala Asn Ala Met Ala Val Gly Ala Thr Asp Gln Asn
        165             170             175 aac aac cgc gcc agc ttt tca cag tat ggc cca ggg ctt gac att atg        1144
```

-continued

```
Asn Asn Arg Ala Ser Phe Ser Gln Tyr Gly Pro Gly Leu Asp Ile Met
        180                 185                 190 gca cca ggg gta aac att cag agc aca tac cca ggt tca acg tat gcc    1192
Ala Pro Gly Val Asn Ile Gln Ser Thr Tyr Pro Gly Ser Thr Tyr Ala
195                 200                 205 agc tta aac ggt aca tcg atg gct act cct cat gtt gca ggt gca gca    1240
Ser Leu Asn Gly Thr Ser Met Ala Thr Pro His Val Ala Gly Ala Ala
210                 215                 220                 225 gcc ctt gtt aaa caa aag aac cca tct tgg tcc aat gta caa atc cgc    1288
Ala Leu Val Lys Gln Lys Asn Pro Ser Trp Ser Asn Val Gln Ile Arg
                230                 235                 240 aac cat cta aag aat acg gca acg agc tta gga agc acg aac ttg tat    1336
Asn His Leu Lys Asn Thr Ala Thr Ser Leu Gly Ser Thr Asn Leu Tyr
            245                 250                 255 gga agc gga ctt gtc aat gca gaa gcg gca aca cgc taatcaataa         1382
Gly Ser Gly Leu Val Asn Ala Glu Ala Ala Thr Arg
        260                 265 aaaaaccgtg tgcgcttaaa gggcacagct ttttttgtgt atgaatcgaa aaaagagaac  1442
agatcgcagg tctcaaaaat cgagcgtaaa gggttgttta agctctttta cgctcgcagg  1502
tcttatcgct atacaatgga aaattcacgt cttttgactt tcatggcata tttatttaag  1562
tattcgtttg cttttcgta ctctccgttt ttctggtacc tccttctact atgggaaagg   1622
tctgatcaat gtcgaagctg ccgctcaata acatattcta acaaatagca tatagaaaaa  1682
gctagtgttt ttagcactag cttttcttc attctgatga aggttgttca atattttgaa   1742
tccgttccat gatcgtcggg taccgagctc t                                 1773
```

<210> SEQ ID NO 2
<211> LENGTH: 380
<212> TYPE: PRT
<213> ORGANISM: Bacillus licheniformis ATCC 68614

<400> SEQUENCE: 2

```
Met Met Arg Lys Lys Ser Phe Trp Leu Gly Met Leu Thr Ala Phe
    -110                -105                -100

Met Leu Val Phe Thr Met Ala Ser Ile Ala Ser Ala Ala Glu Glu Ala
        -95                 -90                 -85

Lys Glu Lys Tyr Leu Ile Gly Phe Asn Glu Gln Glu Ala Val Ser Glu
-80                 -75                 -70                 -65

Phe Val Glu Gln Val Glu Ala Asn Asp Glu Val Ala Ile Leu Ser Glu
            -60                 -55                 -50

Glu Glu Glu Val Glu Ile Glu Leu Leu His Glu Phe Glu Thr Ile Pro
        -45                 -40                 -35

Val Leu Ser Val Glu Leu Ser Pro Glu Asp Val Asp Ala Leu Glu Leu
    -30                 -25                 -20

Asp Pro Ala Ile Ser Tyr Ile Glu Glu Asp Ala Glu Val Thr Thr Met
-15                 -10                  -5                  -1

Ala Gln Thr Ile Pro Trp Gly Ile Ser Arg Val Gln Ala Pro Ala Ala
1                    5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
```

-continued

```
                65                  70                  75                  80
Gly Val Ala Pro Ser Ala Glu Leu Tyr Ala Val Lys Val Leu Gly Ala
                    85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
                180                 185                 190

Met Ala Pro Gly Val Asn Ile Gln Ser Thr Tyr Pro Gly Ser Thr Tyr
            195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 3
<211> LENGTH: 1143
<212> TYPE: DNA
<213> ORGANISM: Bacillus lentus alkaline protease S3T/V4I/G61A/V199I
<220> FEATURE:
<221> NAME/KEY: CDS
<222> LOCATION: (1)..(1140)
<220> FEATURE:
<221> NAME/KEY: mat_peptide
<222> LOCATION: (334)..(1140)

<400> SEQUENCE: 3 atg atg  agg aaa aag agt ttt tgg ctt ggg atg ctg  acg gcc ttc         45
Met Met  Arg Lys Lys Ser Phe Trp Leu Gly Met Leu  Thr Ala Phe
    -110          -105                 -100 atg ctc gtg ttc acg atg gca tcg atc gca tcg gct gct gag gaa gca      93
Met Leu Val Phe Thr Met Ala Ser Ile Ala Ser Ala Ala Glu Glu Ala
    -95                 -90                  -85 aaa gaa aaa tat tta att ggc ttt aat gag cag gaa gct gtc agt gag     141
Lys Glu Lys Tyr Leu Ile Gly Phe Asn Glu Gln Glu Ala Val Ser Glu
-80                  -75                  -70                  -65 ttt gta gaa caa gta gag gca aat gac gag gtc gcc att ctc tct gag     189
Phe Val Glu Gln Val Glu Ala Asn Asp Glu Val Ala Ile Leu Ser Glu
                -60                  -55                  -50 gaa gag gaa gtc gaa att gaa ctg ctt cat gag ttt gaa acg att cct     237
Glu Glu Glu Val Glu Ile Glu Leu Leu His Glu Phe Glu Thr Ile Pro
            -45                  -40                  -35 gtt tta tcc gtt gag tta agc cca gaa gat gtg gac gcg ctt gaa ctt     285
Val Leu Ser Val Glu Leu Ser Pro Glu Asp Val Asp Ala Leu Glu Leu
        -30                  -25                  -20 gat cca gcg att tct tat att gaa gag gat gca gaa gta acg aca atg     333
Asp Pro Ala Ile Ser Tyr Ile Glu Glu Asp Ala Glu Val Thr Thr Met
    -15                  -10                  -5                   -1
```

-continued

```
gcg caa aca atc cca tgg gga att agc cgt gtg caa gcc ccg gct gcc    381
Ala Gln Thr Ile Pro Trp Gly Ile Ser Arg Val Gln Ala Pro Ala Ala
 1               5                  10                  15 cat aac cgt gga ttg aca ggt tct ggt gta aaa gtt gct gtc ctc gat    429
His Asn Arg Gly Leu Thr Gly Ser Gly Val Lys Val Ala Val Leu Asp
             20                  25                  30 aca ggt att tcc act cat cca gac tta aat att cgt ggt ggc gct agc    477
Thr Gly Ile Ser Thr His Pro Asp Leu Asn Ile Arg Gly Gly Ala Ser
         35                  40                  45 ttt gta cca ggg gaa cca tcc act caa gat ggg aat gct cat ggc acg    525
Phe Val Pro Gly Glu Pro Ser Thr Gln Asp Gly Asn Ala His Gly Thr
     50                  55                  60 cat gtg gcc ggg acg att gct gct tta aac aat tcg att ggc gtt ctt    573
His Val Ala Gly Thr Ile Ala Ala Leu Asn Asn Ser Ile Gly Val Leu
 65                  70                  75                  80 ggc gta gcg cct agt gcg gaa cta tac gct gtt aaa gtt tta gga gcc    621
Gly Val Ala Pro Ser Ala Glu Leu Tyr Ala Val Lys Val Leu Gly Ala
                 85                  90                  95 gac ggt aga ggt gca atc agc tcg att gcc caa ggg ttg gaa tgg gca    669
Asp Gly Arg Gly Ala Ile Ser Ser Ile Ala Gln Gly Leu Glu Trp Ala
            100                 105                 110 ggg aac aat ggc atg cac gtt gct aat ttg agt tta gga agc cct tcg    717
Gly Asn Asn Gly Met His Val Ala Asn Leu Ser Leu Gly Ser Pro Ser
        115                 120                 125 cca agt gcc aca ctt gag caa gct gtt aat agc gcg act tct aga ggc    765
Pro Ser Ala Thr Leu Glu Gln Ala Val Asn Ser Ala Thr Ser Arg Gly
    130                 135                 140 gtt ctt gtt gta gcg gca tct ggg aat tca ggt gca agc tca atc agc    813
Val Leu Val Val Ala Ala Ser Gly Asn Ser Gly Ala Ser Ser Ile Ser
145                 150                 155                 160 tat ccg gcc cgt tat gcg aac gca atg gca gtc gga gct act gac caa    861
Tyr Pro Ala Arg Tyr Ala Asn Ala Met Ala Val Gly Ala Thr Asp Gln
                165                 170                 175 aac aac aac cgc gcc agc ttt tca cag tat ggc gcc ggg ctt gac att    909
Asn Asn Asn Arg Ala Ser Phe Ser Gln Tyr Gly Ala Gly Leu Asp Ile
            180                 185                 190 gtg gca ccc ggg gta aac att cag agc aca tac cca ggt tca acg tat    957
Val Ala Pro Gly Val Asn Ile Gln Ser Thr Tyr Pro Gly Ser Thr Tyr
        195                 200                 205 gcc agc tta aac ggt aca tcg atg gct act cct cat gtt gca ggt gca   1005
Ala Ser Leu Asn Gly Thr Ser Met Ala Thr Pro His Val Ala Gly Ala
    210                 215                 220 gca gcc ctt gtt aaa caa aag aac cca tct tgg tcc aat gta caa atc   1053
Ala Ala Leu Val Lys Gln Lys Asn Pro Ser Trp Ser Asn Val Gln Ile
225                 230                 235                 240 cgc aac cat cta aag aat acg gca acg agc tta gga agc acg aac ttg   1101
Arg Asn His Leu Lys Asn Thr Ala Thr Ser Leu Gly Ser Thr Asn Leu
                245                 250                 255 tat gga agc gga ctt gtc aat gca gaa gcg gca aca cgc taa            1143
Tyr Gly Ser Gly Leu Val Asn Ala Glu Ala Ala Thr Arg
            260                 265
```

<210> SEQ ID NO 4
<211> LENGTH: 380
<212> TYPE: PRT
<213> ORGANISM: Bacillus lentus alkaline protease S3T/V4I/G61A/V199I

<400> SEQUENCE: 4

```
Met Met  Arg Lys Lys Ser Phe  Trp Leu Gly Met Leu  Thr Ala Phe
    -110             -105                 -100
```

```
Met Leu Val Phe Thr Met Ala Ser Ile Ala Ser Ala Ala Glu Glu Ala
    -95                 -90                 -85

Lys Glu Lys Tyr Leu Ile Gly Phe Asn Glu Gln Ala Val Ser Glu
-80             -75                 -70                 -65

Phe Val Glu Gln Val Glu Ala Asn Asp Glu Val Ala Ile Leu Ser Glu
                -60                 -55                 -50

Glu Glu Glu Val Glu Ile Glu Leu Leu His Glu Phe Glu Thr Ile Pro
            -45                 -40                 -35

Val Leu Ser Val Glu Leu Ser Pro Glu Asp Val Asp Ala Leu Glu Leu
            -30                 -25                 -20

Asp Pro Ala Ile Ser Tyr Ile Glu Glu Asp Ala Glu Val Thr Thr Met
    -15                 -10                  -5                 -1

Ala Gln Thr Ile Pro Trp Gly Ile Ser Arg Val Gln Ala Pro Ala Ala
  1                   5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Ala His Gly Thr
 50                  55                  60

His Val Ala Gly Thr Ile Ala Ala Leu Asn Asn Ser Ile Gly Val Leu
 65              70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
             100                 105                 110

Gly Asn Asn Gly Met His Val Ala Asn Leu Ser Leu Gly Ser Pro Ser
             115                 120                 125

Pro Ser Ala Thr Leu Glu Gln Ala Val Asn Ser Ala Thr Ser Arg Gly
         130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
             165                 170                 175

Asn Asn Asn Arg Ala Ser Phe Ser Gln Tyr Gly Ala Gly Leu Asp Ile
             180                 185                 190

Val Ala Pro Gly Val Asn Ile Gln Ser Thr Tyr Pro Gly Ser Thr Tyr
         195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
             260                 265

<210> SEQ ID NO 5
<211> LENGTH: 1143
<212> TYPE: DNA
<213> ORGANISM: Bacillus lentus alkaline protease S3T/V4I/G61A/V199I/
      L211D
<220> FEATURE:
<221> NAME/KEY: CDS
<222> LOCATION: (1)..(1140)
```

-continued

```
<220> FEATURE:
<221> NAME/KEY: mat_peptide
<222> LOCATION: (334)..(1140)

<400> SEQUENCE: 5 atg atg  agg aaa aag agt ttt  tgg ctt ggg atg ctg  acg gcc ttc           45
Met Met  Arg Lys Lys Ser Phe  Trp Leu Gly Met Leu  Thr Ala Phe
    -110             -105                  -100 atg ctc gtg ttc acg atg gca tcg atc gca tcg gct gct gag gaa gca         93
Met Leu Val Phe Thr Met Ala Ser Ile Ala Ser Ala Ala Glu Glu Ala
    -95                 -90                 -85 aaa gaa aaa tat tta att ggc ttt aat gag cag gaa gct gtc agt gag        141
Lys Glu Lys Tyr Leu Ile Gly Phe Asn Glu Gln Glu Ala Val Ser Glu
-80                 -75                 -70                 -65 ttt gta gaa caa gta gag gca aat gac gag gtc gcc att ctc tct gag        189
Phe Val Glu Gln Val Glu Ala Asn Asp Glu Val Ala Ile Leu Ser Glu
                -60                 -55                 -50 gaa gag gaa gtc gaa att gaa ctg ctt cat gag ttt gaa acg att cct        237
Glu Glu Glu Val Glu Ile Glu Leu Leu His Glu Phe Glu Thr Ile Pro
            -45                 -40                 -35 gtt tta tcc gtt gag tta agc cca gaa gat gtg gac gcg ctt gaa ctt        285
Val Leu Ser Val Glu Leu Ser Pro Glu Asp Val Asp Ala Leu Glu Leu
        -30                 -25                 -20 gat cca gcg att tct tat att gaa gag gat gca gaa gta acg aca atg        333
Asp Pro Ala Ile Ser Tyr Ile Glu Glu Asp Ala Glu Val Thr Thr Met
    -15                 -10                 -5                  -1 gcg caa aca atc cca tgg gga att agc cgt gtg caa gcc ccg gct gcc        381
Ala Gln Thr Ile Pro Trp Gly Ile Ser Arg Val Gln Ala Pro Ala Ala
1                 5                   10                  15 cat aac cgt gga ttg aca ggt tct ggt gta aaa gtt gct gtc ctc gat        429
His Asn Arg Gly Leu Thr Gly Ser Gly Val Lys Val Ala Val Leu Asp
            20                  25                  30 aca ggt att tcc act cat cca gac tta aat att cgt ggt ggc gct agc        477
Thr Gly Ile Ser Thr His Pro Asp Leu Asn Ile Arg Gly Gly Ala Ser
        35                  40                  45 ttt gta cca ggg gaa cca tcc act caa gat ggg aat gct cat ggc acg        525
Phe Val Pro Gly Glu Pro Ser Thr Gln Asp Gly Asn Ala His Gly Thr
    50                  55                  60 cat gtg gcc ggg acg att gct gct tta aac aat tcg att ggc gtt ctt        573
His Val Ala Gly Thr Ile Ala Ala Leu Asn Asn Ser Ile Gly Val Leu
65                  70                  75                  80 ggc gta gcg cct agt gcg gaa cta tac gct gtt aaa gtt tta gga gcc        621
Gly Val Ala Pro Ser Ala Glu Leu Tyr Ala Val Lys Val Leu Gly Ala
                85                  90                  95 gac ggt aga ggt gca atc agc tcg att gcc caa ggg ttg gaa tgg gca        669
Asp Gly Arg Gly Ala Ile Ser Ser Ile Ala Gln Gly Leu Glu Trp Ala
            100                 105                 110 ggg aac aat ggc atg cac gtt gct aat ttg agt tta gga agc cct tcg        717
Gly Asn Asn Gly Met His Val Ala Asn Leu Ser Leu Gly Ser Pro Ser
        115                 120                 125 cca agt gcc aca ctt gag caa gct gtt aat agc gcg act tct aga ggc        765
Pro Ser Ala Thr Leu Glu Gln Ala Val Asn Ser Ala Thr Ser Arg Gly
    130                 135                 140 gtt ctt gtt gta gcg gca tct ggg aat tca ggt gca agc tca atc agc        813
Val Leu Val Val Ala Ala Ser Gly Asn Ser Gly Ala Ser Ser Ile Ser
145                 150                 155                 160 tat ccg gcc cgt tat gcg aac gca atg gca gtc gga gct act gac caa        861
Tyr Pro Ala Arg Tyr Ala Asn Ala Met Ala Val Gly Ala Thr Asp Gln
                165                 170                 175 aac aac aac cgc gcc agc ttt tca cag tat ggc gcc ggg ctt gac att        909
Asn Asn Asn Arg Ala Ser Phe Ser Gln Tyr Gly Ala Gly Leu Asp Ile
```

-continued

```
                Asn Asn Asn Arg Ala Ser Phe Ser Gln Tyr Gly Ala Gly Leu Asp Ile
                            180                 185                 190 gtg gca ccc ggg gta aac att cag agc aca tac cca ggt tca acg tat         957
Val Ala Pro Gly Val Asn Ile Gln Ser Thr Tyr Pro Gly Ser Thr Tyr
        195                 200                 205 gcc agc gac aac ggt aca tcg atg gct act cct cat gtt gca ggt gca        1005
Ala Ser Asp Asn Gly Thr Ser Met Ala Thr Pro His Val Ala Gly Ala
    210                 215                 220 gca gcc ctt gtt aaa caa aag aac cca tct tgg tcc aat gta caa atc        1053
Ala Ala Leu Val Lys Gln Lys Asn Pro Ser Trp Ser Asn Val Gln Ile
225                 230                 235                 240 cgc aac cat cta aag aat acg gca acg agc tta gga agc acg aac ttg        1101
Arg Asn His Leu Lys Asn Thr Ala Thr Ser Leu Gly Ser Thr Asn Leu
                245                 250                 255 tat gga agc gga ctt gtc aat gca gaa gcg gca aca cgc taa                1143
Tyr Gly Ser Gly Leu Val Asn Ala Glu Ala Ala Thr Arg
        260                 265
```

<210> SEQ ID NO 6
<211> LENGTH: 380
<212> TYPE: PRT
<213> ORGANISM: Bacillus lentus alkaline protease S3T/V4I/G61A/V199I/
      L211D

<400> SEQUENCE: 6

```
Met Met     Arg Lys Lys Ser Phe     Trp Leu Gly Met Leu   Thr Ala Phe
    -110                -105                -100

Met Leu Val Phe Thr Met Ala Ser Ile Ala Ser Ala Glu Glu Ala
    -95                 -90                 -85

Lys Glu Lys Tyr Leu Ile Gly Phe Asn Glu Gln Glu Ala Val Ser Glu
-80                 -75                 -70                 -65

Phe Val Glu Gln Val Glu Ala Asn Asp Glu Val Ala Ile Leu Ser Glu
                -60                 -55                 -50

Glu Glu Glu Val Glu Ile Glu Leu Leu His Glu Phe Glu Thr Ile Pro
                -45                 -40                 -35

Val Leu Ser Val Glu Leu Ser Pro Glu Asp Val Asp Ala Leu Glu Leu
        -30                 -25                 -20

Asp Pro Ala Ile Ser Tyr Ile Glu Glu Asp Ala Glu Val Thr Thr Met
    -15                 -10                 -5                  -1

Ala Gln Thr Ile Pro Trp Gly Ile Ser Arg Val Gln Ala Pro Ala Ala
1                   5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Ala His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
        100                 105                 110

Gly Asn Asn Gly Met His Val Ala Asn Leu Ser Leu Gly Ser Pro Ser
    115                 120                 125

Pro Ser Ala Thr Leu Glu Gln Ala Val Asn Ser Ala Thr Ser Arg Gly
130                 135                 140
```

```
Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
            195                 200                 205

Ala Ser Asp Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
tcacagtatg gcgccgggct tgacatt         27

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
aatgtcaagc ccggcgccat actgtga         27

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
gggcttgaca ttgtggcacc cggggtaaac      30

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10 gtttacccccg ggtgccacaa tgtcaagccc     30

<210> SEQ ID NO 11
<211> LENGTH: 27
<212> TYPE: DNA
<213> ORGANISM: Artificial Sequence
<220> FEATURE:

-continued

<223> OTHER INFORMATION: Primer

<400> SEQUENCE: 11
caagatggga atgctcatgg cacgcat                    27

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
atgcgtgcca tgagcattcc catcttg                    27

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
acgtatgcca gcgacaacgg tacatcg                    27

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
cgatgtaccg ttgtcgctgg catac                      25

<210> SEQ ID NO 15
<211> LENGTH: 269
<212> TYPE: PRT
<213> ORGANISM: S3T/V4I/G61A/V199I

<400> SEQUENCE: 15

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Ala His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
        180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

<210> SEQ ID NO 16
<211> LENGTH: 269
<212> TYPE: PRT
<213> ORGANISM: S3T/V4I/G61A/V199I/L211D

<400> SEQUENCE: 16

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Ala His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
        180                 185                 190

Val Ala Pro Gly Val Asn Ile Gln Ser Thr Tyr Pro Gly Ser Thr Tyr
        195                 200                 205

Ala Ser Asp Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg

<210> SEQ ID NO 17
<211> LENGTH: 268
<212> TYPE: PRT
<213> ORGANISM: Subtilisin 309

<400> SEQUENCE: 17

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Gln Ser Thr Tyr Pro Gly Ser Thr Tyr Ala
        195                 200                 205

Ser Leu Asn Gly Thr Ser Met Ala Thr Pro His Val Ala Gly Ala Ala
    210                 215                 220

Ala Leu Val Lys Gln Lys Asn Pro Ser Trp Ser Asn Val Gln Ile Arg
225                 230                 235                 240

Asn His Leu Lys Asn Thr Ala Thr Ser Leu Gly Ser Thr Asn Leu Tyr
                245                 250                 255

Gly Ser Gly Leu Val Asn Ala Glu Ala Ala Thr Arg
            260                 265
```

<210> SEQ ID NO 18
<211> LENGTH: 268
<212> TYPE: PRT
<213> ORGANISM: Subtilisin PB92

<400> SEQUENCE: 18

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
```

```
                    50                  55                  60
His Val Ala Gly Thr Ile Ala Ala Leu Asn Asn Ser Ile Gly Val Leu
 65                  70                  75                  80

Gly Val Ala Pro Asn Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
145                 150                 155                 160

Tyr Ala Arg Tyr Ala Asn Ala Met Ala Val Gly Ala Thr Asp Gln Asn
                165                 170                 175

Asn Asn Arg Ala Ser Phe Ser Gln Tyr Gly Ala Gly Leu Asp Ile Val
            180                 185                 190

Ala Pro Gly Val Asn Val Gln Ser Thr Tyr Pro Gly Ser Thr Tyr Ala
            195                 200                 205

Ser Leu Asn Gly Thr Ser Met Ala Thr Pro His Val Ala Gly Ala Ala
            210                 215                 220

Ala Leu Val Lys Gln Lys Asn Pro Ser Trp Ser Asn Val Gln Ile Arg
225                 230                 235                 240

Asn His Leu Lys Asn Thr Ala Thr Ser Leu Gly Ser Thr Asn Leu Tyr
                245                 250                 255

Gly Ser Gly Leu Val Asn Ala Glu Ala Ala Thr Arg
            260                 265

<210> SEQ ID NO 19
<211> LENGTH: 274
<212> TYPE: PRT
<213> ORGANISM: Subtilisin Carlsberg

<400> SEQUENCE: 19

Ala Gln Thr Val Pro Tyr Gly Ile Pro Leu Ile Lys Ala Asp Lys Val
 1                   5                  10                  15

Gln Ala Gln Gly Phe Lys Gly Ala Asn Val Lys Val Ala Val Leu Asp
                 20                  25                  30

Thr Gly Ile Gln Ala Ser His Pro Asp Leu Asn Val Val Gly Gly Ala
             35                  40                  45

Ser Phe Val Ala Gly Glu Ala Tyr Asn Thr Asp Gly Asn Gly His Gly
     50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Thr Tyr Ser Gly Ile Val Ser Gly Ile Glu Trp
            100                 105                 110

Ala Thr Thr Asn Gly Met Asp Val Ile Asn Met Ser Leu Gly Gly Pro
            115                 120                 125

Ser Gly Ser Thr Ala Met Lys Gln Ala Val Asp Asn Ala Tyr Ala Arg
            130                 135                 140

Gly Val Val Val Val Ala Ala Ala Gly Asn Ser Gly Ser Ser Gly Asn
145                 150                 155                 160
```

```
Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Ser Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 20
<211> LENGTH: 275
<212> TYPE: PRT
<213> ORGANISM: Subtilisin BPN'

<400> SEQUENCE: 20

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly Ser
145                 150                 155                 160

Ser Ser Thr Val Gly Tyr Pro Gly Lys Tyr Pro Ser Val Ile Ala Val
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255
```

-continued

```
Leu Gly Asp Ser Phe Tyr Tyr Gly Lys Gly Leu Ile Asn Val Gln Ala
            260             265             270

Ala Ala Gln
        275

<210> SEQ ID NO 21
<211> LENGTH: 263
<212> TYPE: PRT
<213> ORGANISM: Consensus

<400> SEQUENCE: 21

Ala Gln Pro Trp Gly Ile Ser Arg Val Gln Ala Pro Ala Ala His Asn
1               5                   10                  15

Arg Gly Leu Thr Gly Ser Gly Val Lys Val Ala Val Leu Asp Thr Gly
            20                  25                  30

Ile Ser Thr His Pro Asp Leu Asn Ile Arg Gly Gly Ala Ser Phe Val
            35                  40                  45

Pro Gly Glu Pro Ser Thr Gln Asp Gly Asn His Gly Thr His Val Ala
        50                  55                  60

Gly Thr Ile Ala Ala Leu Asn Asn Ser Ile Gly Val Leu Gly Val Ala
65                  70                  75                  80

Pro Ser Ala Glu Leu Tyr Ala Val Lys Val Leu Gly Ala Ser Gly Ser
                85                  90                  95

Gly Ser Val Ser Ser Ile Ala Gln Gly Leu Glu Trp Ala Gly Asn Asn
            100                 105                 110

Gly Met His Val Ala Asn Leu Ser Leu Gly Ser Pro Ser Pro Ser Ala
            115                 120                 125

Thr Leu Glu Gln Ala Val Asn Ser Ala Thr Ser Arg Gly Val Leu Val
        130                 135                 140

Val Ala Ala Ser Gly Asn Ser Gly Ala Ser Ile Ser Tyr Pro Ala Arg
145                 150                 155                 160

Tyr Ala Asn Ala Met Ala Val Gly Ala Thr Asp Gln Asn Asn Asn Arg
                165                 170                 175

Ala Ser Phe Ser Gln Tyr Gly Ala Gly Leu Asp Ile Val Ala Pro Gly
            180                 185                 190

Val Asn Gln Ser Thr Tyr Pro Gly Ser Thr Tyr Ala Ser Asn Gly Thr
        195                 200                 205

Ser Met Ala Thr Pro His Val Ala Gly Ala Ala Ala Leu Val Lys Gln
            210                 215                 220

Lys Asn Pro Ser Trp Ser Asn Val Gln Ile Arg Asn His Leu Lys Asn
225                 230                 235                 240

Thr Ala Thr Ser Leu Gly Ser Thr Asn Tyr Leu Gly Ser Gly Leu Val
                245                 250                 255

Asn Ala Glu Ala Ala Thr Arg
            260
```